US008017583B2

(12) United States Patent
MacLean et al.

(10) Patent No.: US 8,017,583 B2
(45) Date of Patent: Sep. 13, 2011

(54) METHODS OF USE OF EPSILON INHIBITOR COMPOUNDS FOR THE ATTENUATION OF PAIN

(75) Inventors: Derek MacLean, Los Altos, CA (US); Qun Yin, Palo Alto, CA (US)

(73) Assignee: KAI Pharmaceuticals, Inc., South San Francisco, CA (US)

( * ) Notice: Subject to any disclaimer, the term of this patent is extended or adjusted under 35 U.S.C. 154(b) by 359 days.

(21) Appl. No.: 12/018,111

(22) Filed: Jan. 22, 2008

(65) Prior Publication Data
US 2009/0062209 A1    Mar. 5, 2009

Related U.S. Application Data

(60) Provisional application No. 60/881,396, filed on Jan. 19, 2007, provisional application No. 60/903,684, filed on Feb. 26, 2007, provisional application No. 60/917,876, filed on May 14, 2007, provisional application No. 60/977,332, filed on Oct. 3, 2007.

(51) Int. Cl.
*A61K 38/16* (2006.01)
*A61K 38/00* (2006.01)
*C07K 14/00* (2006.01)

(52) U.S. Cl. ....... 514/21.4; 514/18.3; 530/300; 530/326

(58) Field of Classification Search ........................ None
See application file for complete search history.

(56) References Cited

U.S. PATENT DOCUMENTS

| | | | |
|---|---|---|---|
| 4,847,240 | A | 7/1989 | Ryser et al. |
| 5,141,957 | A | 8/1992 | Jiang et al. |
| 5,204,370 | A | 4/1993 | Jiang et al. |
| 5,216,014 | A | 6/1993 | Jiang et al. |
| 5,270,310 | A | 12/1993 | Bell et al. |
| 5,292,737 | A | 3/1994 | Defauw |
| 5,344,841 | A | 9/1994 | Jiang et al. |
| 5,360,818 | A | 11/1994 | Jiang et al. |
| 5,380,746 | A | 1/1995 | Barth et al. |
| 5,432,198 | A | 7/1995 | Jagdmann |
| 5,489,608 | A | 2/1996 | Kleinschroth et al. |
| 5,747,641 | A | 5/1998 | Frankel et al. |
| 5,783,405 | A | 7/1998 | Mochly-Rosen et al. |
| 5,888,762 | A | 3/1999 | Joliot et al. |
| 6,156,977 | A | 12/2000 | Benito-Navazo |
| 6,255,057 | B1 | 7/2001 | Gordon et al. |
| 6,376,467 | B1 | 4/2002 | Messing et al. |
| 6,423,684 | B1 | 7/2002 | Mochly-Rosen |
| 6,593,292 | B1 | 7/2003 | Rothbard et al. |
| 6,686,334 | B2 | 2/2004 | Messing et al. |
| 2002/0151465 | A1 | 10/2002 | Messing et al. |
| 2003/0104622 | A1 | 6/2003 | Robbins et al. |
| 2003/0199677 | A1 | 10/2003 | Avrameas et al. |
| 2003/0206900 | A1 | 11/2003 | Ternynck et al. |
| 2005/0187156 | A1 | 8/2005 | Mochly-Rosen |

FOREIGN PATENT DOCUMENTS

EP    0 434 057    6/1991

OTHER PUBLICATIONS

Wells, J.A. (1990). Additivity of mutational effects in proteins. Biochemistry. 29(37):8509-8517.*
Ngo et al. (1994). Computational complexity, protein structure prediction, and the Levinthal paradox. In Merz and Le Grand (Eds.) The Protein Folding Problem and Tertiary Structure Prediction. Birkhauser:Boston, pp. 491-495.*
Birchall et al., J. Pharmacol. Exp. Ther. (1994) 268:922-929.
Boehm et al., J. Neurosci. (1996) 16:4596-4603.
Chakravarthy et al., Anal. Biochem. (1991) 196:144-150.
Chen and Levine, J. Pain (2005) 6:439-446.
Chen et al., PNAS USA (2001) 98(20):11114-11119.
Davis et al., J. Med. Chem. (1992) 35:994-1001.
Fabre et al., Bioorg. Med. Chem. (1993) 1:193-196.
Gschwendt et al., FEBS Lett. (1996) 392:77-80.
Johnson et al., J. Biol. Chem. (1996) 271(40):24962-24966.
Khasar et al., Neuron (1999) 24:253-260.
Kitano et al., Meth. Enzymol. (1986) 124:349-352.
Lehel et al., Anal. Biochem. (1997) 244:340-346.
Merritt et al., Cell Signal. (1997) 9:53-57.
Messing et al., J. Biol. Chem. (1991) 266:23428-23432.
Reichling & Levine, Pain (1999) Suppl. 6 (Aug.):S103-S109.
Scholze et al., J. Neurosci. (2002) 22:5823-5832.
Toullec et al., J. Biol. Chem. (1991) 266:15771-81.
Wilkinson et al., Biochem. J. (1993) 294:335-7.
Zhu and Ikeda, J. Neurophysiol. (1994) 74:1546-1560.
International Search Report and Written Opinion for PCT/US2008/051736, mailed Sep. 15, 2008, 9 pages.
Daria Mochly-Rosen, List of peptides provided for experimental use sent to Dr. Nicholas Webster, University of California, San Diego, San Diego, California, U.S., Feb. 25, 1996.
Che-Hong Chen, List of peptides provided for experimental use sent to Dr. Sue Heffelfinger, University of Cincinnati, Cincinnati, Ohio, U.S., Apr. 3, 1996.
Daria Mochly-Rosen, List of peptides provided for experimental use sent to Dr. James A. Fagin, University of Cincinnati, Cincinnati, Ohio, U.S., Apr. 3, 1996.
Che-Hong Chen, List of peptides provided for experimental use and related correspondence sent to and from Dr. Aideen Long, Trinity College, St. James' Hospital, Dublin, Ireland, Jul. 23, 1996.
Che-Hong Chen, List of peptides provided for experimental use sent to Dr. Stephen Robbins, University of Calgary, Calgary, Canada, Oct. 21, 1996.
Che-Hong Chen, List of peptides provided for experimental use sent to Dr. Patricia Hinkle, University of Rochester Medical School, Rochester, New York, U.S., Oct. 21, 1996.
Che-Hong Chen, List of peptides provided for experimental use sent to Dr. Susan Sergeant, Bowman Gray School of Medicine, Winston-Salem, North Carolina, U.S., Oct. 21, 1996.
Protocol and Method Paper and/or List of peptides provided for experimental use for Drs. Joan Heller Brown, Ani Banerjee, Donald M. Bers, Allen M. Samarel, Metin Avkiran, Stephan Bohm, and Aileen Long, 3 pages, 1996.
Che-Hong Chen, List of peptides provided for experimental use sent to Dr. Mohamed Boutjdir, VA Medical Center, Brooklyn, New York, U.S., Oct. 30, 1996.

(Continued)

*Primary Examiner* — Christine J Saoud
*Assistant Examiner* — Jon M Lockard
(74) *Attorney, Agent, or Firm* — King & Spalding LLP

(57) ABSTRACT

The disclosure herein relates to modified εPKC inhibitory peptides, methods of generating such peptides, and method for using εPKC inhibitory peptides for the treatment of pain.

18 Claims, 31 Drawing Sheets

OTHER PUBLICATIONS

John A. Johnson, List of peptides provided for experimental use sent to Drs. William Karnes and/or Shaun Weller, Mayo Foundation, SW Rochester, Minnesota, U.S. Dec. 16, 1996.

Che-Hong Chen, List of peptides provided for experimental use sent to Dr. David L. Greenen, Albert Einstein College of Medicine, Bronx, New York, U.S., Jan. 29, 1997.

Che-Hong Chen, List of peptides provided for experimental use sent to Dr. Judith Maloney, University of Pennsylvania School of Medicine, Philadelphia, Pennsylvania, U.S., Feb. 4, 1997.

List of peptides provided for experimental use sent to Dr. Lobby on Feb. 25, 1997.

Che-Hong Chen, List of peptides provided for experimental use and related correspondence sent to and from Dr. Kevin Claffey, Beth Israel Deaconess Medical Center, Boston, Massachusetts, U.S., Jun. 2, 1997.

Che-Hong Chen, List of peptides provided for experimental use sent to Dr. Piero Biancani, East Greenwich, Rhode Island, U.S., Jun. 2, 1997.

Kevin P. Clafferty, Letter discussing peptides and related search results sent to Dr. Daria Mochly-Rosen, Stanford University School of Medicine, Stanford, California, U.S., Apr. 15, 1997.

John A. Johnson, List of peptides provided for experimental use and related correspondence sent to and from Dr. Stuart D. Critz, University of South Alabama College of Medicine, Mobile, Alabama, U.S., Jun. 3, 1997.

Che-Hong Chen, List of peptides provided for experimental use and related journal article (Miyagawa et al.) sent to Dr. R. Kent Hermsmeyer, Oregon Regional Primate Research Center, Beaverton, Oregon, U.S., Jan. 5, 1998.

List of peptides provided for experimental use sent to Dr. Lobo, University of California, San Francisco, San Francisco, California, U.S., Feb. 11, 1998.

Che-Hong Chen, List of peptides provided for experimental use sent to Dr. Sailen Barik, University of Southern Alabama, Mobile, Alabama, U.S., Mar. 19, 1998.

Che-Hong Chen, List of peptides provided for experimental use and related correspondence sent to and from Dr. Richard Olsen, University of California, Los Angeles, School of Medicine, Los Angeles, California, U.S., Jul. 6, 1998.

Che-Hong Chen, List of peptides provided for experimental use and related correspondence sent to and from Dr. Susie Mihailidou, Royal North Shore Hospital, St. Leonards, Australia, Dec. 1, 1998.

Che-Hong Chen, List of peptides provided for experimental use and related correspondence sent to and from Dr. Jeffery Knauf, University of Cincinnati, Cincinnati, Ohio, U.S., Jul. 13, 1999.

Che-Hong Chen, List of peptides provided for experimental use sent to Dr. Steve Black, University of California, San Francisco, San Francisco, California, U.S., Jan. 5, 1998.

Che-Hong Chen, List of peptides provided for experimental use sent to Dr. Derek Miles Yellon, Hatter Institute for Cardiovascular Studies, University of College Hospital and Medical School, London, England, United Kingdom, Jun. 25, 1998.

Che-Hong Chen, List of peptides provided for experimental use sent to Dr. Katherine Murray, Vanderbilt University School of Medicine, Nashville, Tennessee, U.S., Sep. 8, 1998.

Che-Hong Chen, List of peptides provided for experimental use sent to Dr. Adrienne Gordon, University of California, San Francisco, San Francisco, California, U.S., Sep. 10, 1998.

Che-Hong Chen, List of peptides provided for experimental use sent to Dr. W. Barry VanWinkle, University of Texas Medical School at Houston, Houston, Texas, U.S., Sep. 28, 1998.

Che-Hong Chen, List of peptides provided for experimental use and related correspondence sent to and from Dr. Derek Miles Yellon, Hatter Institute for Cardiovascular Studies, University of College Hospital and Medical School, London, England, United Kingdom, Oct. 14, 1998.

Che-Hong Chen, List of peptides provided for experimental use and related correspondence regarding peptides project outline sent to and from Dr. Fiorenzo Battaini, University of Milano, Milano, Italy, Oct. 15, 1998.

Che-Hong Chen, List of peptides provided for experimental use and related correpondence sent to and from Dr. Yasuki Kihara, Kyoto University, Kyoto, Japan, Oct. 15, 1998.

Che-Hong Chen, List of peptides provided for experimental use and related correspondence sent to and from Dr. Naoaki Saito, Kobe University, Kobe, Japan, Oct. 15, 1998.

Che-Hong Chen, List of peptides provided for experimental use and related correspondence sent to and from Dr. Ashwani Malhotra, New York Medical College, Valhalla, New York, U.S., Oct. 16, 1998.

Daria Mochly-Rosen, Material Transfer Agreement and List of peptides provided for experimental use sent to Dr. Steve Black, University of California, San Francisco, San Francisco, California, U.S., Sep. 3, 1998.

Che-Hong Chen, List of peptides provided for experimental use and related correspondence sent to and from Dr. Allan Basbaum, W.M. Keck Foundation Center for Integrative Neuroscience, San Francisco, California, U.S., Oct. 21, 1998.

Che-Hong Chen, List of peptides provided for experimental use sent to Drs. Rik Derynck and Huizhou Fan, University of California, San Francisco, San Francisco, California, U.S., Oct. 27, 1998.

Che-Hong Chen, List of peptides provided for experimental use and related correspondence sent to and from Dr. Elissavet Kardami, University of Manitoba, Manitoba, Canada, Nov. 18, 1998.

Che-Hong Chen, List of peptides provided for experimental use and related correspondence sent to and from Dr. Guang S. Liu, University of South Alabama, Mobile, Alabama, U.S., Nov. 23, 1998.

Che-Hong Chen, List of peptides provided for experimental use sent to Dr. John Hayslett, Yale School of Medicine, New Haven, Connecticut, U.S., Dec. 14, 1998.

Daria Mochly-Rosen, Material Transfer Agreement and List of peptides provided for experimental use sent to Dr. Arshad Rahman, University of Illinois, Chicago, Illinois, U.S., Dec. 15, 1998.

Daria Mochly-Rosen, List of peptides provided for experimental use sent to Andrew P. Bradford, faxed on Dec. 18, 1998.

Daria Mochly-Rosen, Material Transfer Aggreement sent to Dr. Yuri Volkov, Trinity Centre for Health Sciences, St. James's Hospital, Dublin, Ireland, Dec. 15, 1998.

Daria Mochly-Rosen, Material Transfer Agreement and related document sent to Dr. Tish Murphy, NIEHS, NIH, Research Triangle Park, North Carolina, U.S., Dec. 15, 1998.

Che-Hong Chen, List of peptides provided for experimental use sent to Dr. Babu Padanilam, Washington University Medical School, St. Louis, Missouri, U.S., Jan. 5, 1999.

Daria Mochly-Rosen, Material Transfer Agreement and List of peptides provided for experimental use sent to Dr. Eric J. Nelson, University of Colorado, Denver, Colorado, U.S., Jan. 14, 1999.

Che-Hong Chen, List of peptides provided for experimental use sent to Dr. Hyeon-Gyu Shin, Vanderbilt University School of Medicine, Nashville, Tennessee, U.S., Jan. 20, 1999.

Daria Mochly-Rosen, Material Transfer Agreement, List of peptides provided for experimental use, and related correspondence sent to and from Dr. Mita Das, University of Colorado Health Sciences Center, Denver, Colorado, U.S., Jan. 11, 1999.

Che-Hong Chen, List of peptides provided for experimental use and related correspondence sent to and from Dr. Rafael Nesher, Hebrew University-Hadassah Medical Center, Jerusalem, Israel, Feb. 10, 1999.

Daria Mochly-Rosen, Material Transfer Agreement, List of peptides provided for experimental use, and related correspondence sent to and from Dr. Steven Pelech, University of British Columbia, British Columbia, Canada, Feb. 10, 1999.

Che-Hong Chen, List of peptides provided for experimental use and related correspondence sent to and from Dr. Naoaki Saito, Kobe University, Kobe, Japan, Feb. 10, 1999.

Che-Hong Chen, List of peptides provided for experimental use sent to Dr. Umberto Kucich, School of Dental Medicine, Philadelphia, Pennsylvania, U.S., Mar. 11, 1999.

List of peptides provided for experimental use sent to Dr. Imogen Coe, York University, Ontario, Canada, Apr. 8, 1999.

Che-Hong Chen, List of peptides provided for experimental use and related correspondence sent to and from Dr. Mireia Gomez-Angelats, Research Triangle Park, North Carolina, U.S., Jul. 13, 1999.

Daria Mochly-Rosen, Material Transfer Agreement, List of peptides provided for experimental use, and related correspondence sent to and from Dr. Jau-Shyong Hong, NIEHS, NIH, Research Triangle Park, North Carolina, U.S., Jul. 13, 1999.
Che-Hong Chen, List of peptides provided for experimental use and related correspondence sent to Dr. Anne-Marie Schmitt-Verhulst, Centre d'Immunologie INSERM-CNRS de Marseille-Luminy, Marseilles, France, Jul. 14, 1999.
Daria Mochly-Rosen, Material Transfer Agreement and List of peptides provided for experimental use sent to Dr. John D. Roberts, NIEHS, NIH, Research Triangle Park, North Carolina, U.S., Jul. 14, 1999.
Che-Hong Chen, List of peptides provided for experimental use sent to Dr. Jeffery Knauf, University of Cincinnati, Cincinnati, Ohio, U.S., Aug. 10, 1999.
Daria Mochly-Rosen, Material Tranfer Agreement sent to Dr. Johannes W. Hell, University of Wisconsin Medical School, Madison, Wisconsin, U.S., Sep. 22, 1999.
Che-Hong Chen, List of peptides provided for experimental use and related correspondence sent to and from Dr. Eric Nelson, University of Colorado, Denver, Colorado, U.S., Oct. 2, 1999.
Che-Hong Chen, Material Transfer Agreement, List of peptides provided for experimental use, and related correspondence sent to and from Dr. Yukitaka Shizukuda, University of Illinois, Chicago, Illinois, U.S., Nov. 5, 1999.
Daria Mochly-Rosen, Material Transfer Agreement sent to Dr. Hesam Dehghani, University of Guelph, Ontario, Canada, Nov. 8, 1999.
Daria Mochly-Rosen, Material Transfer Agreement and List of peptides provided for experimental use and related correspondence sent to and from Dr. Alexei Kourakine, Buck Center, San Francisco, California, U.S., Jan. 7, 2000.
Daria Mochly-Rosen, Material Transfer Agreement, List of peptides provided for experimental use and related correspondence sent to and from Dr. Ti-Zhi Su, Parke-Davis, Ann Arbor, Michigan, U.S., Jan. 28, 2000.
Daria Mochly-Rosen, Material Transfer Agreement and List of peptides provided for experimental use sent to Dr. Clive Baumgarten, Virginia Commonwealth University, Richmond, Virginia, U.S., Feb. 3, 2000.
Daria Mochly-Rosen, Material Transfer Agreement and List of peptides provided for experimental use sent to Dr. Pedro a. Jose, Georgetown University Hospital, Washington, Dc, U.S., Feb. 17, 1999.
Aizawa et al., Anesthesiology (2004) 101(2):381-389.
Aley et al., J Neurosci (2000) 20(12):4680-4685.
Alvarez et al., Circ Res (2001) 89(12):1246-1253.
Amadesi et al., J Physiol (2006) 575.2:555-571.
Andrukhiv et al., Am J Physiol Heart Circ Physiol (2006) 291:H2067-H2074.
Banci et al., J Biol Chem (2002) 277(15):12988-12997.
Baroudi et al., Am J Physiol Heart Circ Physiol (2006) 291:H1614-H1622.
Basu et al., PNAS USA (2005) 102(18):6285-6290.
Begley et al., Biochem Biophys Res Commun (2004) 318(4):949-954.
Berna et al., Biochim Biophys Acta (2007) 1773(4):483-501 [DOI:10.1016/j.bbamcr.2006.12.008].
Besena et al., J Biol Chem (2004) 279(32):33154-33160.
Brandman et al., J Biol Chem (2007) 282(6):4113-4123.
Braun and Mochly-Rosen, J Mol Cell Cardiol (2003) 35(8):895-903.
Bright and Mochly-Rosen, Stroke (2005) 36(12):2781-2790.
Bright et al., J Neurosci (2004) 24(31):6880-6888.
Brunelli et al., Dev Biol (2007) 304(2):604-614.
Brzoska et al., PNAS USA (1995) 92(17):7824-7828.
Budas and Mochly-Rosen, Biochem Soc Trans (2007) 35(Pt. 5):1052-1054.
Budas et al., Biochem Soc Trans (2007) 35(Pt. 5):1021-1026.
Budas et al., Pharmacol Res (2007) 55(6):523-536.
Cardone et al., J Cell Biol (1994) 124(5):717-727.
Cardone et al., J Cell Biol (1996) 133(5):997-1005.
Cesare et al., Neuron (1999) 23(3):617-624.
Chang and Tepperman, Am J Physiol Gastrointest Liver Physiol (2001) 280(4):G572-G583.
Chang and Tepperman, Br J Pharmacol (2003) 140(1):41-52.
Chaudary et al., J Pharmacol Exp Ther (2004) 310(3):1190-1198.
Chen and Mochly-Rosen, J Mol Cell Cardiol (2001) 33(3):581-585.
Chen et al., Chem Biol (2001) 140:1-7.
Chen et al., J Neurosci (2005) 25(2):507-513.
Chen et al., PNAS USA (1999) 96(22):12784-12789.
Chie et al., J Protein Chem (2003) 22(7-8):625-629.
Churchill et al., Circ Res (2005) 97(1):78-85.
Claro et al., J Pharmacol Exp Ther (2007) 322(3):964-972.
Cosen-Binker et al. J Biol Chem (2007) 282(17):13047-13058.
Costa et al., Cardiovasc Res (2007) [DOI:10.1093/cvr/cvm050].
Costa et al., Circ Res (2005) 97:329-336 [DOI:10.1161/01.RES.0000178451.08719.5b].
Csukai and Mochly-Rosen, Methods Mol Biol (1998) 88:133-139.
Csukai and Mochly-Rosen, Pharmacol Res (1999) 39(4):253-259.
Csukai et al., J Biol Chem (1997) 272(46):29200-29206.
Dallas and Khalil, Am J Physiol Cell Physiol (2003) 285(6):C1454-C1463.
De et al., J Pharmacol Exp Ther (2002) 301(1):119-128.
Dehghani et al., Reproduction (2005) 130(4):453-465.
Dell et al., J Biol Chem (2002) 277(51):49888-49895.
Dempsey et al., Am J Physiol Lung Cell Mol Physiol (2000) 279(3):L429-L438.
Dey et al., Biochem Biophys Res Commun (2007) 357:474-479.
Diamond et al., Ann N Y Acad Sci (1991) 625:473-487.
Disatnik et al., Cell Growth Differ (1994) 5(8):873-880.
Disatnik et al., Exp. Cell Res (1994) 210(2):287-297.
Disatnik et al., J Cell Sci (2002) 115(Pt. 10):2151-2163.
Disatnik et al., J Mol Cell Cardiol (1995) 27(11):2473-2481.
Disatnik et al., PNAS USA (1994) 91(2):559-563.
Dorn and Mochly-Rosen, Annu Rev Physiol (2002) 64:407-429.
Dorn et al., PNAS USA (1999) 96(22):12798-12803.
Du et al., J Immunol (2006) 176(8):4785-4792.
Endermann and Mochly-Rosen, Methods Mol Biol (2003) 233:307-325.
Endermann et al., Anal Biochem (2003) 313(2):345-347.
Fanning et al., Int Immunol (2005) 17(4):449-458.
Felber et al., Pathol Oncol Res (2007) 13(4):295-301.
Flescher and Rotem, Cell Signal (2002) 14:37-43.
Gao et al., Cardiovasc Res (2007) 75(3):584-595.
Gao et al., J Mol Cell Cardiol (2007) 43(5):601-609.
Garcia-Navarro et al., Mol Cell Endocrinol (1994) 103(1-2)133-138.
Garg and Hu, Am J Physiol Heart Circ Physiol (2007) 293:H322-H332 [DOI:10.1152/ajpheart.01035.2006].
Ghosh et al., J Cell Biochem (2004) 91(6):1109-1129.
Graeler et al., J Biol Chem (2003) 278(30):27737-27741.
Gray et al., J Biol Chem (1997) 272(49):30945-30951.
Gray et al., J Biol Chem (2004) 279(5):3596-3604.
Hassouna et al., Am J Physiol Cell Physiol (2004) 287:C1418-C1425.
Hayabuchi et al., Am J Physiol Heart Circ Physiol (2001) 281(6):H2480-2489.
Hayabuchi et al., J Physiol (2001) 530(Pt. 2):193-205.
Heider et al., Oncol Res (2004) 14(10):475-482.
Hodge et al., Nat Neurosci (1999) 2(11):997-1002.
Hool, Circ Res (2000) 87(12):1164-1171.
Hool, Curr Pharm Des (2005) 11(4):549-559.
Hool, J Physiol (2003) 554.3:743-754.
Hu et al., Am J. Physiol Heart Circ Physiol (2000) 279(6):H2658-H2664.
Huang and Walker, J Cell Sci (2004) 117(Pt.10):1971-1978.
Hucho et al., Euro J Neurosci (2006) 1-8.
Hundle et al., J Biol Chem (1997) 272(23):15028-15035.
Ikeno et al., Cardiovasc Res (2007) 73(4):699-709.
Inagaki and Mochly-Rosen, J Mol Cell Cardiol (2005) 39(2):203-211.
Inagaki et al., Cardiovasc Res (2006) 70(2):222-230.
Inagaki et al., Circulation (2000) 101(7):797-804.
Inagaki et al., Circulation (2003) 108(7) 869-875.
Inagaki et al., Circulation (2003) 108(19):2304-2307.
Inagaki et al., Circulation (2005) 111(1):44-50.

Inagaki et al., J Mol Cell Cardiol (2002) 00:1-9.
Jaburek et al., Circ Res. (2006) at <http://circres.ahajournals.org> [DOI:10.1161/01.RES.0000245106.80628.d3].
Jin et al., Am J Physiol Hearth Circ Physiol (2002) 282(6):H1970-H1977.
Johnson and Mochly-Rosen, Circ Res (1995) 76(4):654-663.
Johnson et al., Circ Res (1996)79(6):1086-1099.
Johnson et al., Life Sci (1995) 57(11):1027-1038.
Jones et al., J Inflamm (2007) 4:23 [DOI:10.1186/1476-9255-4-23].
Joseph et al., Pain (2007) 132(1-2):67-73 [DOI:10.1016/j.pain.2007.01.027].
Jung et al., Biochem Biophys Res Commun (2004) 320(3):789-794.
Jung et al., Neuroreport (2005) 16(7):741-744.
Kanno et al., J Lipid Res (2006) 47(6):1146-1156.
Karliner et al., J Mol Cell Cardiol (2000) 32(10):1779-1786.
Khasar et al., J Neurophysiol (1999) 81(3):1104-1112.
Kheifets et al., J Biol Chem (2006) 281(32):23218-23226.
Kim et al., Biochem Biophys Res Commun (2003) 309(1):1-6.
Kim et al., Jpn J Physiol (2004) 54(4):405-414.
Kim et al., Neuroscience (2007) 145:931-941.
Kinsey et al., Am J Physiol Renal Physiol (2006) 292:F853-F860[DOI:10.1152/ajprenal.00318.2006].
Knauf et al., J Biol Chem (1999) 274(33):23414-23425.
Knauf et al., J Clin Endocrinol Metab (2002) 87(5):2150-2159.
Koon et al., J Immunol (2006) 176(8):5050-5059.
Koon et al., J Pharmacol Exp Ther (2005) 314(3):1393-1400.
Koponen et al., J Neurochem (2003) 86(2):442-450.
Koyanagi et al., J Mol Cell Cardiol (2007) 43(4):517-522 [DOI:10.1016/j.yjmcc.2007.06.003].
Lange-Asschenfeldt et al., J Cereb Blood Flow Metab (2004) 24(6):636-645.
Laudanna el al., J Biol Chem (1998) 273(46):30306-30315.
Lee and Ro, Neuroscience (2007) 146:375-383.
Lee et al., J Physiol (1999) 517(Pt. 3):709-720.
Leinweber et al., J Biol Chem (2000) 275(51):40329-40336.
Li et al., Br J Pharmacol (2005) 144(3):301-307.
Lidington et at., Am J Physiol Cell Physiol (2005) 289(6):C1437-C1447.
Liedtke et al., J Biol Chem (2002) 277(25):22925-22933.
Liron et al., J Mol Cell Cardiol (2007) 42(4):835-841 [DOI:10.1016/j.yjmcc.2007.01.007].
Liu et al., J Mol Cell Cardiol (1999) 31(10):1937-1948.
Ludwig et al., Anesthesiology (2004) 100(3):532-539.
Mackay and Mochly-Rosen, Cardiovasc Res (2001) 50(1):65-74.
Mackay and Mochly-Rosen, J Mol Cell Cardiol (2000) 32(8):1585-1588.
Mackay and Mochly-Rosen, J Biol Chem (1999) 274(10):6272-6279.
Mackay and Mochly-Rosen, J Mol Cell Cardiol (2001) 33(7):1301-1307.
Malhotra et al., Am J Physiol Heart Circ Physiol (2005) 289(4):H1343-H1350.
Mamidipudi et al., Biochem Biophys Res Commun (2007) 352(2):423-430.
Mangat et al., Am J Physiol Heart Circ Physiol (2006) 291:H854-H860.
Marin et al., Cell Signal (2006) 18(8):1279-1286.
Marinovic et al., Anesthesiology (2005) 103(3):540-547.
Mayne and Murray, J Biol Chem (1998) 273(37):24115-24121.
McNair et al., Hypertension (2004) 43(4):897-904.
Mihailidou et al., Endocrinology (2004) 145(2):773-780.
Miller et al., Oncogene (2004) 1-5.
Miyamae et al., PNAS USA (1998) 95(14):8262-8267.
Mochly-Rosen, Science (1995) 268(5208):247-251.
Mochly-Rosen and Gordon, Faseb J. (1998) 12(1):35-42.
Mochly-Rosen and Kauvar, Semin Immunol (2000) 12(1):55-61.
Mochly-Rosen and Kauvar, Adv Pharmacol (1998) 44:91-145.
Mochly-Rosen et al., Adv Enzyme Regul (2001) 41:87-97.
Mochly-Rosen et al., Biochem Soc Trans (1995) 23(3):596-600.
Mochly-Rosen et al., Biochemistry (1992) 31(35):8120-8124.
Mochly-Rosen et al., Cell Regul (1990) 1(9):693-706.
Mochly-Rosen et al., Circ Res (2000) 86(11):1173-1179.
Mochly-Rosen et al., J Biol Chem (1991) 266(23):14866-14868.
Mochly-Rosen et al., PNAS USA (1991) 88(9):3997-4000.
Moon et al., Eur J Pharmacol (2004) 506(1):27-35.
Murriel and Mochly-Rosen, Arch Biochem Biophys (2003) 420(2):246-254.
Murriel et al., J Biol Chem (2004) 279(46):47985-47991.
Nelson et al., J Biol Chem (2003) 278(7):4552-4560.
Newton and Messing, Pharmacol Ther (2006) 109:227-237.
Newton and Ron, Pharmacol Res (2007) 55(6):570-577 [DOI:10.1016/j.phrs.2007.04.008].
Nguyen et al., Euro J Neurosci (2005) 21:905-913.
Novalija et al., Anesthesiology (2003) 99:421-428.
Ogbi and Johnson, Biochem J (2006) 393(Pt: 1):191-199.
Okochi et al., EMBO J (2005) 24:2127-2137.
Parada et al., Neuroscience (2003) 120(1):219-226.
Parada et al., Pain (2005) 113(1-2):185-190.
Pardo et al., EMBO Journal (2006) 25(13):3078-3088.
Park et al., Biochem Biophys Res Commun (2006) 341(3):728-735.
Perez-Pinson et al., Antioxid Redox Signal (2005) 7(9-10):1150-1157.
Perry et al., Am J Physiol Renal Physiol 290(2):F417-F427, (2006).
Pierre et al., Cardiovasc Res (2007) 73:488-496.
Pitchford et al., J Neurosci (1992) 12(11):4540-4544.
Poole and Furness, Am J Physiol (2006) 292:G887-G898[DOI:10.1152/ajpgi.00222.2006].
Poole et al., Gastroenterology (2007) [DOI:10.1053/j.gastro.2007.07.002].
Qi et al., J Biol Chem (2007) 282(45):33052-33063 [DOI:10.1074/jbc.M707233200].
Raval et al., Brain Res (2007) 1184:345-353 [Pre-print].
Raval et al., Brain Res (2007) 1184:345-353 [DOI:10.10164.brainres.2007.09.073].
Raval et al., J Cereb Blood Flow Metab (2005) 25(6):730-741.
Raval et al., J Neurosci (2003) 23(2):384-391.
Ridge et al., J Biol Chem (2005) 280(34):30400-30405.
Ridge et al., Mol Biol Cell (2002) 13(4):1381-1389.
Robia et al., Am J Physiol Heart Circ Physiol (2005) 289(5):H1941-H1950.
Rodriguez et al., Biochemistry (1999) 38(42):13787-13794.
Rodriguez et al., FEBS Lett (1999) 454(3):240-246.
Ron and Mochly-Rosen, J Biol Chem (1994) 269(34):21395-21398.
Ron and Mochly-Rosen, PNAS USA (1995) 92(2):492-496.
Ron et al., J Biol Chem (1995) 270(41):24180-24187.
Ron et al., PNAS USA (1994) 91(3):839-843.
Satoh et al., Am J Physiol Gastrointest Liver Physiol (2004) 287(3):G582-G591.
Satoh et al., Am J Physiol Gastrointest Liver Physiol (2006) [DOI:10.1152/AJPG1.00579.2005].
Satoh et al., Gastroenterology (2005) 129(2):639-651.
Schechtman and Mochly-Rosen, Methods Enzymol (2002) 345:470-489.
Schechtman and Mochly-Rosen, Oncogene (2001) 20(44):6339-6347.
Schechtman et al., J Biol Chem (2004) 279(16):15831-15840.
Schechtman et al., Methods Mol Biol (2003) 233:351-357.
Schechtman et al., Methods Mol Biol (2003) 233:345-350.
Schmitz-Peiffer et al., Cell Metab (2007) 6(4):320-328.
Shao et al., Am J Physiol Heart Circ Physiol (2007) 292:H1995-H2003.
Shizukuda and Buttrick, J Mol Cell Cardiol (2001) 33(10):1791-1803.
Shizukuda et al., Am J Physiol Heart Circ Physiol (2002) 282(5):H1625-H1634.
Shumilla et al., Anesth Analg (2004) 99(1):82-84.
Shumilla et al., J Pain (2005) 6(8):535-549.
Silva et at., Am J Physiol Gastrointest Liver Physiol (2004) 286(6):G1024-G1031.
Simon et al., Curr Biol (1993) 3(12):813-821.
Simon et al., Proc Bio Sci (1991) 243(1307):165-171.
Smith and Mochly-Rosen, Biochem Biophys Res Commun (1992) 188(3):1235-1240.
Smith et al., J Biol Chem (1996) 271(28):16753-16757.
Smith et al., Pain (2007) Pain 127(1-2):129-139.

Souroujon and Mochly-Rosen, Nat Biotechnol (1998) 16(10):919-924.
Souroujon et al., J Biol Chem (2004) 279(17):17617-17624.
Stebbins and Mochly-Rosen, J Biol Chem (2001) 276(32):29644-29650.
Steinberg et al., J Biol Chem (2007) 282(44):32288-32297.
Summer et al., Burns (2007) [DOI:10.1016/j.burns.2007.02.007].
Summer et al., J Pain (2006) 7(12):884-891 [DOI:10.1016.j.jpain.2006.04.009].
Suzuki et al., J Biol Chem (2008) 283(6):3574-3583 [DOI:10.1074/jbc.M709141200].
Sweitzer et al., J Pharmacol Exp Ther (2004) 309(2):616-625.
Sweitzer et al., Pain (2004) 110(1-2):281-289.
Szabo et al., Alcohol Clin Exp Res (2005) 29(9):1749-1752.
Tabakoff et al., J Biomed Sci (2001) 8(1):44-51.
Tanaka et al., Circulation (2004) 110(Suppl 11):II194-II199.
Tanaka et al., J Thorac Cardiovasc Surg (2005) 129(5):1160-1167.
Taneja et al., Am J Physiol Cell Physiol (2004) 287(2):C548-0557.
Tepperman et al., Eur J Pharmacol (2005) 518(1):1-9.
Toda et al., British J of Pharmacol (2007) 1-11.
Vallentin and Mochly-Rosen, J Biol Chem (2007) 282(3):1650-1657.
Van Kolen et al., J Neurochem (2007) [DOI:10.11/j.1471-4159.2007.04986.x].
Velazquez et al., Pharmacol Res (2007) 55(6):578-589 [DOI:10.1016/j.phrs.2007.04.006].

Wang et al., J Biol Chem (2005) 280(21):20325-20330.
Wang et al., J Pharmacol Exp Ther (2001) 299(2):603-610.
Wang et al., Neuropharmacology (2004) 47(1):136-145.
Way et al., Trends Pharmacol Sci (2000) 21(5):181-187.
Webb et al., Cell Mol Life Sci (2003) 60(7):1504-1512.
Xiao et al., Am J Physiol Cell Physiol (2001) 281(5):C1477-C1486.
Xiao et al., Biochem Biophys Res Commun (2003) 306(4)1019-1025.
Yamamoto et al., Neurosci (2006) 137:949-960.
Yedovitzky et al., J Biol Chem (1997) 272(3):1417-1420.
Yamamura et al., Am J Physiol Heart Circ Physiol (2005) 289(6):H2484-H2490.
Zatta et al., Cardiovasc Res (2006) 70(2):315-324 [DOI:10.1016/j.cardiores.2005.11.030].
Zhang et al., Circ Res (1997) 80(5):720-729.
Zhang et al., Invest Ophthamol Vis Sci (2006) 47(9):3989-4000.
Zhang et al., J Neurosci (2007) 27(44):12067-12077.
Zhang et al., J Pharmacol Exp Ther (2002) 301(3):1012-1019.
Zhong et al., Am J Physiol Cell Physiol (2002) 283:C1627-C1636.
Zhou et al., Am J Physiol Heart Circ Physiol 12002) 283(1):H165-H174.
Zhou et al., J Invest Dermatol (1996) 107(2):248-252.

* cited by examiner

US 8,017,583 B2

SEQUENCE LISTING

<160> NUMBER OF SEQ ID NOS: 62

<210> SEQ ID NO 1
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(6)
<223> OTHER INFORMATION: Gamma PKC inhibitory peptide

<400> SEQUENCE: 1

Arg Leu Val Leu Ala Ser
 1               5

<210> SEQ ID NO 2
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(7)
<223> OTHER INFORMATION: Gamma PKC inhibitory peptide

<400> SEQUENCE: 2

Cys Arg Leu Val Leu Ala Ser
 1               5

<210> SEQ ID NO 3
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(7)
<223> OTHER INFORMATION: Gamma PKC inhibitory peptide

<400> SEQUENCE: 3

Arg Leu Val Leu Ala Ser Cys
 1               5

<210> SEQ ID NO 4
<211> LENGTH: 12
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(12)
<223> OTHER INFORMATION: Gamma PKC inhibitory peptide

<400> SEQUENCE: 4

Cys Tyr Gly Arg Lys Lys Arg Arg Gln Arg Arg Arg
 1               5                  10

<210> SEQ ID NO 5
<211> LENGTH: 12
<212> TYPE: PRT
<213> ORGANISM: Artificial Sequence
<220> FEATURE:
<223> OTHER INFORMATION: Synthetic construct
<220> FEATURE:

```
<221> NAME/KEY: DOMAIN
<222> LOCATION: (1)...(12)
<223> OTHER INFORMATION: Gamma PKC inhibitory peptide

<400> SEQUENCE: 5

Tyr Gly Arg Lys Lys Arg Arg Gln Arg Arg Cys
1               5                   10

<210> SEQ ID NO 6
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(7)
<223> OTHER INFORMATION: Gamma PKC inhibitory peptide
<220> FEATURE:
<221> NAME/KEY: SITE
<222> LOCATION: 1
<223> OTHER INFORMATION: Xaa = homocysteine

<400> SEQUENCE: 6

Xaa Arg Leu Val Leu Ala Ser
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(7)
<223> OTHER INFORMATION: Gamma PKC inhibitory peptide
<220> FEATURE:
<221> NAME/KEY: SITE
<222> LOCATION: 7
<223> OTHER INFORMATION: Xaa = homocysteine

<400> SEQUENCE: 7

Arg Leu Val Leu Ala Ser Xaa
1               5

<210> SEQ ID NO 8
<211> LENGTH: 12
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(12)
<223> OTHER INFORMATION: Gamma PKC inhibitory peptide
<220> FEATURE:
<221> NAME/KEY: SITE
<222> LOCATION: 1
<223> OTHER INFORMATION: Xaa = homocysteine

<400> SEQUENCE: 8

Xaa Tyr Gly Arg Lys Lys Arg Arg Gln Arg Arg
1               5                   10

<210> SEQ ID NO 9
<211> LENGTH: 12
<212> TYPE: PRT
<213> ORGANISM: Artificial Sequence
<220> FEATURE:
<223> OTHER INFORMATION: Synthetic construct
<220> FEATURE:
```

```
-continued

<221> NAME/KEY: DOMAIN
<222> LOCATION: (1)...(12)
<223> OTHER INFORMATION: Gamma PKC inhibitory peptide
<220> FEATURE:
<221> NAME/KEY: SITE
<222> LOCATION: 12
<223> OTHER INFORMATION: Xaa = homocysteine

<400> SEQUENCE: 9

Tyr Gly Arg Lys Lys Arg Arg Gln Arg Arg Xaa
1               5                   10

<210> SEQ ID NO 10
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(7)
<223> OTHER INFORMATION: Gamma PKC inhibitory peptide
<220> FEATURE:
<221> NAME/KEY: SITE
<222> LOCATION: 1
<223> OTHER INFORMATION: Xaa = mercaptopropionic acid

<400> SEQUENCE: 10

Xaa Arg Leu Val Leu Ala Ser
1               5

<210> SEQ ID NO 11
<211> LENGTH: 12
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(12)
<223> OTHER INFORMATION: Gamma PKC inhibitory peptide
<220> FEATURE:
<221> NAME/KEY: SITE
<222> LOCATION: 1
<223> OTHER INFORMATION: Xaa = mercaptopropionic acid

<400> SEQUENCE: 11

Xaa Tyr Gly Arg Lys Lys Arg Arg Gln Arg Arg Arg
1               5                   10

<210> SEQ ID NO 12
<211> LENGTH: 12
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(12)
<223> OTHER INFORMATION: Gamma PKC inhibitory peptide
<220> FEATURE:
<221> NAME/KEY: SITE
<222> LOCATION: 1
<223> OTHER INFORMATION: Xaa = mercaptobutyric acid

<400> SEQUENCE: 12

Xaa Tyr Gly Arg Lys Lys Arg Arg Gln Arg Arg Arg
1               5                   10

<210> SEQ ID NO 13
<211> LENGTH: 8
<212> TYPE: PRT
```

```
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(8)
<223> OTHER INFORMATION: Gamma PKC inhibitory peptide

<400> SEQUENCE: 13

Ala Cys Arg Leu Val Leu Ala Ser
 1               5

<210> SEQ ID NO 14
<211> LENGTH: 13
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(13)
<223> OTHER INFORMATION: Gamma PKC inhibitory peptide

<400> SEQUENCE: 14

Ala Cys Tyr Gly Arg Lys Lys Arg Arg Gln Arg Arg Arg
 1               5                  10

<210> SEQ ID NO 15
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(7)
<223> OTHER INFORMATION: Epsilon PKC inhibitory peptide

<400> SEQUENCE: 15

Asn Gly Leu Leu Lys Ile Lys
 1               5

<210> SEQ ID NO 16
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(11)
<223> OTHER INFORMATION: Epsilon PKC inhibitory peptide

<400> SEQUENCE: 16

Leu Ala Val Phe His Asp Ala Pro Ile Gly Tyr
 1               5                  10

<210> SEQ ID NO 17
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(9)
<223> OTHER INFORMATION: Epsilon PKC inhibitory peptide

<400> SEQUENCE: 17

Asp Asp Phe Val Ala Asn Cys Thr Ile
 1               5
```

-continued

```
<210> SEQ ID NO 18
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(10)
<223> OTHER INFORMATION: Epsilon PKC inhibitory peptide

<400> SEQUENCE: 18

Trp Ile Asp Leu Glu Pro Glu Gly Arg Val
 1               5                  10

<210> SEQ ID NO 19
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(10)
<223> OTHER INFORMATION: Epsilon PKC inhibitory peptide

<400> SEQUENCE: 19

His Ala Val Gly Pro Arg Pro Gln Thr Phe
 1               5                  10

<210> SEQ ID NO 20
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(8)
<223> OTHER INFORMATION: Epsilon PKC inhibitory peptide

<400> SEQUENCE: 20

Asn Gly Ser Arg His Phe Glu Asp
 1               5

<210> SEQ ID NO 21
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(8)
<223> OTHER INFORMATION: Epsilon PKC inhibitory peptide

<400> SEQUENCE: 21

His Asp Ala Pro Ile Gly Asp Tyr
 1               5

<210> SEQ ID NO 22
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(6)
<223> OTHER INFORMATION: Epsilon PKC inhibitory peptide
```

```
<400> SEQUENCE: 22

His Asp Ala Pro Ile Gly
1               5

<210> SEQ ID NO 23
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(7)
<223> OTHER INFORMATION: Gamma PKC inhibitory peptide
<220> FEATURE:
<221> NAME/KEY: SITE
<222> LOCATION: 1
<223> OTHER INFORMATION: Xaa = mercaptobutyric acid

<400> SEQUENCE: 23

Xaa Arg Leu Val Leu Ala Ser
1               5

<210> SEQ ID NO 24
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(7)
<223> OTHER INFORMATION: Gamma PKC inhibitory peptide
<220> FEATURE:
<221> NAME/KEY: SITE
<222> LOCATION: 1
<223> OTHER INFORMATION: Xaa = mercaptoacetic acid

<400> SEQUENCE: 24

Xaa Arg Leu Val Leu Ala Ser
1               5

<210> SEQ ID NO 25
<211> LENGTH: 12
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(12)
<223> OTHER INFORMATION: Gamma PKC inhibitory peptide
<220> FEATURE:
<221> NAME/KEY: SITE
<222> LOCATION: 1
<223> OTHER INFORMATION: Xaa = mercaptoacetic acid

<400> SEQUENCE: 25

Xaa Tyr Gly Arg Lys Lys Arg Arg Gln Arg Arg Arg
1               5                   10

<210> SEQ ID NO 26
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(8)
<223> OTHER INFORMATION: Epsilon PKC inhibitory peptide
```

```
<400> SEQUENCE: 26

His Asp Ala Ala Ile Gly Tyr Asp
1               5

<210> SEQ ID NO 27
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(8)
<223> OTHER INFORMATION: Epsilon PKC inhibitory peptide

<400> SEQUENCE: 27

His Asp Ala Pro Ile Pro Tyr Asp
1               5

<210> SEQ ID NO 28
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(8)
<223> OTHER INFORMATION: Epsilon PKC inhibitory peptide

<400> SEQUENCE: 28

His Asn Ala Pro Ile Gly Tyr Asp
1               5

<210> SEQ ID NO 29
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(8)
<223> OTHER INFORMATION: Epsilon PKC inhibitory peptide

<400> SEQUENCE: 29

His Ala Ala Pro Ile Gly Tyr Asp
1               5

<210> SEQ ID NO 30
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(8)
<223> OTHER INFORMATION: Epsilon PKC inhibitory peptide

<400> SEQUENCE: 30

Ala Asp Ala Pro Ile Gly Tyr Asp
1               5

<210> SEQ ID NO 31
<211> LENGTH: 8
<212> TYPE: PRT
<213> ORGANISM: Artificial Sequence
<220> FEATURE:
```

```
<223> OTHER INFORMATION: Synthetic construct
<220> FEATURE:
<221> NAME/KEY: DOMAIN
<222> LOCATION: (1)...(8)
<223> OTHER INFORMATION: Epsilon PKC inhibitory peptide

<400> SEQUENCE: 31

His Asp Ala Pro Ala Gly Tyr Asp
 1               5

<210> SEQ ID NO 32
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(8)
<223> OTHER INFORMATION: Epsilon PKC inhibitory peptide

<400> SEQUENCE: 32

His Asp Ala Pro Ile Gly Ala Asp
 1               5

<210> SEQ ID NO 33
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(8)
<223> OTHER INFORMATION: Epsilon PKC inhibitory peptide

<400> SEQUENCE: 33

His Asp Ala Pro Ile Ala Tyr Asp
 1               5

<210> SEQ ID NO 34
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(8)
<223> OTHER INFORMATION: Epsilon PKC inhibitory peptide

<400> SEQUENCE: 34

His Asp Ala Pro Ile Gly Tyr Ala
 1               5

<210> SEQ ID NO 35
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(9)
<223> OTHER INFORMATION: Epsilon PKC inhibitory peptide

<400> SEQUENCE: 35

Ser Ser Pro Ser Glu Glu Asp Arg Ser
 1               5
```

```
<210> SEQ ID NO 36
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(8)
<223> OTHER INFORMATION: Epsilon PKC inhibitory peptide

<400> SEQUENCE: 36

Pro Cys Asp Gln Glu Ile Lys Glu
 1               5

<210> SEQ ID NO 37
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(9)
<223> OTHER INFORMATION: Epsilon PKC inhibitory peptide

<400> SEQUENCE: 37

Glu Asn Asn Ile Arg Lys Ala Leu Ser
 1               5

<210> SEQ ID NO 38
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(8)
<223> OTHER INFORMATION: Epsilon PKC inhibitory peptide

<400> SEQUENCE: 38

Gly Glu Val Arg Gln Gly Gln Ala
 1               5

<210> SEQ ID NO 39
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(6)
<223> OTHER INFORMATION: Epsilon PKC inhibitory peptide

<400> SEQUENCE: 39

Glu Ala Ile Val Lys Gln
 1               5

<210> SEQ ID NO 40
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(7)
<223> OTHER INFORMATION: Epsilon PKC inhibitory peptide

<400> SEQUENCE: 40
```

```
Ile Lys Thr Lys Arg Asp Val
1               5
```

<210> SEQ ID NO 41
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(7)
<223> OTHER INFORMATION: Epsilon PKC inhibitory peptide

<400> SEQUENCE: 41

```
Ile Lys Thr Lys Arg Leu Ile
1               5
```

<210> SEQ ID NO 42
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(7)
<223> OTHER INFORMATION: Epsilon PKC inhibitory peptide

<400> SEQUENCE: 42

```
Cys Glu Ala Ile Val Lys Gln
1               5
```

<210> SEQ ID NO 43
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(10)
<223> OTHER INFORMATION: Epsilon PKC inhibitory peptide

<400> SEQUENCE: 43

```
Thr Lys Arg Asp Val Asn Asn Phe Asp Gln
1               5                   10
```

<210> SEQ ID NO 44
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(9)
<223> OTHER INFORMATION: Cargo peptide

<400> SEQUENCE: 44

```
Cys Glu Ala Val Ser Leu Lys Pro Thr
1               5
```

<210> SEQ ID NO 45
<211> LENGTH: 9
<212> TYPE: PRT
<213> ORGANISM: Artificial Sequence
<220> FEATURE:
<223> OTHER INFORMATION: Synthetic construct
<220> FEATURE:

```
<221> NAME/KEY: DOMAIN
<222> LOCATION: (1)...(9)
<223> OTHER INFORMATION: Cargo peptide
<220> FEATURE:
<221> NAME/KEY: SITE
<222> LOCATION: 1
<223> OTHER INFORMATION: Xaa = acetylated cysteine
<220> FEATURE:
<221> NAME/KEY: SITE
<222> LOCATION: 9
<223> OTHER INFORMATION: Xaa = amide-modified threonine

<400> SEQUENCE: 45

Xaa Glu Ala Val Ser Leu Lys Pro Xaa
 1               5

<210> SEQ ID NO 46
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(10)
<223> OTHER INFORMATION: Cargo peptide
<220> FEATURE:
<221> NAME/KEY: SITE
<222> LOCATION: 1
<223> OTHER INFORMATION: Xaa = acetylated cysteine
<220> FEATURE:
<221> NAME/KEY: SITE
<222> LOCATION: 10
<223> OTHER INFORMATION: Xaa = amide-modified arginine

<400> SEQUENCE: 46

Xaa Leu Lys Pro Thr Ala Trp Ser Leu Xaa
 1               5                  10

<210> SEQ ID NO 47
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(14)
<223> OTHER INFORMATION: Cargo peptide
<220> FEATURE:
<221> NAME/KEY: SITE
<222> LOCATION: 1
<223> OTHER INFORMATION: Xaa = acetylated cysteine

<400> SEQUENCE: 47

Xaa Glu Ala Val Ser Leu Lys Pro Thr Ala Trp Ser Leu Arg
 1               5                  10

<210> SEQ ID NO 48
<211> LENGTH: 21
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(21)
<223> OTHER INFORMATION: Cargo peptide
<220> FEATURE:
<221> NAME/KEY: SITE
<222> LOCATION: (11)...(21)
<223> OTHER INFORMATION: Residues 47-57 of HIV Tat
<220> FEATURE:
<221> NAME/KEY: SITE
```

```
<222> LOCATION: 21
<223> OTHER INFORMATION: Xaa = amide-modified arginine

<400> SEQUENCE: 48

Glu Ala Val Ser Leu Lys Pro Thr Gly Gly Tyr Gly Arg Lys Lys
 1               5                  10                  15

Arg Gln Arg Arg Xaa
            20

<210> SEQ ID NO 49
<211> LENGTH: 12
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(12)
<223> OTHER INFORMATION: Cargo peptide
<220> FEATURE:
<221> NAME/KEY: SITE
<222> LOCATION: 1
<223> OTHER INFORMATION: Xaa = acetylated glutamic acid

<400> SEQUENCE: 49

Xaa Ala Val Ser Leu Lys Pro Thr Gly Gly Lys Cys
 1               5                  10

<210> SEQ ID NO 50
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(9)
<223> OTHER INFORMATION: Cargo peptide

<400> SEQUENCE: 50

Thr Pro Lys Leu Ser Val Ala Glu Cys
 1               5

<210> SEQ ID NO 51
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(9)
<223> OTHER INFORMATION: Cargo peptide

<400> SEQUENCE: 51

Cys Glu Ala Val Ser Leu Lys Pro Thr
 1               5

<210> SEQ ID NO 52
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(9)
<223> OTHER INFORMATION: Cargo peptide
<220> FEATURE:
<221> NAME/KEY: SITE
<222> LOCATION: 1
```

```
<223> OTHER INFORMATION: Xaa = acetylated cysteine
<220> FEATURE:
<221> NAME/KEY: SITE
<222> LOCATION: 9
<223> OTHER INFORMATION: Xaa = amide-modified threonine

<400> SEQUENCE: 52

Xaa Glu Ala Val Ser Leu Lys Pro Xaa
 1               5

<210> SEQ ID NO 53
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(9)
<223> OTHER INFORMATION: Cargo peptide
<220> FEATURE:
<221> NAME/KEY: SITE
<222> LOCATION: 1
<223> OTHER INFORMATION: Xaa = acetylated homocysteine
<220> FEATURE:
<221> NAME/KEY: SITE
<222> LOCATION: 9
<223> OTHER INFORMATION: Xaa = amide-modified threonine

<400> SEQUENCE: 53

Xaa Glu Ala Val Ser Leu Lys Pro Xaa
 1               5

<210> SEQ ID NO 54
<211> LENGTH: 21
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(21)
<223> OTHER INFORMATION: Cargo peptide
<220> FEATURE:
<221> NAME/KEY: SITE
<222> LOCATION: 1
<223> OTHER INFORMATION: Xaa = acetylated glutamic acid
<220> FEATURE:
<221> NAME/KEY: SITE
<222> LOCATION: (11)...(21)
<223> OTHER INFORMATION: Residues 47-57 of HIV Tat
<220> FEATURE:
<221> NAME/KEY: SITE
<222> LOCATION: 21
<223> OTHER INFORMATION: Xaa = amide-modified arginine

<400> SEQUENCE: 54

Xaa Ala Val Ser Leu Lys Pro Thr Gly Gly Tyr Gly Arg Lys Arg
 1               5                  10                  15

Arg Gln Arg Arg Xaa
             20

<210> SEQ ID NO 55
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(10)
<223> OTHER INFORMATION: Epsilon PKC inhibitory peptide
```

-continued

```
<400> SEQUENCE: 55

His Cys Glu Ala Val Ser Leu Lys Pro Thr
1               5                   10

<210> SEQ ID NO 56
<211> LENGTH: 12
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(12)
<223> OTHER INFORMATION: HIV Tat-derived transporter peptide
<220> FEATURE:
<221> NAME/KEY: SITE
<222> LOCATION: 1
<223> OTHER INFORMATION: Xaa = acetylated cysteine

<400> SEQUENCE: 56

Xaa Tyr Gly Arg Lys Lys Arg Arg Gln Arg Arg Arg
1               5                   10

<210> SEQ ID NO 57
<211> LENGTH: 21
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(21)
<223> OTHER INFORMATION: Epsilon inhibitory peptide
<220> FEATURE:
<221> NAME/KEY: SITE
<222> LOCATION: 1
<223> OTHER INFORMATION: Xaa = acetylated glutamic acid
<220> FEATURE:
<221> NAME/KEY: SITE
<222> LOCATION: 21
<223> OTHER INFORMATION: Xaa = amide-modified arginine

<400> SEQUENCE: 57

Xaa Ala Val Ser Leu Lys Pro Thr Gly Gly Tyr Gly Arg Lys Lys Arg
1               5                   10                  15

Arg Gln Arg Arg Xaa
            20

<210> SEQ ID NO 58
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(8)
<223> OTHER INFORMATION: Cargo peptide

<400> SEQUENCE: 58

Glu Ala Val Ser Leu Lys Pro Thr
1               5

<210> SEQ ID NO 59
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
```

```
<222> LOCATION: (1)...(11)
<223> OTHER INFORMATION: Intracellular carrier peptide

<400> SEQUENCE: 59

Tyr Gly Arg Lys Lys Arg Arg Gln Arg Arg Arg
1               5                   10

<210> SEQ ID NO 60
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(9)
<223> OTHER INFORMATION: Inhibitory peptide

<400> SEQUENCE: 60

Glu Ala Val Ser Leu Lys Pro Thr Cys
1               5

<210> SEQ ID NO 61
<211> LENGTH: 12
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(12)
<223> OTHER INFORMATION: Tat peptide
<220> FEATURE:
<221> NAME/KEY: SITE
<222> LOCATION: 1
<223> OTHER INFORMATION: Xaa = acetylated tyrosine
<220> FEATURE:
<221> NAME/KEY: SITE
<222> LOCATION: 12
<223> OTHER INFORMATION: Xaa = amide-modified cystine

<400> SEQUENCE: 61

Xaa Gly Arg Lys Lys Arg Arg Gln Arg Arg Arg Xaa
1               5                   10

<210> SEQ ID NO 62
<211> LENGTH: 21
<212> TYPE: PRT
<213> ORGANISM: Artificial Sequence
<220> FEATURE:
<223> OTHER INFORMATION: Synthetic construct
<220> FEATURE:
<221> NAME/KEY: DOMAIN
<222> LOCATION: (1)...(21)
<223> OTHER INFORMATION: Linear therapeutic peptide
<220> FEATURE:
<221> NAME/KEY: SITE
<222> LOCATION: 21
<223> OTHER INFORMATION: Xaa = amide-modified arginine

<400> SEQUENCE: 62

Glu Ala Val Ser Leu Lys Pro Thr Gly Gly Tyr Gly Arg Lys Lys Arg
1               5                   10                  15

Arg Gln Arg Arg Xaa
            20
```

METHODS OF USE OF EPSILON INHIBITOR COMPOUNDS FOR THE ATTENUATION OF PAIN

RELATED APPLICATIONS

This application claims the benefit of priority of U.S. Provisional Application Nos. 60/881,396, 60/903,684, 60/917,876, and 60/977,332, all of which are incorporated by reference in their entirety.

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
|---|---|---|
| 578422002100Seqlist.txt | Oct. 10, 2008 | 19,886 bytes |

TECHNICAL FIELD

This present disclosure relates to the development and use of compound(s) that modulate different types of pain, and where compounds that may have overlapping and/or non-overlapping mechanisms of biochemical activity are incorporated into a single compound entity (so-called "Hybrid" compounds or peptides) for the treatment of pain and related conditions. Wherein the compounds comprise one or more epsilon PKC (εPKC) inhibitory peptides coupled to at least one carrier moiety and where the inhibitory peptides, the carrier moiety, or both have been modified from a prototype sequence to increase the stability, potency, or both of the resulting compound. The εPKC inhibitory peptides may also be coupled to one or more modulatory peptides with specific activity against one or more of the other PKC isozymes, including PKC alpha, beta, delta, gamma, theta or eta. The benefits of a hybrid compound or peptide over an isozyme-specific PKC modulator would be to provide a broader spectrum of activities to modulate various types of pain and/or provide greater potency and/or greater safety for a pain modulating compound and/or to provide dual therapeutic activities to alleviate multiple aspects of a disease condition (e.g., combining pain-reducing activity with an anti-inflammatory activity).

BACKGROUND

Pain is an uncomfortable sensation caused by inflammation, nerve injury, or overly-sensitive tissue reacting to mechanical, thermal or chemical stimuli. It is a major health problem: every year many work days are lost due to pain-related conditions. Among a wide variety of pains, neuropathic pain is a disease arising from nerve damage and affects >1 million Americans. This condition arises from a variety of causes including diabetes, herpes zoster infection (chicken pox/shingles), traumatic nerve injury, cancer, or treatment of cancer with chemotherapeutic agents. Inflammatory pain is another kind of pain that constitutes the single largest category due to its multiple etiologies. The search for new analgesic therapy is an area of great interest to the medical community (Reichling & Levine, 1999) because it is associated with other local or systemic diseases, such as auto-immune disorder like rheumatoid arthritis and because it is chronic and thus causes prolonged suffering.

Most of the current pain treatment use remedies of systemically-administered drugs, such as non-steroidal anti-inflammatory drugs (NSAIDS) or opioids. Many of these drugs cause systemic sides effects ranging from the increase in heart risk to addiction. There are only a few pain remedies that use local routes of administration, such as capsaicin cream, which does not work on all kinds of pain and causes local irritation (burning sensation, skin pain, skin inflammation, etc).

Protein kinase C ("PKC") is a key enzyme in signal transduction involved in a variety of cellular functions, including cell growth, regulation of gene expression, and ion channel activity. The PKC family of isozymes includes at least 11 different protein kinases that can be divided into at least three subfamilies based on their homology and sensitivity to activators. The families are the classical, the novel, and the atypical subfamilies. Each isozyme includes a number of homologous ("conserved" or "C") domains interspersed with isozyme-unique ("variable" or "V") domains. Epsilon PKC is a member of the "novel" subfamily, along with δ, η and θPKC. Members of this subfamily typically lack the C2 homologous domain and do not require calcium for activation. Individual isozymes of PKC have been implicated in the mechanisms of various disease states. Epsilon PKC inhibitory peptides derived from εPKC have been generated and shown to impact nociception. For example, see U.S. Pat. Nos. 6,376,467 and 6,686,334.

One problem with this approach is that the "naked" termini of the excised fragments are different from their context in the protein, revealing free amine and carboxyl groups at the points where the fragment attaches to the remainder of the protein. These extraneous moieties may render the peptide more susceptible to proteases. As a result of these liabilities the potency of the peptide may be less than desired and the in vivo half-life may be significantly shortened.

A second area of the prior art makes use of a similar strategy, wherein "carrier" peptides are designed as fragments of HIV-Tat and other proteins. These peptide fragments mimic the ability of the parent protein to cross cell membranes. Of particular interest is the property that "cargo" peptides can be attached to these carrier peptides such that both cargo and carrier peptides are carried into the cell by these carrier peptide fragments.

Recognizing that the carrier peptides are fragments, similar deficiencies may apply as noted above for the cargo peptides. That is, the exposed termini may confer undesirable properties including protease susceptibility.

Prior art cargo/carrier peptide constructs have made use of a Cys-Cys disulfide bond between cargo and carrier, which can be cleaved by a number of agents, such as glutathione reduction when the peptides enter cells. This property has been thought to be important for biological activity, since the physical separation of cargo and carrier allows the two moieties to exert their independent effects within the cell. However, this hypothesis has not been convincingly tested, and non-cleavable analogs may in fact have good activity. Further, the disulfide bond is cumbersome to assemble, and prone to chemical degradation.

The design of certain prior art cargo/carrier peptides is based on a contiguous sequence of amino acids from the protein. However, the optimal length of the peptide has not yet been well defined, being based on sequence comparison analysis and theoretical prediction of the desired sequence rather than on an empirical basis of analog testing. Thus, increased potency may be anticipated from analogs of the previously described cargo peptides which contain additional residues corresponding to the εPKC domain from which the have been derived.

BRIEF DESCRIPTION OF THE DRAWINGS

FIG. 31: KAI-1678 Plasma Concentrations in Dogs Dosed by Subcutaneous Infusion over 5 Days. Plasma concentrations of KAI-1678 in dogs dosed by subcutaneous infusion at 3, 8 and 25 mg/kg/day. Note that samples were recovered on Day 1 for the first four hours and on Day 6 at the end of infusion (EOI), with no sampling in the period between.

DISCLOSURE OF THE INVENTION

Figure 1:
FIG. 1 shows a schematic representation of a modified εPKC inhibitory peptide (KP-1634) (SEQ ID NOS:49, 54, 56).

The disclosure herein relates to modified εPKC inhibitory peptides, methods of generating such peptides, and method for using εPKC inhibitory peptides for the treatment of pain. The disclosed invention also relates to the role of locally-administered protein kinase C epsilon (εPKC) inhibitors play in suppressing pain perception. Methods to suppress pain systemically with an εPKC inhibitor, particularly through mechanisms that require affecting primary afferent function and modulation of the sympathetic nervous system. Hybrid peptides comprising an εPKC-specific inhibitor and another PKC modulatory peptide are also contemplated as falling within the scope of the presently disclosed invention. Any PKC modulatory peptide can be used to prepare the hybrid construct so that the activity of more than one isozyme-specific PKC modulator is combined into a single hybrid compound/peptide. Other aspects and embodiments will be apparent to those skilled in the art form the following detailed description.

DESCRIPTION OF THE INVENTION

The presently described invention relates to modified peptides which inhibit the epsilon protein kinase C (εPKC) isozyme and are coupled to another isozyme-specific PKC modulator. Typically, the εPKC inhibitory peptides discussed herein are coupled to a carrier moiety to facilitate transport of the inhibitory peptide to a target cell. The cargo inhibitory peptide, the carrier peptide, or both can be modified relative to a prototype control to increase the stability of the resulting cargo/carrier peptide constructs. The disclosed modified εPKC peptides are useful in preventing, reversing and otherwise treating various types of pain, such as acute pain, chronic pain, neuropathic pain and inflammatory pain. The εPKC inhibitory proteins can also be used to construct a hybrid peptide construct, which comprises one or more isozyme-specific PKC modulatory peptides with activity against other PKC isozymes.

DEFINITIONS

As used in the present specification, the following words and phrases are generally intended to have the meanings as set forth below, except to the extent that the context in which they are used indicates otherwise.

A "PKC modulatory compound" is any compound, including small molecules and peptides, which is capable of modulating the enzymatic activity of a PKC isozyme. The term "modulation" refers to increasing or decreasing the enzymatic activity and other functional activities of a PKC isozyme. A specific PKC modulator ("isozyme-specific PKC modulator") is any compound which measurably modulates, either positively or negative, one PKC isozyme over another.

A "PKC activator" is any compound, including small molecules and peptides, which is capable of activating the enzymatic activity of a PKC isozyme. A specific PKC activator is any compound which measurably activates one PKC isozyme over another.

A "PKC inhibitor" is any compound, including small molecules and peptides, which is capable of inhibiting the enzymatic activity and other functional activities of a PKC isozyme. A specific PKC inhibitor is any compound which measurably inhibits one PKC isozyme over another.

An "εPKC activator peptide" refers to a peptide that can activate an εPKC enzyme.

An "εPKC inhibitory peptide" refers to a peptide that can inhibit or inactivate an εPKC enzyme.

An "γPKC activator peptide" refers to a peptide that can activate an γPKC enzyme.

An "γPKC inhibitory peptide" refers to a peptide that can inhibit or inactivate an γPKC enzyme.

The term "KAI-1586" refers to a peptide derived from the first variable region of εPKC conjugated via a Cys-Cys disulfide linkage to a "capped" HIV Tat-derived transporter peptide, and can be represented as follows:

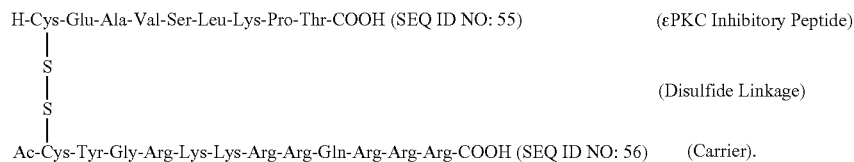

The term "KAI-1634" refers to two modified εPKC peptides derived from the first variable region of εPKC, which are covalently linked and a capped HIV Tat-derived transporter peptide. The construct is depicted in FIG. 1.

Figure 2:
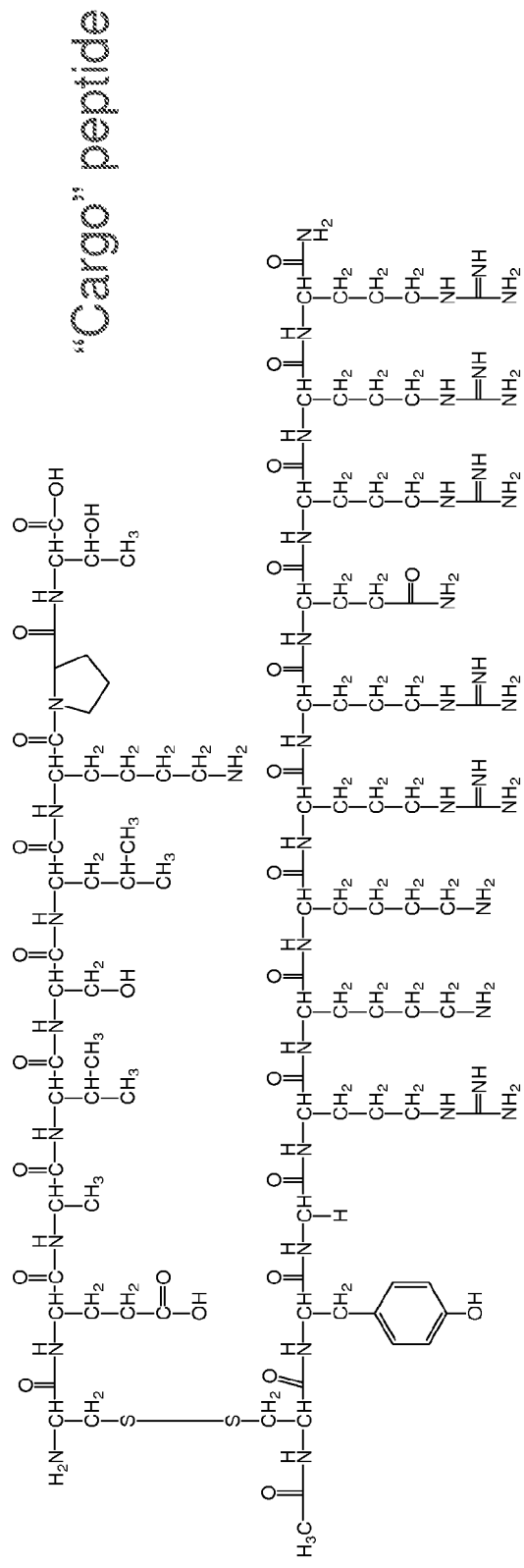
FIG. 2 shows the chemical formula of an inhibitory εPKC inhibitory peptide (KP-1586).

The term "capped" refers to a peptide that has been chemically modified to alter the amino terminus, carboxy terminus, or both. A capped carrier peptide disulfide bonded to an unmodified cargo peptide is shown in FIG. 2.

The term "carrier" refers to a moiety that facilitates cellular uptake, such as cationic polymers, peptides and antibody sequences, including polylysine, polyarginine, Antennapedia-derived peptides, HIV Tat-derived peptides and the like, as described, for example, in U.S. patents and Publications Nos. 4,847,240, 5,888,762, 5,747,641, 6,593,292, US2003/0104622, US2003/0199677 and US2003/0206900. An example of a carrier moiety is a "carrier peptide," which is a peptide which facilitates cellular uptake of an εPKC inhibitory peptide which is chemically associated or bonded to the transporter peptide.

The term "prophylaxis" is intended as an element of "treatment" to encompass both "preventing" and "suppressing" as defined herein. It will be understood by those skilled in the art that in human medicine it is not always possible to distinguish between "preventing" and suppressing since the ultimate inductive event or events may be unknown, latent, or the patient is not ascertained until well after the occurrence of the event or events.

The term "stability" refers generally to modifications that improve shelf-life times, for example, retarding shelf life-based cys-cys exchange, by retarding proteolytic degradation, or both. The term "potency" relates to the amount of a particular peptide composition required to achieve a particular result. One peptide composition is more potent than another when dosages of the composition can be reduced to achieve a desired end point. Certain modifications of a given peptide composition can be made with improve potency of that composition.

Epsilon Protein Kinase C (εPKC) Inhibitors

There are many known inhibitors of εPKC that can be used in the instant invention. Small molecule inhibitors of PKC are described in U.S. Pat. Nos. 5,141,957, 5,204,370, 5,216,014, 5,270,310, 5,292,737, 5,344,841, 5,360,818, 5,432,198, 5,380,746, and 5,489,608, (European Patent 0,434,057), all of which are hereby incorporated by reference in their entirety. These molecules belong to the following classes: N,N'-Bis-(sulfonamido)-2-amino-4-aminonaphthalen-1-ones; N,N'-Bis-(amido)-2-amino-4-aminonaphthalen-1-ones; vicinal-substituted carbocyclics; 1,3-dioxane derivatives; 1,4-Bis-(amino-hydroxyalkylamino) -anthraquinones; furo-coumarinsulfonamides; Bis-(hydroxyalkylamino)-anthraquinones; and N-aminoalkyl amides, 2-[1-(3-Aminopropyl)-1H-indol-3-yl]-3-(1H-indol-3-yl)maleimide, 2-[1-[2-(1-Methylpyrrolidino)ethyl]-1H-indol-3-yl]-3-(1H-indol-3-yl)maleimide, Gö 7874. Other known small molecule inhibitors of PKC are described in the following publications (Fabre, S., et al. 1993. Bioorg. Med. Chem. 1, 193, Toullec, D., et al. 1991. J. Biol. Chem. 266, 15771, Gschwendt, M., et al. 1996. FEBS Lett. 392, 77, Merritt, J. E., et al. 1997. Cell Signal 9, 53., Birchall, A. M., et al. 1994. J. Pharmacol. Exp. Ther. 268, 922. Wilkinson, S. E., et al. 1993. Biochem. J. 294, 335., Davis, P. D., et al. 1992. J. Med. Chem. 35, 994), and belong to the following classes: 2,3-bis(1H-Indol-3-yl)maleimide (Bisindolylmaleimide IV); 2-[1-(3-Dimethylamino-propyl)-5-methoxyindol-3-yl]-3-(1H-indol-3-yl) maleimide (Go 6983); 2-{8-[(Dimethylamino)methyl]-6,7,8,9-tetrahydropyrido[1,2-a]indol-3-yl}-3-(1-methyl-1H-indol-3-yl)maleimide (Ro-32-0432); 2-[8-(Aminomethyl)-6,7,8,9-tetrahydropyrido[1,2-a]indol-3-yl]-3-(1-methyl-1H-indol-3-yl) maleimide (Ro-31-8425); and 3-[1-[3-(Amidinothio)propyl-1H-indol-3-yl]-3-(1-methyl-1H-indol-3-yl)maleimide Bisindolylmaleimide IX, Methanesulfonate (Ro-31-8220) all of which are also hereby incorporated by reference in their entirety.

Epsilon Protein Kinase C (εPKC) Inhibitory Peptides

Various εPKC inhibitors are described herein and can be used with the presently disclosed methods. The inhibitory peptide can be derived from any domain, whether variable or constant. Thus, inhibitory peptides can be derived from V1, V2, V3, V4, or V5. Inhibitory peptides can also be derived from the constant regions C1 (C1a, C1b), C3, C4, or C5. Peptides overlapping one or more of these regions are also contemplated. Another source of prototype peptides can be found in U.S. patent application Ser. No. 11/011,557, entitled, "Isozyme-specific antagonists of protein kinase C," which is hereby incorporated by reference in its entirety.

In one embodiment, the cargo peptide is an εPKC inhibitory peptide derivative of εV1-2 comprising the amino acid sequence of E-A-V-S-L-K-P-T (SEQ ID NO:58), a cysteine residue located at the amino or carboxy terminal ends of the peptide, or internally, and a carrier peptide linked to the cargo peptide. The cargo peptide described above can further comprise one or more additional cargo peptides, attached to one another and ultimately to the carrier peptide.

Modifications to both the carrier and cargo have been made with the goals of improving potency, stability in biological fluids/tissues, and chemical stability. These changes provide an εPKC inhibitor with enhanced properties for use in a variety of clinical indications.

Some of the modifications which have been applied include:

1. Capping the cargo and/or carrier peptides to hinder proteolysis in vivo, and thereby to increase potency and/or duration of efficacy;
2. Generating overlap peptides incorporating additional contiguous regions of the parent protein to improve potency;
3. Making linear peptides which have cargo and carrier in a single peptide chain to improve the chemical stability and shelf-life of drug product;
4. Making multimer peptides which have two or more copies of the active peptide to improve protease resistance and potency;
5. Making retro-inverso analogs of peptides to hinder proteolysis; and
6. Introducing disulfide analogs to provide improved chemical stability.

The modifications described herein improve the potency, plasma stability, and chemical stability of the modified εPKC inhibitory peptides. Effective modifications to εPKC inhibitory peptides are identified by selecting a prototype εPKC inhibitory peptide and modifying these peptides to serve as cargo peptides for the treatment of pain. The prototype peptide can be a presently known peptide or one as of yet unidentified as an εPKC inhibitory peptide. A preferred prototype sequence is E-A-V-S-L-K-P-T (SEQ ID NO:58), where the peptide is unmodified and conjugated to a carrier via Cys residues located at the amino termini of the cargo and carrier peptides, although any inhibitory εPKC peptide can be used as the starting cargo sequence. A variety of modified or analog peptides are contemplated. Some such analogs comprise amino acid sequences that overlap and extend beyond the prototype sequence. Other analog peptides are truncated relative to the prototype. Additionally, analogs of the prototype sequence may have one or more amino acid substitutions relative to the prototype sequence, wherein the amino acid substituted is an alanine residue or an aspartic acid residue. The systematic generation of such alanine or aspartic acid containing peptides is known as "scanning." The generation of linear peptides comprising the analogs and modified carrier peptides is further contemplated.

Additional modifications to prototype sequences are directed at modifying specific degradation sites within the cargo peptide or peptides, the carrier peptide or peptides, or both, and introducing amino acid substitutions or other chemical modifications which blocks these sites from degradation.

Table 1 lists a number of exemplary epsilon PKC inhibitory peptides for use with the present invention as prototype sequences.

TABLE 1

| Peptides derived from epsilon PKC | | | |
|---|---|---|---|
| Peptide | SEQ ID NO. | Sequence | Position |
| εV1-1 | SEQ ID NO: 15 | N-G-L-L-K-I-K | εPKC(5-11) |
| εV1-2 | SEQ ID NO: 58 | E-A-V-S-L-K-P-T | εPKC(14-21) |
| εV1-3 | SEQ ID NO: 16 | L-A-V-F-H-D-A-P-I-G-Y | εPKC(81-91) |
| εV1-4 | SEQ ID NO: 17 | D-D-F-V-A-N-C-T-I | εPKC(92-100) |
| εV1-5 | SEQ ID NO: 18 | W-I-D-L-E-P-E-G-R-V | εPKC(116-125) |
| εV1-6 | SEQ ID NO: 19 | H-A-V-G-P-R-P-Q-T-F | εPKC(27-36) |

TABLE 1-continued

Peptides derived from epsilon PKC

| Peptide | SEQ ID NO. | Sequence | Position |
|---|---|---|---|
| εV1-7 | SEQ ID NO: 20 | N-G-S-R-H-F-E-D | εPKC(108-115) |
| εV1-7.1 | SEQ ID NO: 21 | H-D-A-P-I-G-D-Y | — |
| εV1-7.2 | SEQ ID NO: 22 | H-D-A-P-I-G | — |
| εV1-7.3 | SEQ ID NO: 26 | H-D-A-A-I-G-Y-D | — |
| εV1-7.4 | SEQ ID NO: 27 | H-D-A-P-I-P-Y-D | — |
| εV1-7.5 | SEQ ID NO: 28 | H-N-A-P-I-G-Y-D | — |
| εV1-7.6 | SEQ ID NO: 29 | H-A-A-P-I-G-Y-D | — |
| εV1-7.7 | SEQ ID NO: 30 | A-D-A-P-I-G-Y-D | — |
| εV1-7.8 | SEQ ID NO: 31 | H-D-A-P-A-G-Y-D | — |
| εV1-7.9 | SEQ ID NO: 32 | H-D-A-P-I-G-A-D | — |
| εV1-7.10 | SEQ ID NO: 33 | H-D-A-P-I-A-Y-D | — |
| εV1-7.11 | SEQ ID NO: 34 | H-D-A-P-I-G-Y-A | — |
| εV3-1 | SEQ ID NO: 35 | S-S-P-S-E-E-D-R-S | εPKC(336-344) |
| εV3-2 | SEQ ID NO: 36 | P-C-D-Q-E-I-K-E | εPKC(351-358) |
| εV3-3 | SEQ ID NO: 37 | E-N-N-I-R-K-A-L-S | εPKC(360-368) |
| εV3-4 | SEQ ID NO: 38 | G-E-V-R-Q-G-Q-A | εPKC(393-400) |
| εV5-1 | SEQ ID NO: 39 | E-A-I-V-K-Q | εPKC(714-719) |
| εV5-2 | SEQ ID NO: 40 | I-K-T-K-R-D-V | εPKC(689-695) |
| εV5-2.1 | SEQ ID NO: 41 | I-K-T-K-R-L-I | — |
| εV5-3 | SEQ ID NO: 42 | C-E-A-I-V-K-Q | εPKC(714-719) |
| εV5-4 | SEQ ID NO: 43 | T-K-R-D-V-N-N-F-D-Q | εPKC(791-800) |

As discussed more fully below, it is preferable that the εPKC inhibitory peptide be chemically associated with a carrier moiety, such as a carrier peptide. In one embodiment, the inhibitory peptide and the carrier peptide are linked via a disulfide bond. Electrostatic and hydrophobic interactions can also be exploited to associate chemically the carrier moiety with the εPKC inhibitory peptide. In the case of the forming a disulfide bond, it may be advantageous to add a Cys residue to the PKC inhibitory peptide sequence or to the carrier peptide sequence. The Cys residue can be added to the amino or carboxy termini, or both. The Cys residue can also be located within the amino acid sequence of the cargo or carrier peptides. Such endogenous Cys residues have been shown to stabilize a disulfide bond linkage between the carrier and cargo peptides. Another linking system involves linearizing peptides of interest using glycine residue linkers. One preferred embodiment is KP-1678, which has the sequence of εV1-2 and a TAT carrier peptide, wherein the amino terminus is acetylated and the carboxy terminus is modified with an amino group (Ac-EAVSLKPTG-GYGRKKRRQRRR-NH2) (SEQ ID NO:57).

Hybrid Peptide Constructs

As discussed above a variety of modifications to PKC modulatory peptides are contemplated. One example of such a modification includes the construction of linear peptides comprising, for example a cargo PKC modulatory peptide and a carrier peptide. Another example is a multimer peptide construct comprising a plurality of PKC modulatory peptides and a carrier peptide. Either peptide design model can be modified such that multiple modulatory PKC peptides are included, and those modulatory peptides can be selected such that different PKC isozymes can be modulated with the same construct.

The hybrid peptide approach has various advantages over a single functionality peptide construct. For example, using multiple PKC modulatory peptides in the same construct permits one to modulate simultaneously two or more different PKC isozymes using otherwise isozyme specific modulatory peptides. Joint modulation in this manner, while less specific than the use of isozyme specific peptides alone, is still more specific than using isozyme non-specific peptide modulators and other small molecule type kinase inhibitors. The use of isozyme specific modulatory peptides is merely exemplary. Hybrid peptide constructs can also comprise modulatory peptides which are either specific or non-specific for any PKC isozyme.

Peptide modulators of any of the PKC isozymes are contemplated for use to construct hybrid peptide constructs. The PKC family of isozymes includes at least 11 different protein kinases that can be divided into at least three subfamilies based on their homology and sensitivity to activators. Each isozyme includes a number of homologous ("conserved" or "C") domains interspersed with isozyme-unique ("variable" or "V") domains. Members of the "classical" or "cPKC" subfamily, α, $β_I$, $β_{II}$, and γPKC, contain four homologous domains (C1, C2, C3 and C4) and require calcium, phosphatidylserine, and diacylglycerol or phorbol esters for activation. In members of the "novel" or "nPKC" subfamily, δ, ε, η and θPKC, a C2-like domain precedes the C1 domain. However, that C2 domain does not bind calcium and therefore the nPKC subfamily does not require calcium for activation. Finally, members of the "atypical" or "aPKC" subfamily, ζ and λPKC, lack both the C2 and one-half of the C1 homologous domains and are insensitive to diacylglycerol, phorbol esters and calcium. Modulatory peptides with activity against one or more of the PKC isozymes can be used to prepare hybrid peptide constructs.

In a preferred embodiment, hybrid peptide constructs comprising one or more εPKC modulatory peptides and one or more γPKC modulatory peptides. One a preferred embodiment, one or more εPKC inhibitory peptides are used with one or more γPKC inhibitory peptides to construct an εPKC-γPKC hybrid inhibitory peptide.

Various εPKC inhibitory peptides are discussed above, and these peptides are examples of some of the peptides that can be used to prepare hybrid peptide constructs. Various γPKC inhibitors are described herein and can be used with the presently disclosed methods. The inhibitory peptide can be derived from any domain, whether variable or constant. Thus, inhibitory peptides can be derived from V1, V2, V3, V4, or V5. Inhibitory peptides can also be derived from the constant regions C1 (C1a, C1b), C3, C4, or C5. Peptides overlapping one or more of these regions are also contemplated. The cargo peptides derived from the various domains and range in length from 5 to 30 amino acids in length. More particularly, the peptides derived from the PKC domain are 5, 6, 7, 8, 9, 10, 11, 12, 13, 14, 15, 16, 17, 18, 19, 20, 21, 22, 23, 24, 25, 26, 27, 28, 29, or 30 residues in length. Another source of prototype peptides can be found in U.S. patent application Ser. No. 11/011,557, entitled, "Isozyme-specific antagonists of protein kinase C," which takes activator peptides and converts them to inhibitor peptides, and which is hereby incorporated by reference in its entirety. A preferred γPKC inhibitory peptide prototype sequence is R-L-V-L-A-S (SEQ ID NO:1). All of the modifications described above in relation to the PKC peptides are equally applicable to the γPKC inhibitory peptides contemplated for use in the hybrid constructs.

The following tables list a number of exemplary gamma PKC inhibitory peptides for use with the present invention as prototype sequences.

TABLE 2

BASIC SET

| CARGO | | | | LINKER | CARRIER | | | |
|---|---|---|---|---|---|---|---|---|
| N-term | Cargo | SEQ ID NO: | C-term | Linker | N-term | Carrier | SEQ ID NO: | C-term |
| Amine | CRLVLAS | 2 | Carboxyl | Disulfide | Amine | CYGRKKRRQRRR | 4 | Carboxyl |
| Acetyl | CRLVLAS | 2 | Carboxyl | Disulfide | Amine | CYGRKKRRQRRR | 4 | Carboxyl |
| Acetyl | CRLVLAS | 2 | Amide | Disulfide | Amine | CYGRKKRRQRRR | 4 | Carboxyl |
| Amine | CRLVLAS | 2 | Amide | Disulfide | Amine | CYGRKKRRQRRR | 4 | Carboxyl |
| Amine | CRLVLAS | 2 | Carboxyl | Disulfide | Acetyl | CYGRKKRRQRRR | 4 | Carboxyl |
| Amine | CRLVLAS | 2 | Carboxyl | Disulfide | Acetyl | CYGRKKRRQRRR | 4 | Amide |
| Amine | CRLVLAS | 2 | Carboxyl | Disulfide | Amine | CYGRKKRRQRRR | 4 | Amide |
| Acetyl | CRLVLAS | 2 | Amide | Disulfide | Acetyl | CYGRKKRRQRRR | 4 | Amide |
| Amine | RLVLASC | 3 | Carboxyl | Disulfide | Amine | CYGRKKRRQRRR | 4 | Carboxyl |
| Acetyl | RLVLASC | 3 | Carboxyl | Disulfide | Amine | CYGRKKRRQRRR | 4 | Carboxyl |
| Acetyl | RLVLASC | 3 | Amide | Disulfide | Amine | CYGRKKRRQRRR | 4 | Carboxyl |
| Amine | RLVLASC | 3 | Amide | Disulfide | Amine | CYGRKKRRQRRR | 4 | Carboxyl |
| Amine | RLVLASC | 3 | Carboxyl | Disulfide | Acetyl | CYGRKKRRQRRR | 4 | Carboxyl |
| Amine | RLVLASC | 3 | Carboxyl | Disulfide | Acetyl | CYGRKKRRQRRR | 4 | Amide |
| Amine | RLVLASC | 3 | Carboxyl | Disulfide | Amine | CYGRKKRRQRRR | 4 | Amide |
| Acetyl | RLVLASC | 3 | Amide | Disulfide | Acetyl | CYGRKKRRQRRR | 4 | Amide |
| Amine | RLVLASC | 3 | Carboxyl | Disulfide | Amine | YGRKKRRQRRRC | 5 | Carboxyl |
| Acetyl | RLVLASC | 3 | Carboxyl | Disulfide | Amine | YGRKKRRQRRRC | 5 | Carboxyl |
| Acetyl | RLVLASC | 3 | Amide | Disulfide | Amine | YGRKKRRQRRRC | 5 | Carboxyl |
| Amine | RLVLASC | 3 | Amide | Disulfide | Amine | YGRKKRRQRRRC | 5 | Carboxyl |
| Amine | RLVLASC | 3 | Carboxyl | Disulfide | Acetyl | YGRKKRRQRRRC | 5 | Carboxyl |
| Amine | RLVLASC | 3 | Carboxyl | Disulfide | Acetyl | YGRKKRRQRRRC | 5 | Amide |
| Amine | RLVLASC | 3 | Carboxyl | Disulfide | Amine | YGRKKRRQRRRC | 5 | Amide |
| Acetyl | RLVLASC | 3 | Amide | Disulfide | Acetyl | YGRKKRRQRRRC | 5 | Amide |
| Amine | CRLVLAS | 2 | Carboxyl | Disulfide | Amine | YGRKKRRQRRRC | 5 | Carboxyl |
| Acetyl | CRLVLAS | 2 | Carboxyl | Disulfide | Amine | YGRKKRRQRRRC | 5 | Carboxyl |
| Acetyl | CRLVLAS | 2 | Amide | Disulfide | Amine | YGRKKRRQRRRC | 5 | Carboxyl |
| Amine | CRLVLAS | 3 | Amide | Disulfide | Amine | YGRKKRRQRRRC | 5 | Carboxyl |
| Amine | CRLVLAS | 2 | Carboxyl | Disulfide | Acetyl | YGRKKRRQRRRC | 5 | Carboxyl |
| Amine | CRLVLAS | 2 | Carboxyl | Disulfide | Acetyl | YGRKKRRQRRRC | 5 | Amide |
| Amine | CRLVLAS | 2 | Carboxyl | Disulfide | Amine | YGRKKRRQRRRC | 5 | Amide |
| Acetyl | CRLVLAS | 2 | Amide | Disulfide | Acetyl | YGRKKRRQRRRC | 5 | Amide |

TABLE 3

HOMOCYSTEINE (homoC)

| CARGO | | | | LINKER | CARRIER | | | |
|---|---|---|---|---|---|---|---|---|
| N-term | Cargo | SEQ ID NO: | C-term | Linker | N-term | Carrier | SEQ ID NO: | C-term |
| Amine | homoC-RLVLAS SEQ ID NO: 6 | 6 | Carboxyl | Disulfide | Amine | homoC-YGRKKRRQRRR SEQ ID NO: 8 | 8 | Carboxyl |
| Acetyl | homoC-RLVLAS | 6 | Carboxyl | Disulfide | Amine | homoC-YGRKKRRQRRR | 8 | Carboxyl |
| Acetyl | homoC-RLVLAS | 6 | Amide | Disulfide | Amine | homoC-YGRKKRRQRRR | 8 | Carboxyl |
| Amine | homoC-RLVLAS | 6 | Amide | Disulfide | Amine | homoC-YGRKKRRQRRR | 8 | Carboxyl |
| Amine | homoC-RLVLAS | 6 | Carboxyl | Disulfide | Acetyl | homoC-YGRKKRRQRRR | 8 | Carboxyl |
| Amine | homoC-RLVLAS | 6 | Carboxyl | Disulfide | Acetyl | homoC-YGRKKRRQRRR | 8 | Amide |
| Amine | homoC-RLVLAS | 6 | Carboxyl | Disulfide | Amine | homoC-YGRKKRRQRRR | 8 | Amide |
| Acetyl | homoC-RLVLAS | 6 | Amide | Disulfide | Acetyl | homoC-YGRKKRRQRRR | 8 | Amide |
| Amine | RLVLAS-homoC | 7 | Carboxyl | Disulfide | Amine | homoC-YGRKKRRQRRR | 8 | Carboxyl |
| Acetyl | RLVLAS-homoC | 7 | Carboxyl | Disulfide | Amine | homoC-YGRKKRRQRRR | 8 | Carboxyl |
| Acetyl | RLVLAS-homoC | 7 | Amide | Disulfide | Amine | homoC-YGRKKRRQRRR | 8 | Carboxyl |
| Amine | RLVLAS-homoC | 7 | Amide | Disulfide | Amine | homoC-YGRKKRRQRRR | 8 | Carboxyl |

TABLE 3-continued

HOMOCYSTEINE (homoC)

| | CARGO | | | LINKER | | CARRIER | | |
|---|---|---|---|---|---|---|---|---|
| N-term | Cargo | SEQ ID NO: | C-term | Linker | N-term | Carrier | SEQ ID NO: | C-term |
| Amine | RLVLAS-homoC | 7 | Carboxyl | Disulfide | Acetyl | homoC-YGRKKRRQRRR | 8 | Carboxyl |
| Amine | RLVLAS-homoC | 7 | Carboxyl | Disulfide | Acetyl | homoC-YGRKKRRQRRR | 8 | Amide |
| Amine | RLVLAS-homoC | 7 | Carboxyl | Disulfide | Amine | homoC-YGRKKRRQRRR | 8 | Amide |
| Acetyl | RLVLAS-homoC | 7 | Amide | Disulfide | Acetyl | homoC-YGRKKRRQRRR | 8 | Amide |
| Amine | RLVLAS-homoC | 7 | Carboxyl | Disulfide | Amine | YGRKKRRQRRR-homoC | 9 | Carboxyl |
| Acetyl | RLVLAS-homoC | 7 | Carboxyl | Disulfide | Amine | YGRKKRRQRRR-homoC | 9 | Carboxyl |
| Acetyl | RLVLAS-homoC | 7 | Amide | Disulfide | Amine | YGRKKRRQRRR-homoC | 9 | Carboxyl |
| Amine | RLVLAS-homoC | 7 | Amide | Disulfide | Amine | YGRKKRRQRRR-homoC | 9 | Carboxyl |
| Amine | RLVLAS-homoC | 7 | Carboxyl | Disulfide | Acetyl | YGRKKRRQRRR-homoC | 9 | Carboxyl |
| Amine | RLVLAS-homoC | 7 | Carboxyl | Disulfide | Acetyl | YGRKKRRQRRR-homoC | 9 | Amide |
| Amine | RLVLAS-homoC | 7 | Carboxyl | Disulfide | Amine | YGRKKRRQRRR-homoC | 9 | Amide |
| Acetyl | RLVLAS-homoC | 7 | Amide | Disulfide | Acetyl | YGRKKRRQRRR-homoC | 9 | Amide |
| Amine | homoC-RLVLAS | 6 | Carboxyl | Disulfide | Amine | YGRKKRRQRRR-homoC | 9 | Carboxyl |
| Acetyl | homoC-RLVLAS | 6 | Carboxyl | Disulfide | Amine | YGRKKRRQRRR-homoC | 9 | Carboxyl |
| Acetyl | homoC-RLVLAS | 6 | Amide | Disulfide | Amine | YGRKKRRQRRR-homoC | 9 | Carboxyl |
| Amine | homoC-RLVLAS | 6 | Amide | Disulfide | Amine | YGRKKRRQRRR-homoC | 9 | Carboxyl |
| Amine | homoC-RLVLAS | 6 | Carboxyl | Disulfide | Acetyl | YGRKKRRQRRR-homoC | 9 | Carboxyl |
| Amine | homoC-RLVLAS | 6 | Carboxyl | Disulfide | Acetyl | YGRKKRRQRRR-homoC | 9 | Amide |
| Amine | homoC-RLVLAS | 6 | Carboxyl | Disulfide | Amine | YGRKKRRQRRR-homoC | 9 | Amide |
| Acetyl | homoC-RLVLAS | 6 | Amide | Disulfide | Acetyl | YGRKKRRQRRR-homoC | 9 | Amide |

TABLE 4

HOMOCYSTEINE (homoC) - Cargo only

| | CARGO | | | LINKER | | CARRIER | | |
|---|---|---|---|---|---|---|---|---|
| N-term | Cargo | SEQ ID NO: | C-term | Linker | N-term | Carrier | SEQ ID NO: | C-term |
| Amine | homoC-RLVLAS | 6 | Carboxyl | Disulfide | Amine | CYGRKKRRQRRR | 4 | Carboxyl |
| Acetyl | homoC-RLVLAS | 6 | Carboxyl | Disulfide | Amine | CYGRKKRRQRRR | 4 | Carboxyl |
| Acetyl | homoC-RLVLAS | 6 | Amide | Disulfide | Amine | CYGRKKRRQRRR | 4 | Carboxyl |
| Amine | homoC-RLVLAS | 6 | Amide | Disulfide | Amine | CYGRKKRRQRRR | 4 | Carboxyl |
| Amine | homoC-RLVLAS | 6 | Carboxyl | Disulfide | Acetyl | CYGRKKRRQRRR | 4 | Carboxyl |
| Amine | homoC-RLVLAS | 6 | Carboxyl | Disulfide | Acetyl | CYGRKKRRQRRR | 4 | Amide |
| Amine | homoC-RLVLAS | 6 | Carboxyl | Disulfide | Amine | CYGRKKRRQRRR | 4 | Amide |
| Acetyl | homoC-RLVLAS | 6 | Amide | Disulfide | Acetyl | CYGRKKRRQRRR | 4 | Amide |
| Amine | RLVLAS-homoC | 7 | Carboxyl | Disulfide | Amine | CYGRKKRRQRRR | 4 | Carboxyl |
| Acetyl | RLVLAS-homoC | 7 | Carboxyl | Disulfide | Amine | CYGRKKRRQRRR | 4 | Carboxyl |
| Acetyl | RLVLAS-homoC | 7 | Amide | Disulfide | Amine | CYGRKKRRQRRR | 4 | Carboxyl |
| Amine | RLVLAS-homoC | 7 | Amide | Disulfide | Amine | CYGRKKRRQRRR | 4 | Carboxyl |
| Amine | RLVLAS-homoC | 7 | Carboxyl | Disulfide | Acetyl | CYGRKKRRQRRR | 4 | Carboxyl |
| Amine | RLVLAS-homoC | 7 | Carboxyl | Disulfide | Acetyl | CYGRKKRRQRRR | 4 | Amide |
| Amine | RLVLAS-homoC | 7 | Carboxyl | Disulfide | Amine | CYGRKKRRQRRR | 4 | Amide |
| Acetyl | RLVLAS-homoC | 7 | Amide | Disulfide | Acetyl | CYGRKKRRQRRR | 4 | Amide |
| Amine | RLVLAS-homoC | 7 | Carboxyl | Disulfide | Amine | YGRKKRRQRRRC | 5 | Carboxyl |
| Acetyl | RLVLAS-homoC | 7 | Carboxyl | Disulfide | Amine | YGRKKRRQRRRC | 5 | Carboxyl |
| Acetyl | RLVLAS-homoC | 7 | Amide | Disulfide | Amine | YGRKKRRQRRRC | 5 | Carboxyl |
| Amine | RLVLAS-homoC | 7 | Amide | Disulfide | Amine | YGRKKRRQRRRC | 5 | Carboxyl |
| Amine | RLVLAS-homoC | 7 | Carboxyl | Disulfide | Acetyl | YGRKKRRQRRRC | 5 | Carboxyl |
| Amine | RLVLAS-homoC | 7 | Carboxyl | Disulfide | Acetyl | YGRKKRRQRRRC | 5 | Amide |
| Amine | RLVLAS-homoC | 7 | Carboxyl | Disulfide | Amine | YGRKKRRQRRRC | 5 | Amide |
| Acetyl | RLVLAS-homoC | 7 | Amide | Disulfide | Acetyl | YGRKKRRQRRRC | 5 | Amide |
| Amine | homoC-RLVLAS | 6 | Carboxyl | Disulfide | Amine | YGRKKRRQRRRC | 5 | Carboxyl |
| Acetyl | homoC-RLVLAS | 6 | Carboxyl | Disulfide | Amine | YGRKKRRQRRRC | 5 | Carboxyl |
| Acetyl | homoC-RLVLAS | 6 | Amide | Disulfide | Amine | YGRKKRRQRRRC | 5 | Carboxyl |
| Amine | homoC-RLVLAS | 6 | Amide | Disulfide | Amine | YGRKKRRQRRRC | 5 | Carboxyl |
| Amine | homoC-RLVLAS | 6 | Carboxyl | Disulfide | Acetyl | YGRKKRRQRRRC | 5 | Carboxyl |
| Amine | homoC-RLVLAS | 6 | Carboxyl | Disulfide | Acetyl | YGRKKRRQRRRC | 5 | Amide |
| Amine | homoC-RLVLAS | 6 | Carboxyl | Disulfide | Amine | YGRKKRRQRRRC | 5 | Amide |
| Acetyl | homoC-RLVLAS | 6 | Amide | Disulfide | Acetyl | YGRKKRRQRRRC | 5 | Amide |

TABLE 5

HOMOCYSTEINE (homoC) - Carrier only

| | CARGO | | | LINKER | | CARRIER | | |
|---|---|---|---|---|---|---|---|---|
| N-term | Cargo | SEQ ID NO: | C-term | Linker | N-term | Carrier | SEQ ID NO: | C-term |
| Amine | CRLVLAS | 2 | Carboxyl | Disulfide | Amine | homoC-YGRKKRRQRRR | 8 | Carboxyl |
| Acetyl | CRLVLAS | 2 | Carboxyl | Disulfide | Amine | homoC-YGRKKRRQRRR | 8 | Carboxyl |
| Acetyl | CRLVLAS | 2 | Amide | Disulfide | Amine | homoC-YGRKKRRQRRR | 8 | Carboxyl |
| Amine | CRLVLAS | 2 | Amide | Disulfide | Amine | homoC-YGRKKRRQRRR | 8 | Carboxyl |
| Amine | CRLVLAS | 2 | Carboxyl | Disulfide | Acetyl | homoC-YGRKKRRQRRR | 8 | Carboxyl |
| Amine | CRLVLAS | 2 | Carboxyl | Disulfide | Acetyl | homoC-YGRKKRRQRRR | 8 | Amide |
| Amine | CRLVLAS | 2 | Carboxyl | Disulfide | Amine | homoC-YGRKKRRQRRR | 8 | Amide |
| Acetyl | CRLVLAS | 2 | Amide | Disulfide | Acetyl | homoC-YGRKKRRQRRR | 8 | Amide |
| Amine | RLVLASC | 3 | Carboxyl | Disulfide | Amine | homoC-YGRKKRRQRRR | 8 | Carboxyl |
| Acetyl | RLVLASC | 3 | Carboxyl | Disulfide | Amine | homoC-YGRKKRRQRRR | 8 | Carboxyl |
| Acetyl | RLVLASC | 3 | Amide | Disulfide | Amine | homoC-YGRKKRRQRRR | 8 | Carboxyl |
| Amine | RLVLASC | 3 | Amide | Disulfide | Amine | homoC-YGRKKRRQRRR | 8 | Carboxyl |
| Amine | RLVLASC | 3 | Carboxyl | Disulfide | Acetyl | homoC-YGRKKRRQRRR | 8 | Carboxyl |
| Amine | RLVLASC | 3 | Carboxyl | Disulfide | Acetyl | homoC-YGRKKRRQRRR | 8 | Amide |
| Amine | RLVLASC | 3 | Carboxyl | Disulfide | Amine | homoC-YGRKKRRQRRR | 8 | Amide |
| Acetyl | RLVLASC | 3 | Amide | Disulfide | Acetyl | homoC-YGRKKRRQRRR | 8 | Amide |
| Amine | RLVLASC | 3 | Carboxyl | Disulfide | Amine | YGRKKRRQRRR-homoC | 9 | Carboxyl |
| Acetyl | RLVLASC | 3 | Carboxyl | Disulfide | Amine | YGRKKRRQRRR-homoC | 9 | Carboxyl |
| Acetyl | RLVLASC | 3 | Amide | Disulfide | Amine | YGRKKRRQRRR-homoC | 9 | Carboxyl |
| Amine | RLVLASC | 3 | Amide | Disulfide | Amine | YGRKKRRQRRR-homoC | 9 | Carboxyl |
| Amine | RLVLASC | 3 | Carboxyl | Disulfide | Acetyl | YGRKKRRQRRR-homoC | 9 | Carboxyl |
| Amine | RLVLASC | 3 | Carboxyl | Disulfide | Acetyl | YGRKKRRQRRR-homoC | 9 | Amide |
| Amine | RLVLASC | 3 | Carboxyl | Disulfide | Amine | YGRKKRRQRRR-homoC | 9 | Amide |
| Acetyl | RLVLASC | 3 | Amide | Disulfide | Acetyl | YGRKKRRQRRR-homoC | 9 | Amide |
| Amine | CRLVLAS | 2 | Carboxyl | Disulfide | Amine | YGRKKRRQRRR-homoC | 9 | Carboxyl |
| Acetyl | CRLVLAS | 2 | Carboxyl | Disulfide | Amine | YGRKKRRQRRR-homoC | 9 | Carboxyl |
| Acetyl | CRLVLAS | 2 | Amide | Disulfide | Amine | YGRKKRRQRRR-homoC | 9 | Carboxyl |
| Amine | CRLVLAS | 2 | Amide | Disulfide | Amine | YGRKKRRQRRR-homoC | 9 | Carboxyl |
| Amine | CRLVLAS | 2 | Carboxyl | Disulfide | Acetyl | YGRKKRRQRRR-homoC | 9 | Carboxyl |
| Amine | CRLVLAS | 2 | Carboxyl | Disulfide | Acetyl | YGRKKRRQRRR-homoC | 9 | Amide |
| Amine | CRLVLAS | 2 | Carboxyl | Disulfide | Amine | YGRKKRRQRRR-homoC | 9 | Amide |
| Acetyl | CRLVLAS | 2 | Amide | Disulfide | Acetyl | YGRKKRRQRRR-homoC | 9 | Amide |

TABLE 6

MERCAPTOPROPIONIC ACID (MerPC)

| | CARGO | | | LINKER | | CARRIER | | |
|---|---|---|---|---|---|---|---|---|
| N-term | Cargo | SEQ ID NO: | C-term | Linker | N-term | Carrier | SEQ ID NO: | C-term |
| Amine | MerPC-RLVLAS SEQ ID NO: 10 | 10 10 | Carboxyl | Disulfide | Amine | MerPC-YGRKKRRQRRR SEQ ID NO: 11 | 11 11 | Carboxyl |
| Acetyl | MerPC-RLVLAS | 10 | Carboxyl | Disulfide | Amine | MerPC-YGRKKRRQRRR | 11 | Carboxyl |
| Acetyl | MerPC-RLVLAS | 10 | Amide | Disulfide | Amine | MerPC-YGRKKRRQRRR | 11 | Carboxyl |
| Amine | MerPC-RLVLAS | 10 | Amide | Disulfide | Amine | MerPC-YGRKKRRQRRR | 11 | Carboxyl |
| Amine | MerPC-RLVLAS | 10 | Carboxyl | Disulfide | Acetyl | MerPC-YGRKKRRQRRR | 11 | Carboxyl |
| Amine | MerPC-RLVLAS | 10 | Carboxyl | Disulfide | Acetyl | MerPC-YGRKKRRQRRR | 11 | Amide |
| Amine | MerPC-RLVLAS | 10 | Carboxyl | Disulfide | Amine | MerPC-YGRKKRRQRRR | 11 | Amide |
| Acetyl | MerPC-RLVLAS | 10 | Amide | Disulfide | Acetyl | MerPC-YGRKKRRQRRR | 11 | Amide |
| Amine | MerPC-RLVLAS | 10 | Carboxyl | Disulfide | Amine | CYGRKKRRQRRR | 4 | Carboxyl |
| Acetyl | MerPC-RLVLAS | 10 | Carboxyl | Disulfide | Amine | CYGRKKRRQRRR | 4 | Carboxyl |
| Acetyl | MerPC-RLVLAS | 10 | Amide | Disulfide | Amine | CYGRKKRRQRRR | 4 | Carboxyl |
| Amine | MerPC-RLVLAS | 10 | Amide | Disulfide | Amine | CYGRKKRRQRRR | 4 | Carboxyl |
| Amine | MerPC-RLVLAS | 10 | Carboxyl | Disulfide | Acetyl | CYGRKKRRQRRR | 4 | Carboxyl |
| Amine | MerPC-RLVLAS | 10 | Carboxyl | Disulfide | Acetyl | CYGRKKRRQRRR | 4 | Amide |
| Amine | MerPC-RLVLAS | 10 | Carboxyl | Disulfide | Amine | CYGRKKRRQRRR | 4 | Amide |
| Acetyl | MerPC-RLVLAS | 10 | Amide | Disulfide | Acetyl | CYGRKKRRQRRR | 4 | Amide |
| Amine | CRLVLAS | 2 | Carboxyl | Disulfide | Amine | MerPC-YGRKKRRQRRR | 11 | Carboxyl |
| Acetyl | CRLVLAS | 2 | Carboxyl | Disulfide | Amine | MerPC-YGRKKRRQRRR | 11 | Carboxyl |
| Acetyl | CRLVLAS | 2 | Amide | Disulfide | Amine | MerPC-YGRKKRRQRRR | 11 | Carboxyl |
| Amine | CRLVLAS | 2 | Amide | Disulfide | Amine | MerPC-YGRKKRRQRRR | 11 | Carboxyl |
| Amine | CRLVLAS | 2 | Carboxyl | Disulfide | Acetyl | MerPC-YGRKKRRQRRR | 11 | Carboxyl |
| Amine | CRLVLAS | 2 | Carboxyl | Disulfide | Acetyl | MerPC-YGRKKRRQRRR | 11 | Amide |
| Amine | CRLVLAS | 2 | Carboxyl | Disulfide | Amine | MerPC-YGRKKRRQRRR | 11 | Amide |
| Acetyl | CRLVLAS | 2 | Amide | Disulfide | Acetyl | MerPC-YGRKKRRQRRR | 11 | Amide |

TABLE 7

MERCAPTOACETIC ACID (MerAC)

| CARGO | | | | LINKER | CARRIER | | | |
|---|---|---|---|---|---|---|---|---|
| N-term | Cargo | SEQ ID NO: | C-term | Linker | N-term | Carrier | SEQ ID NO: | C-term |
| Amine | MerAC-RLVLAS | 24 | Carboxyl | Disulfide | Amine | MerAC-YGRKKRRQRRR | 25 | Carboxyl |
| Acetyl | MerAC-RLVLAS | 24 | Carboxyl | Disulfide | Amine | MerAC-YGRKKRRQRRR | 25 | Carboxyl |
| Acetyl | MerAC-RLVLAS | 24 | Amide | Disulfide | Amine | MerAC-YGRKKRRQRRR | 25 | Carboxyl |
| Amine | MerAC-RLVLAS | 24 | Amide | Disulfide | Amine | MerAC-YGRKKRRQRRR | 25 | Carboxyl |
| Amine | MerAC-RLVLAS | 24 | Carboxyl | Disulfide | Acetyl | MerAC-YGRKKRRQRRR | 25 | Carboxyl |
| Amine | MerAC-RLVLAS | 24 | Carboxyl | Disulfide | Acetyl | MerAC-YGRKKRRQRRR | 25 | Amide |
| Amine | MerAC-RLVLAS | 24 | Carboxyl | Disulfide | Amine | MerAC-YGRKKRRQRRR | 25 | Amide |
| Acetyl | MerAC-RLVLAS | 24 | Amide | Disulfide | Acetyl | MerAC-YGRKKRRQRRR | 25 | Amide |
| Amine | MerAC-RLVLAS | 24 | Carboxyl | Disulfide | Amine | CYGRKKRRQRRR | 4 | Carboxyl |
| Acetyl | MerAC-RLVLAS | 24 | Carboxyl | Disulfide | Amine | CYGRKKRRQRRR | 4 | Carboxyl |
| Acetyl | MerAC-RLVLAS | 24 | Amide | Disulfide | Amine | CYGRKKRRQRRR | 4 | Carboxyl |
| Amine | MerAC-RLVLAS | 24 | Amide | Disulfide | Amine | CYGRKKRRQRRR | 4 | Carboxyl |
| Amine | MerAC-RLVLAS | 24 | Carboxyl | Disulfide | Acetyl | CYGRKKRRQRRR | 4 | Carboxyl |
| Amine | MerAC-RLVLAS | 24 | Carboxyl | Disulfide | Acetyl | CYGRKKRRQRRR | 4 | Amide |
| Amine | MerAC-RLVLAS | 24 | Carboxyl | Disulfide | Amine | CYGRKKRRQRRR | 4 | Amide |
| Acetyl | MerAC-RLVLAS | 24 | Amide | Disulfide | Acetyl | CYGRKKRRQRRR | 4 | Amide |
| Amine | CRLVLAS | 2 | Carboxyl | Disulfide | Amine | MerAC-YGRKKRRQRRR | 25 | Carboxyl |
| Acetyl | CRLVLAS | 2 | Carboxyl | Disulfide | Amine | MerAC-YGRKKRRQRRR | 25 | Carboxyl |
| Acetyl | CRLVLAS | 2 | Amide | Disulfide | Amine | MerAC-YGRKKRRQRRR | 25 | Carboxyl |
| Amine | CRLVLAS | 2 | Amide | Disulfide | Amine | MerAC-YGRKKRRQRRR | 25 | Carboxyl |
| Amine | CRLVLAS | 2 | Carboxyl | Disulfide | Acetyl | MerAC-YGRKKRRQRRR | 25 | Carboxyl |
| Amine | CRLVLAS | 2 | Carboxyl | Disulfide | Acetyl | MerAC-YGRKKRRQRRR | 25 | Amide |
| Amine | CRLVLAS | 2 | Carboxyl | Disulfide | Amine | MerAC-YGRKKRRQRRR | 25 | Amide |
| Acetyl | CRLVLAS | 2 | Amide | Disulfide | Acetyl | MerAC-YGRKKRRQRRR | 25 | Amide |

TABLE 8

MERCAPTOBUTYRIC ACID (MerBC)

| CARGO | | | | LINKER | CARRIER | | | |
|---|---|---|---|---|---|---|---|---|
| N-term | Cargo | SEQ ID NO: | C-term | Linker | N-term | Carrier | SEQ ID NO: | C-term |
| Amine | MerBC-RLVLAS | 23 | Carboxyl | Disulfide | Amine | MerBC-YGRKKRRQRRR | 12 | Carboxyl |
| Acetyl | MerBC-RLVLAS | 23 | Carboxyl | Disulfide | Amine | MerBC-YGRKKRRQRRR | 12 | Carboxyl |
| Acetyl | MerBC-RLVLAS | 23 | Amide | Disulfide | Amine | MerBC-YGRKKRRQRRR | 12 | Carboxyl |
| Amine | MerBC-RLVLAS | 23 | Amide | Disulfide | Amine | MerBC-YGRKKRRQRRR | 12 | Carboxyl |
| Amine | MerBC-RLVLAS | 23 | Carboxyl | Disulfide | Acetyl | MerBC-YGRKKRRQRRR | 12 | Carboxyl |
| Amine | MerBC-RLVLAS | 23 | Carboxyl | Disulfide | Acetyl | MerBC-YGRKKRRQRRR | 12 | Amide |
| Amine | MerBC-RLVLAS | 23 | Carboxyl | Disulfide | Amine | MerBC-YGRKKRRQRRR | 12 | Amide |
| Acetyl | MerBC-RLVLAS | 23 | Amide | Disulfide | Acetyl | MerBC-YGRKKRRQRRR | 12 | Amide |
| Amine | MerBC-RLVLAS | 23 | Carboxyl | Disulfide | Amine | CYGRKKRRQRRR | 4 | Carboxyl |
| Acetyl | MerBC-RLVLAS | 23 | Carboxyl | Disulfide | Amine | CYGRKKRRQRRR | 4 | Carboxyl |
| Acetyl | MerBC-RLVLAS | 23 | Amide | Disulfide | Amine | CYGRKKRRQRRR | 4 | Carboxyl |
| Amine | MerBC-RLVLAS | 23 | Amide | Disulfide | Amine | CYGRKKRRQRRR | 4 | Carboxyl |
| Amine | MerBC-RLVLAS | 23 | Carboxyl | Disulfide | Acetyl | CYGRKKRRQRRR | 4 | Carboxyl |
| Amine | MerBC-RLVLAS | 23 | Carboxyl | Disulfide | Acetyl | CYGRKKRRQRRR | 4 | Amide |
| Amine | MerBC-RLVLAS | 23 | Carboxyl | Disulfide | Amine | CYGRKKRRQRRR | 4 | Amide |
| Acetyl | MerBC-RLVLAS | 23 | Amide | Disulfide | Acetyl | CYGRKKRRQRRR | 4 | Amide |
| Amine | CRLVLAS | 2 | Carboxyl | Disulfide | Amine | MerBC-YGRKKRRQRRR | 12 | Carboxyl |
| Acetyl | CRLVLAS | 2 | Carboxyl | Disulfide | Amine | MerBC-YGRKKRRQRRR | 12 | Carboxyl |
| Acetyl | CRLVLAS | 2 | Amide | Disulfide | Amine | MerBC-YGRKKRRQRRR | 12 | Carboxyl |
| Amine | CRLVLAS | 2 | Amide | Disulfide | Amine | MerBC-YGRKKRRQRRR | 12 | Carboxyl |
| Amine | CRLVLAS | 2 | Carboxyl | Disulfide | Acetyl | MerBC-YGRKKRRQRRR | 12 | Carboxyl |
| Amine | CRLVLAS | 2 | Carboxyl | Disulfide | Acetyl | MerBC-YGRKKRRQRRR | 12 | Amide |
| Amine | CRLVLAS | 2 | Carboxyl | Disulfide | Amine | MerBC-YGRKKRRQRRR | 12 | Amide |
| Acetyl | CRLVLAS | 2 | Amide | Disulfide | Acetyl | MerBC-YGRKKRRQRRR | 12 | Amide |

TABLE 9

Ala-Cys

| | CARGO | | | LINKER | | CARRIER | | |
|---|---|---|---|---|---|---|---|---|
| N-term | Cargo | SEQ ID NO: | C-term | Linker | N-term | Carrier | SEQ ID NO: | C-term |
| Amine | ACRLVLAS | 13 | Carboxyl | Disulfide | Amine | ACYGRKKRRQRRR | 14 | Carboxyl |
| Acetyl | ACRLVLAS | 13 | Carboxyl | Disulfide | Amine | ACYGRKKRRQRRR | 14 | Carboxyl |
| Acetyl | ACRLVLAS | 13 | Amide | Disulfide | Amine | ACYGRKKRRQRRR | 14 | Carboxyl |
| Amine | ACRLVLAS | 13 | Amide | Disulfide | Amine | ACYGRKKRRQRRR | 14 | Carboxyl |
| Amine | ACRLVLAS | 13 | Carboxyl | Disulfide | Acetyl | ACYGRKKRRQRRR | 14 | Carboxyl |
| Amine | ACRLVLAS | 13 | Carboxyl | Disulfide | Acetyl | ACYGRKKRRQRRR | 14 | Amide |
| Amine | ACRLVLAS | 13 | Carboxyl | Disulfide | Amine | ACYGRKKRRQRRR | 14 | Amide |
| Acetyl | ACRLVLAS | 13 | Amide | Disulfide | Acetyl | ACYGRKKRRQRRR | 14 | Amide |
| Amine | ACRLVLAS | 13 | Carboxyl | Disulfide | Amine | CYGRKKRRQRRR | 4 | Carboxyl |
| Acetyl | ACRLVLAS | 13 | Carboxyl | Disulfide | Amine | CYGRKKRRQRRR | 4 | Carboxyl |
| Acetyl | ACRLVLAS | 13 | Amide | Disulfide | Amine | CYGRKKRRQRRR | 4 | Carboxyl |
| Amine | ACRLVLAS | 13 | Amide | Disulfide | Amine | CYGRKKRRQRRR | 4 | Carboxyl |
| Amine | ACRLVLAS | 13 | Carboxyl | Disulfide | Acetyl | CYGRKKRRQRRR | 4 | Carboxyl |
| Amine | ACRLVLAS | 13 | Carboxyl | Disulfide | Acetyl | CYGRKKRRQRRR | 4 | Amide |
| Amine | ACRLVLAS | 13 | Carboxyl | Disulfide | Amine | CYGRKKRRQRRR | 4 | Amide |
| Acetyl | ACRLVLAS | 13 | Amide | Disulfide | Acetyl | CYGRKKRRQRRR | 4 | Amide |
| Amine | CRLVLAS | 2 | Carboxyl | Disulfide | Amine | ACYGRKKRRQRRR | 14 | Carboxyl |
| Acetyl | CRLVLAS | 2 | Carboxyl | Disulfide | Amine | ACYGRKKRRQRRR | 14 | Carboxyl |
| Acetyl | CRLVLAS | 2 | Amide | Disulfide | Amine | ACYGRKKRRQRRR | 14 | Carboxyl |
| Amine | CRLVLAS | 2 | Amide | Disulfide | Amine | ACYGRKKRRQRRR | 14 | Carboxyl |
| Amine | CRLVLAS | 2 | Carboxyl | Disulfide | Acetyl | ACYGRKKRRQRRR | 14 | Carboxyl |
| Amine | CRLVLAS | 2 | Carboxyl | Disulfide | Acetyl | ACYGRKKRRQRRR | 14 | Amide |
| Amine | CRLVLAS | 2 | Carboxyl | Disulfide | Amine | ACYGRKKRRQRRR | 14 | Amide |
| Acetyl | CRLVLAS | 2 | Amide | Disulfide | Acetyl | ACYGRKKRRQRRR | 14 | Amide |

All of the PKC peptides discussed in U.S. Provisional No. 60/910,588, filed Apr. 6, 2007 are hereby incorporated by reference.

Carrier Moiety

A wide variety of molecules (particularly macromolecules such as peptides) intended for cellular uptake have been found to be poorly transported across cell membranes. Among the solutions proposed to facilitate cellular uptake have been the use of carrier moieties such as cationic (i.e., positively charged) polymers, peptides and antibody sequences, including polylysine, polyarginine, Antennapedia-derived peptides, HIV Tat-derived peptides and the like. (See, for example, U.S. patents and Publications Nos. 4,847,240, 5,888,762, 5,747,641, 6,593,292, US2003/0104622, US2003/0199677 and US2003/0206900.)

A particular example of a cargo/carrier conjugate is KP-1634 (SEQ ID NO:49), which is made up of two εPKC-derived peptides with amino terminal caps and a HIV Tat-derived carrier peptide which has been capped at both its amino and carboxy terminal ends.

Additional Inhibitors

Additional inhibitors of εPKC can be identified using assays that measure the activation, intracellular translocation, binding to intracellular receptors (e.g. RACKs) or catalytic activity of εPKC. Traditionally, the kinase activity of PKC family members has been assayed using at least partially purified PKC in a reconstituted phospholipid environment with radioactive ATP as the phosphate donor and a histone protein or a short peptide as the substrate (T. Kitano, M. Go, U. Kikkawa, Y. Nishizuka, Meth. Enzymol. 124, 349-352 (1986); R. O. Messing, P. J. Peterson, C. J. Henrich, J. Biol. Chem. 266, 23428-23432 (1991)). Recent improvements include a rapid, highly sensitive chemiluminescent assay that measures protein kinase activity at physiological concentrations and can be automated and/or used in high-throughput screening (C. Lehel, S. Daniel-Issakani, M. Brasseur, B. Strulovici, Anal. Biochem. 244, 340-346 (1997)) and an assay using PKC in isolated membranes and a selective peptide substrate that is derived from the MARCKS protein (B. R. Chakravarthy, A Bussey, J. F. Whitfield, M. Sikorska, R. E. Williams, J. P. Durkin, Anal. Biochem. 196, 144-150 (1991)). Inhibitors that affect the intracellular translocation of εPKC can be identified by assays in which the intracellular localization of εPKC is determined by fractionation (R. O. Messing, P. J. Peterson, C. J. Henrich, J. Biol. Chem. 266, 23428-23432 (1991)) or immunohistochemistry (U.S. Pat. No. 5,783,405; U.S. patent application Ser. No. 08/686,796 now U.S. Pat. No. 6,255,057, now U.S. Pat. No. 6,255,057). To identify an inhibitor of εPKC, the assays should be performed with εPKC. The selectivity of such εPKC inhibitors can be determined by comparing the effect of the inhibitor on εPKC with its effect on other PKC isozymes. The relevant portions of foregoing patents and publications are hereby incorporated by reference.

Additional assays for identifying εPKC inhibitors can be found in U.S. Pat. Nos. 5,783,405, 6,156,977, and 6,423,684, all of which are hereby incorporated by reference in their entirety.

Mechanisms

Experimental data reported here shows that (1) locally-delivered εPKC inhibitory peptides to the hindlimbs of test animals produced anti-hyperalgesic/analgesic effects in neuropathetic and inflammatory pain models; (2) such effects of the εPKC inhibitory peptides are though to be mediated by nerves traveling inside the sciatic and saphenous afferents, which project to the hindlimbs and thus could be part of a neuronal reflex subject to be inhibited by the εPKC inhibitory peptides; (3) the effects of the εPKC inhibitory peptides appears to be sympathoadrenal-dependent, which coincides with the reports that εPKC not only exists in sympathetic ganglia and functions to the neurotransmitter-releasing process (e.g., Scholze et al.: *J Neurosci.*, 22: 5823-32, 2002) but also modulates sensitization of the C-fibers (a pain-sensing nerve) (Khasar, et al., *Neuron,* 24: 253-260, 1999); and (4) the anti-hyperalgesic/analgesic effects of the εPKC inhibitory peptides is mediated by adrenoceptors. Of note, epinephrine (EPI), one of the neurotransmitters released from the adrenal medulla and sympathetic post-ganglionic neuron (SPGN) terminals, is known to sensitize the C-fibers (Chen & Levine, J. Pain, 6: 439-446, 2005; Khasar, et al., Neuron, 24: 253-260, 1999). It was reported that εPKC modulates $Ca^{++}$ influx (Boehm et al., J. Neurosci., 16: 4516-603, 1996) by phosphorylating the N-type calcium channels (Zhu and Ikeda, J. Neurophysiol., 74: 1546-60, 1994) and thus regulates the release of catecholamines from the sympathetic neurons (Scholze et al.: J. Neurosci., 22: 5823-32, 2002).

Identification of the anti-hyperalgesic effects of εPKC inhibitory peptides differs from that discussed by Messing & Levine (U.S. Pat. No. 6,686,334 B2, U.S. Pat. No. 6,376,467 B1 and 2002/0151465 A1), in which exogenous EPI or isopropranolol (ISO, a synthetic β-adrenoceptor agonist) acts on the C-fibers via stimulating β-adrenoceptors. In that work, the pro-hyperalgesic effects of exogenous EPI or ISO are εPKC-dependent and do not act on the autoregulatory $\alpha_2$-adrneoceptors on the SPGN terminals. U.S. Pat. Nos. 6,686,334 and 6,376,467 and Pub. No. 2002/0151465 A1 focused on the anti-hyperalgesic effects of $\epsilon V_{1-2}$ on the downstream, that is, the effects caused by exogenous catecholamines or, in theory by endogenous catecholamines after they are released from the sympathoadrenal system. The presently disclosed data does not contradict Messing & Levine, but rather focuses and extend the understanding the role εPKC plays in pain neurotransmission. Furthermore, the findings presented here demonstrate that the anti-hyperalgesic effects of the εPKC inhibitory peptides are also mediated via "the upstream" neurotransmission in the SPGN, and more specifically highlights the effects of the εPKC inhibitory peptides have on the sympathoadrenal system.

This invention shows that administration of a εPKC inhibitor locally at a remote site can inhibit pain by a mechanism that is mediated via the SPGN, and is not limited by nor does it require systemic distribution of the inhibitor throughout the body. The remote action, rapid onset and low doses of the εPKC inhibitor needed to inhibit the pain response require intact nerve since transection of the sciatic and saphenous nerves (de-afferentation) on the contralateral limb blocked the ability of S.C administered εPKC to inhibit pain from a remote site. Furthermore, bilateral lumbar sympathectomy plus bilateral suprarenal ganglionectomy as well as unilateral injection of phentolamine (which is a non-selective α-adrenoceptor antagonist) abolished the pain-reducing effects of εPKC inhibitors.

The very low doses, rapid onset and remote action observed with εPKC inhibitor support the conclusion that perhaps even a much less selective inhibitor of εPKC (including inhibitors that might otherwise be toxic if systemically administered) could be used to suppress a pain response. Furthermore, since we have shown that very low doses of an εPKC administered locally can have this effect, it is conceivable that a similar very low dose of an otherwise non-selective and systemically toxic εPKC inhibitor could be administered locally at very low doses (i.e., much below the dose-limiting systemic toxic levels of that drug) to achieve inhibition of a pain response without producing any or only very limited systemic toxic side effects.

Methods of Use and Formulations

The modified peptides described herein are useful for the prevention and treatment of pain. For the purposes of this discussion, pain, and the treatment thereof, is categorized into different classes: treatment of acute, chronic, neuropathic, and inflammatory pain. The modified εPKC inhibitory peptides described herein are useful for the treatment of acute, chronic, neuropathic, and inflammatory pain.

Interestingly, the compounds disclosed herein are also useful in attenuated or preventing the development of neuropathic pain caused by a plurality of stimuli. For example, as discussed in Example 7 below, chronic inflammatory pain can be induced by the administration of carrageenan followed by the administration of prostaglandin E2. This phenomenon serves as a model for a variety of systems where a subject receiving a plurality of pain stimuli or pain sensitizing agents results in chronic inflammatory or neuropathic pain. It has been noted that chemotherapy patients receiving TAXOL develop neuropathic pain, which typically resolves after the initial dose or doses of the drug. However, chemotherapy patients receive a full course of TAXOL treatments are left with on-going neuropathic pain. The present disclosure contemplates that the administration of the εPKC inhibitory peptides described herein, either prophylactically, with the chemotherapeutic agent, or subsequent to the chemotherapy will be effective to attenuate or prevent the development of the chronic inflammatory or neuropathic pain condition.

Once a cargo/carrier peptide construct has been assembled and tested for increased stability, potency, or both as compared to a prototype, the construct is placed into a pharmaceutically acceptable formulation for administration to a subject prior to, during, or continuously through a pain inducing event.

A "pharmaceutically acceptable formulation" comprises one that is suitable for administering the modified εPKC inhibitor in a manner that gives the desired results and does not also produce adverse side effects sufficient to convince a physician that the potential harm to a patient is greater than the potential benefit to that patient. The components of a suitable pharmaceutically acceptable formulation for use with a modified εPKC inhibitors are determined in part by the route and method of administration. The formulations generally comprise one or more modified εPKC inhibitory peptides incorporated into a pharmaceutically acceptable carrier typically comprising simple chemicals such as sugars, amino acids or electrolytes. Exemplary solutions are typically prepared with saline or buffer. The pharmaceutically acceptable carrier may contain excipients which are well known in the art, and may be used in a variety of formulations. See, e.g., Remington's Pharmaceutical Sciences, 18th Edition, A. R. Gennaro, Editor, Mack Publishing Company (1990); Remington: The Science and Practice of Pharmacy, 20th Edition, A. R. Gennaro, Editor, Lippincott Williams & Wilkins (2000); Handbook of Pharmaceutical Excipients, 3rd Edition, A. H. Kibbe, Editor, American Pharmaceutical Association, and Pharmaceutical Press (2000); and Handbook of Pharmaceutical Additives, compiled by Michael and Irene Ash, Gower (1995).

Inhibitor dosage in the formulation will vary according to a variety of parameters influenced by the stability and potency of the cargo/carrier construct, the route of administration, and desired dosing regime. Daily dosages in the range of 1 μg/kg-100 mg/kg of body weight, preferably 1 μg/kg-1 mg/kg and most preferably 10 μg/kg-1 mg/kg are contemplated.

Modified εPKC inhibitors can be administered locally or systemically. Local administration can be achieved by topical administration, transdermal, intradermal administration, intrathecal administration, intraperitoneal administration, or subcutaneous injection. Systemic administration of a modified εPKC inhibitor is preferably parenteral, although oral, buccal, and intranasal administration is also contemplated. Parenteral administration is generally characterized by injection, either subcutaneously, intramuscularly, intraperitoneal, and intravenously. Injectable forms of the modified inhibitory peptides can be prepared in conventional forms, either as liquid solutions or suspensions, solid (e.g., dried or lyophilized) forms suitable for reconstitution into solution or suspension in liquid prior to injection, or as emulsions. Generally, suitable excipients include, for example, water, saline, dextrose, glycerol, ethanol or the like. In addition, minor amounts of non-toxic auxiliary substances can be employed, such as wetting or emulsifying agents, pH buffering agents, solubility enhancers, tonicifiers and the like including, for example, sodium acetate, sorbitan monolaurate, triethanolamine oleate, cyclodextrins, etc.

The modified εPKC inhibitory peptides can be administered to treat pain as necessary. For prophylaxis, the modified εPKC compound may be administered prior to a pain-inducing event. For example, the peptide can be administered 5, 10, 15, 20, 25, 30, 35, 40, 45, 50, 55 minutes, one hour, several hours, one day, several days, one week, or weeks prior ahead of an anticipated pain-inducing event. Even longer periods of prophylactic administration can be achieved using modified peptides that are particularly stable in vivo, or by using a sustained release formulation of the peptide, e.g. delivery by intrathecal pump.

EXAMPLES

The following examples serve to describe more fully the manner of using the above-described invention, as well as to set forth the best modes contemplated for carrying out various aspects of the invention. It is understood that these examples in no way serve to limit the true scope of this invention, but rather are presented for illustrative purposes. All references cited herein are incorporated by reference in their entirety.

Example 1

Analogs of εPKC Inhibitor Optimization

A prior art εPKC inhibitory sequence (KP-1636) was used as the prototype to study the impacts of various chemical modifications on potency and stability. The prototype sequence, KP-1586 was used as the template in the work described below. Various cargo and carrier peptides were modified for this work, and these are provided in Table 10.

"Tat" in Table 10 refers to the fragment 47-57 of HIV Tat, and "Cap Tat refers to an N-acetyl or C-amide analog of the same peptide. The term "hC" or "hCys" refers to a homocysteine amino acid.

Example 2

Stability of εPKC Inhibitor Analogs

The plasma and chemical stability of various cargo/carrier peptide constructs described in Example 1 was tested. Plasma stability of the compounds was tested using both human and rat sera and the amount of starting material was determined after 30 minutes of treatment. Chemical stability was evaluated by determining the amount of starting material remaining after 9 days of treatment.

TABLE 11

| Compound | Plasma Stability % Remaining at 30 mins | | Chemical Stability % Remain at: |
|---|---|---|---|
| | Human | Rat | 9 days |
| 1586 Lead | 85 | 77 | 57 |
| 1630 Cap cargo/Tat | 76 | 77 | 67 |
| 1631 Overlap 1 | 49 | 67 | 76 |
| 1632 Overlap 2 | 54 | 61 | 89 |
| 1633 Linear | 83 | 77 | 99 |
| 1634 Dimer/cTat | 87 | 106 | 82 |
| 1635 retro-inverso | 63 | 72 | 95 |
| 1636 no caps | 79 | 79 | 27 |
| 1637 halt-HomoCys | 60 | 78 | 100 |
| 1638 full HomoCys | nd | nd | 100 |

Example 3

Time Course Plasma Stability of εPKC Inhibitor Analogs

The plasma stability of various cargo/carrier peptide constructs described in Example 1 was tested using both human and rat sera and the amount of starting material was deter-

TABLE 10

Figure 3:
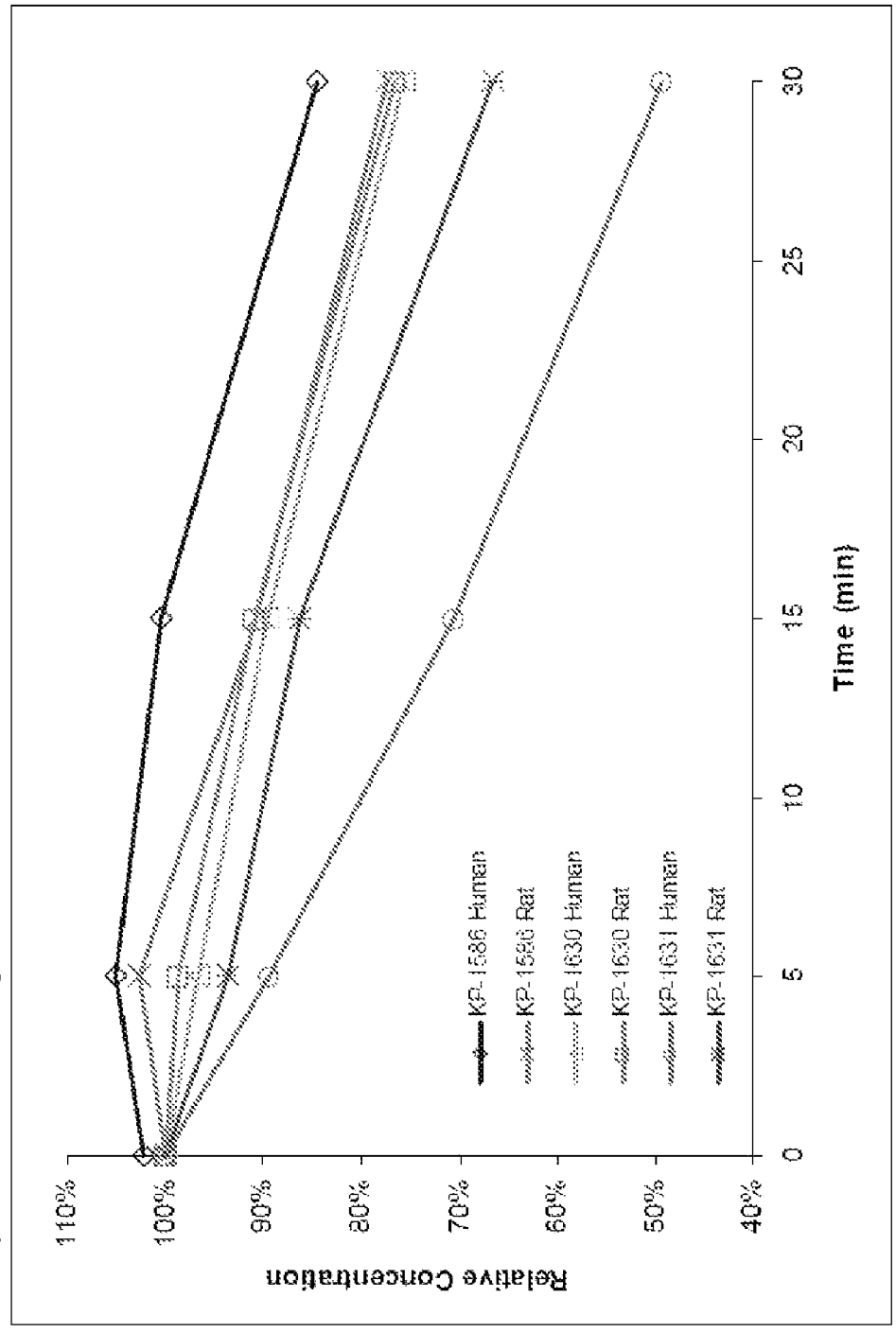
FIG. 3 shows the impact of rat or human sera on the stability of peptides KP-1586, KP-1630, and KP-1631, by plotting the relative concentration of test peptides over time.
Figure 4:
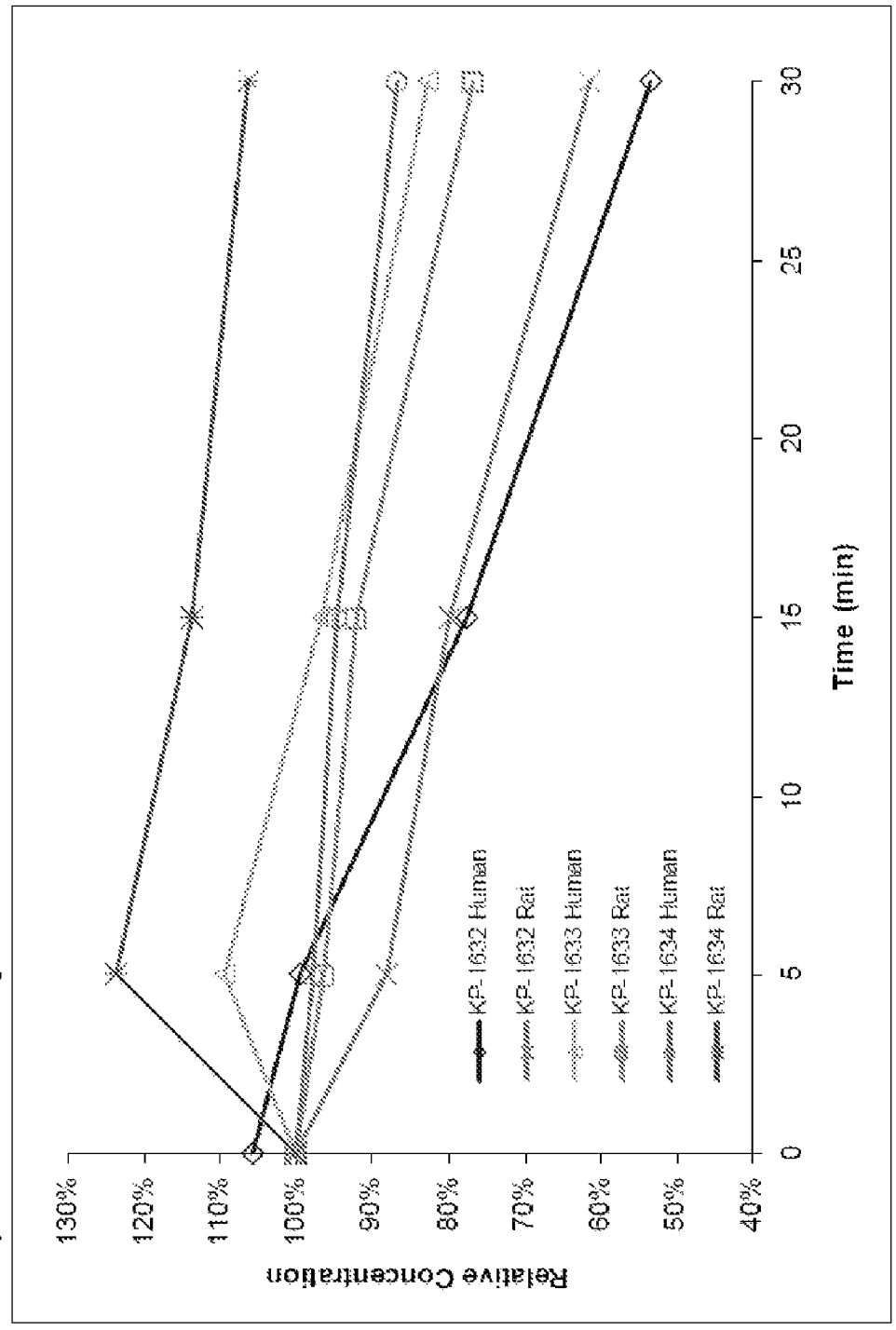
FIG. 4 shows the impact of rat or human sera on the stability of peptides KP-1632, KP-1633, and KP-1634, by plotting the relative concentration of test peptides over time.
Figure 5:
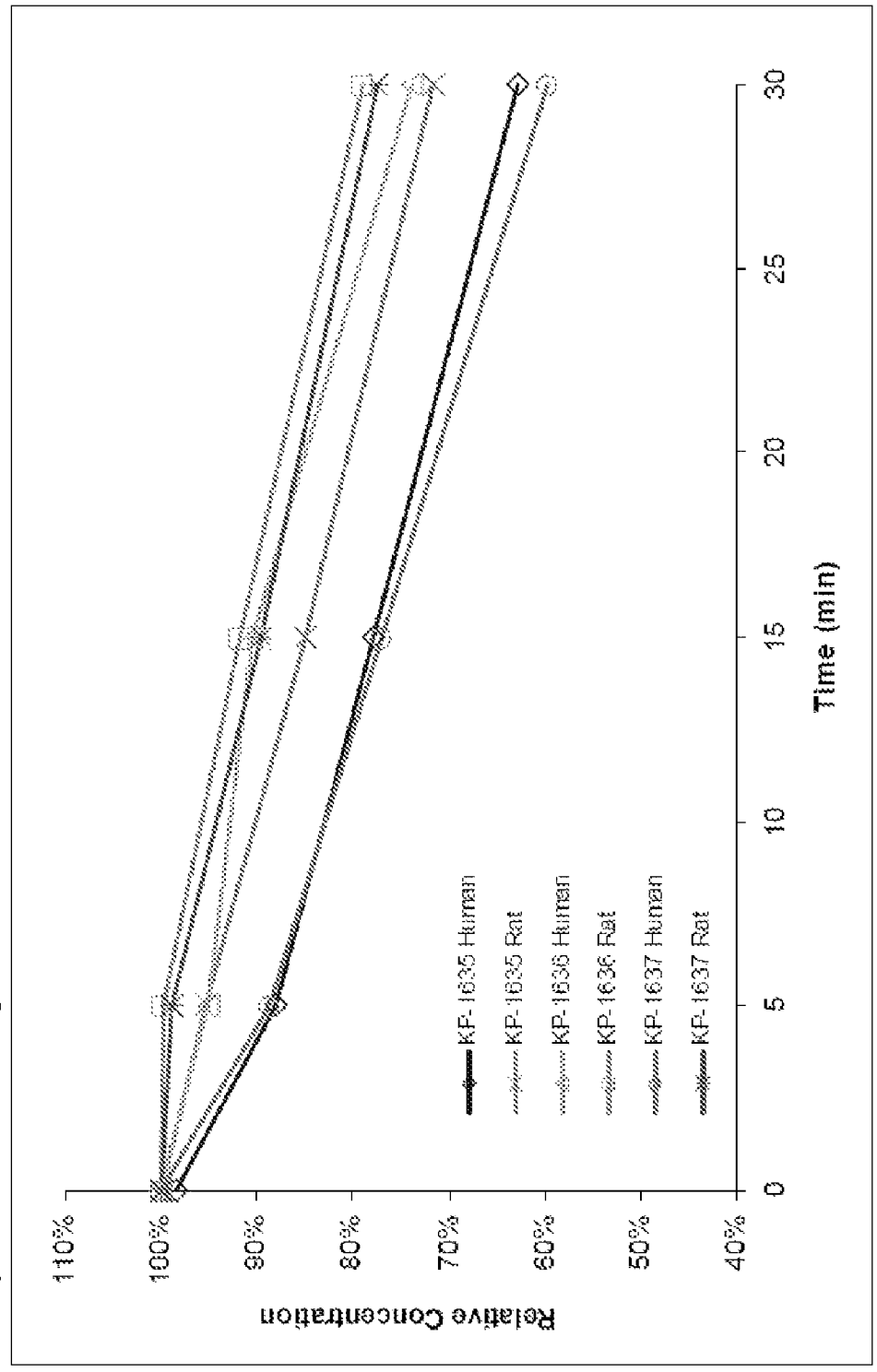
FIG. 5 shows the impact of rat or human sera on the stability of peptides KP-1635, KP-1636, and KP-1637, by plotting the relative concentration of test peptides over time.

| Compound Description | Cargo Peptide Sequences | SEQ ID NO: | Carrier Peptide Description |
|---|---|---|---|
| KP-1586 | C-E-A-V-S-L-K-P-T | 44 | Cap Tat |
| KP-1630 | Ac-C-E-A-V-S-L-K-P-T-NH$_2$ | 45 | Cap Tat |
| KP-1631 | Ac-C-L-K-P-T-A-W-S-L-R-NH$_2$ | 46 | Cap Tat |
| KP-1632 | Ac-C-E-A-V-S-L-K-P-T-A-W-S-L-R | 47 | Cap Tat |
| KP-1633 | E-A-V-S-L-K-P-T-G-G-TaT-NH$_2$ | 48 | Linear |
| KP-1634 | [Ac-E-A-V-S-L-K-P-T-G-G]-K-C | 49 | Cap Tat |
| KP-1635 | t-p-k-l-s-v-a-e-c | 50 | Cap Tat |
| KP-1636 | C-E-A-V-S-L-K-P-T | 51 | Tat |
| KP-1637 | Ac-C-E-A-V-S-L-K-P-T-NH$_2$ | 52 | Ac-hCys-Tat |
| KP-1638 | Ac-hC-E-A-V-S-L-K-P-T-NH$_2$ | 53 | Ac-hCys-Tat |
| KP-1678 | Ac-E-A-V-S-L-K-P-T-G-G-Tat-NH$_2$ | 54 | Linear | mined over time to 30 minutes of treatment. The time course data for cargo/carrier peptides KP-1586, KP-1630, and KP-1631 is shown in FIG. 3, the data for peptides KP-1632, KP-1633, and KP-1634 is shown in FIG. 4, and the data for peptides KP-1635, KP-1636, and KP-1637 is shown in FIG. 5. The dimer peptide and the analog containing an uncapped carrier peptide were more stable that of the prototype material. Interestingly, capping of the cargo peptide had little impact on plasma stability as seen when comparing the stability of KP-1586 and KP-1630.

Example 4

Time Course Chemical Stability of εPKC Inhibitor Analogs

Figure 6:
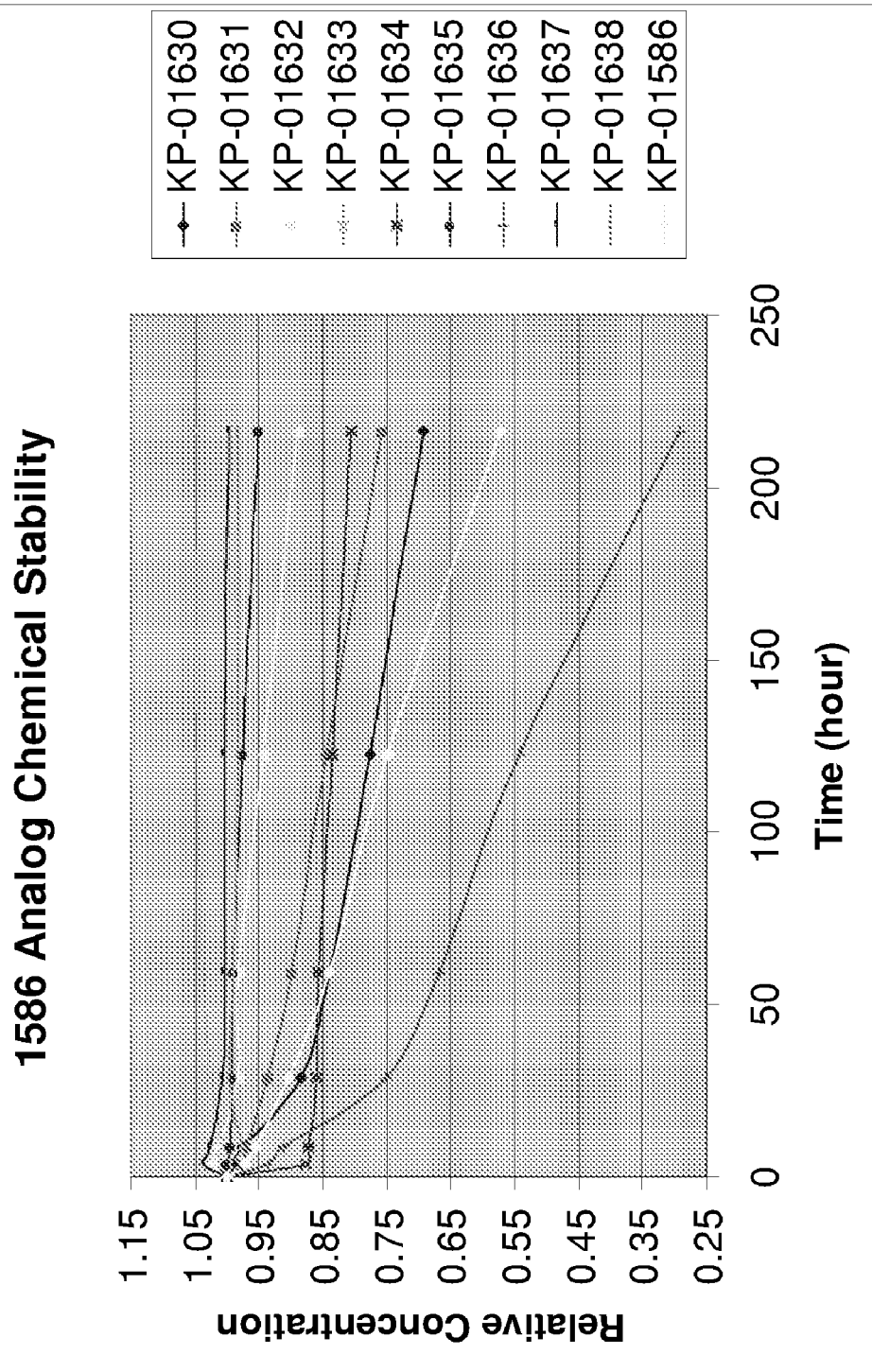
FIG. 6 shows the impact of time and temperature on the chemical stability of peptides KP-1586, KP-1630, KP-1631, KP-1632, KP-1633, KP-1634, KP-1635, KP-1636, KP-1637, and KP-1638, by plotting the relative concentration of test peptides over time.

The chemical stability of various cargo/carrier peptide constructs described in Example 1 was tested by examining the relative concentration of the peptides over a time period of more than 200 hours at 37° C. The time course data for the cargo/carrier peptides is shown in FIG. 6. The data from this study showed that the prototype sequence was only moderately stable as compared to the analogs. Both the linear and homocysteine-containing constructs showed improved stability relative to the prototype sequence. For example, KP-1637 showed marked stability.

Example 5

Attenuation of Acute Pain with a Modified εPKC Inhibitory Peptide

Figure 7:
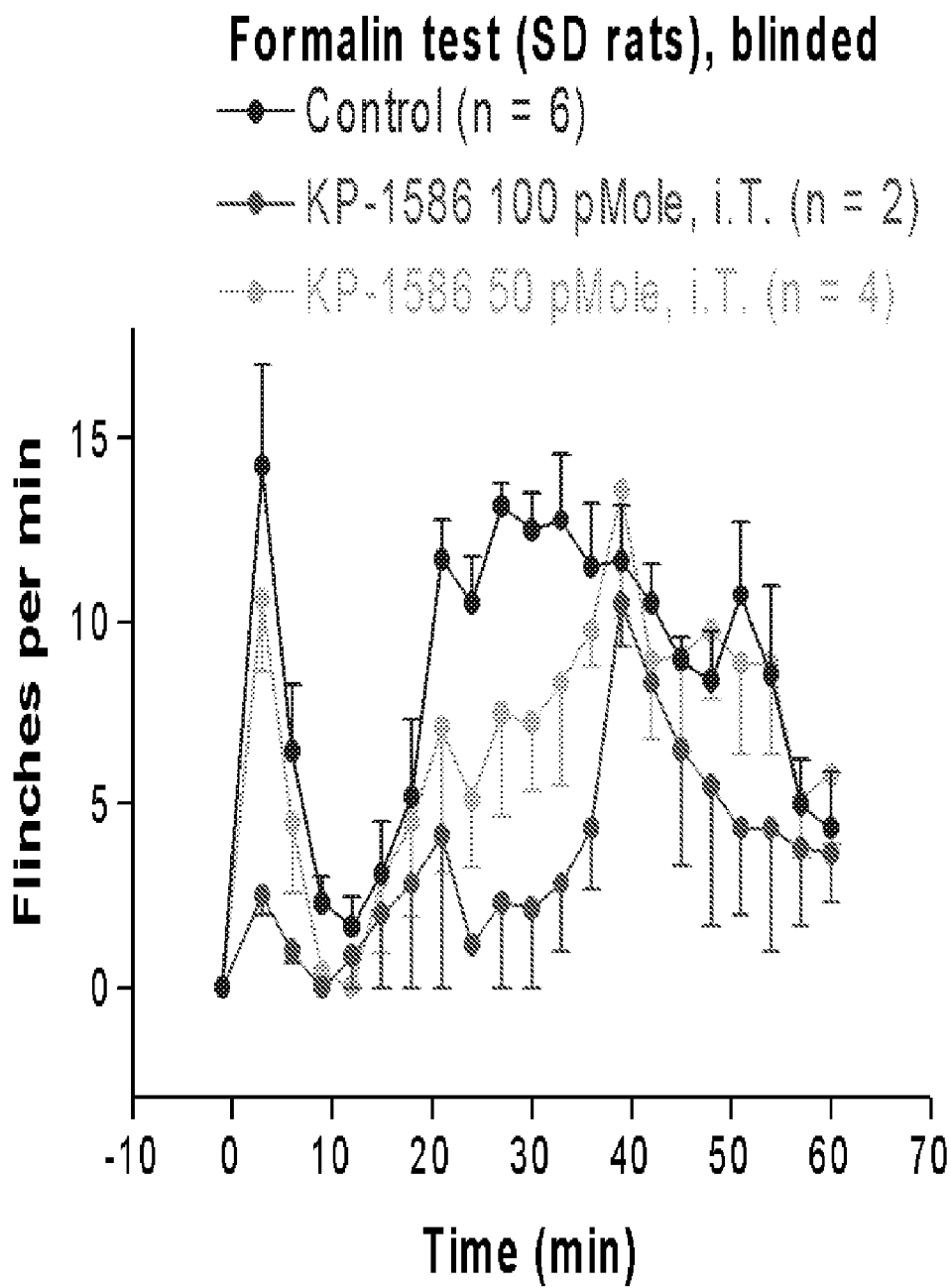
FIG. 7 shows the results of a formalin test to show the attenuation of acute pain in a plot of flinches per minute versus time in rats treated with control and two doses of KP-1586.

A formalin-induced pain test was used to study the ability of a modified εPKC peptide to attenuate acute pain. Formalin was administered by an intraplantar route to all rats used in the present study. Test subjects received a formulation containing modified εPKC peptide KP-1586 by intrathecal administration 15 minutes prior to the pain-causing agent (prophylactic mode). Two different concentrations of the modified peptide were used in the test subjects. The data from this experiment is shown in FIG. 7. The results of this study indicate that the prophylactic administration of the modified εPKC inhibitory peptide was effective to reduce flinches per minute in the test animals. Thus, the administration of modified εPKC peptides is effective to attenuate an acute pain stimulus.

Example 6

Attenuation of Chronic Pain with a Modified εPKC Inhibitory Peptide

Figure 8:
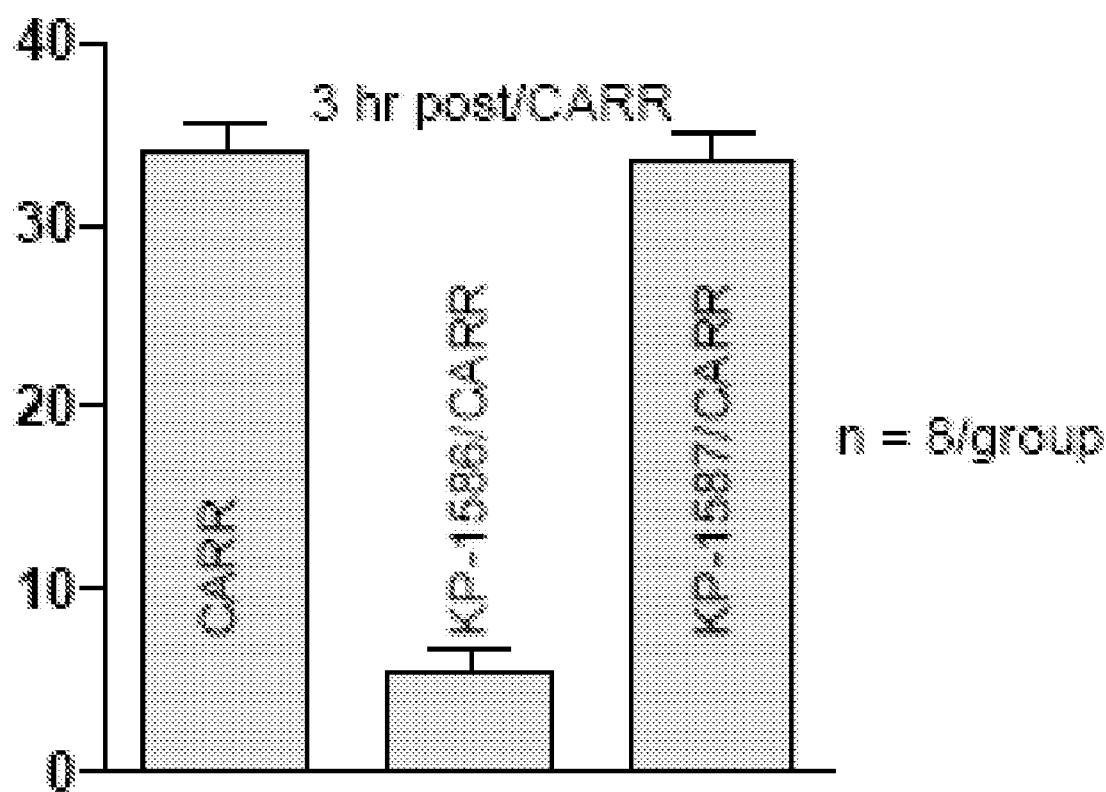
FIG. 8 shows the impact of εPKC inhibitory peptide on acute inflammatory pain in a bar graph plotting paw withdrawal latency for peptide KP-1586 and control peptide KP-1587 in a carrageenan model.

The Chung (L5 nerve transection) is a well-known model for chronic (neuropathic) pain. A representative modified εPKC peptide KP-1586 provided in the disclosure has been efficacious in reducing pain in this model when delivered systemically. The results from this work are shown in FIG. 8.

The test peptide KP-1586, but not the control peptide, suppressed thermal hyperalgesia in a modified Chung's model when delivered for many days by subcutaneous osmotic pump. Such inhibitory effects were dose-dependent, with an initial dose of 10-50 pmol/day. Anti-hyperalgesic effects became detectable as early as the next day after implantation and continued throughout at least one week with continuous compound delivery.

In the same model, chronic sub-cutaneous delivery of KP-1586, but not the control peptide KP-1587, suppressed mechanical allodynia. This inhibition was dose-dependent in some observation windows, particularly in the tests of the 7th day following establishment of the model. Anti-allodynic effects became detectable as early as the day after implantation.

KP-1586 was further able to modify pain responses in the Chung model following intrathecal administration. The efficacy of the drug in this mode lasted at least 90 minutes following single bolus administration.

Example 7

Figure 9:
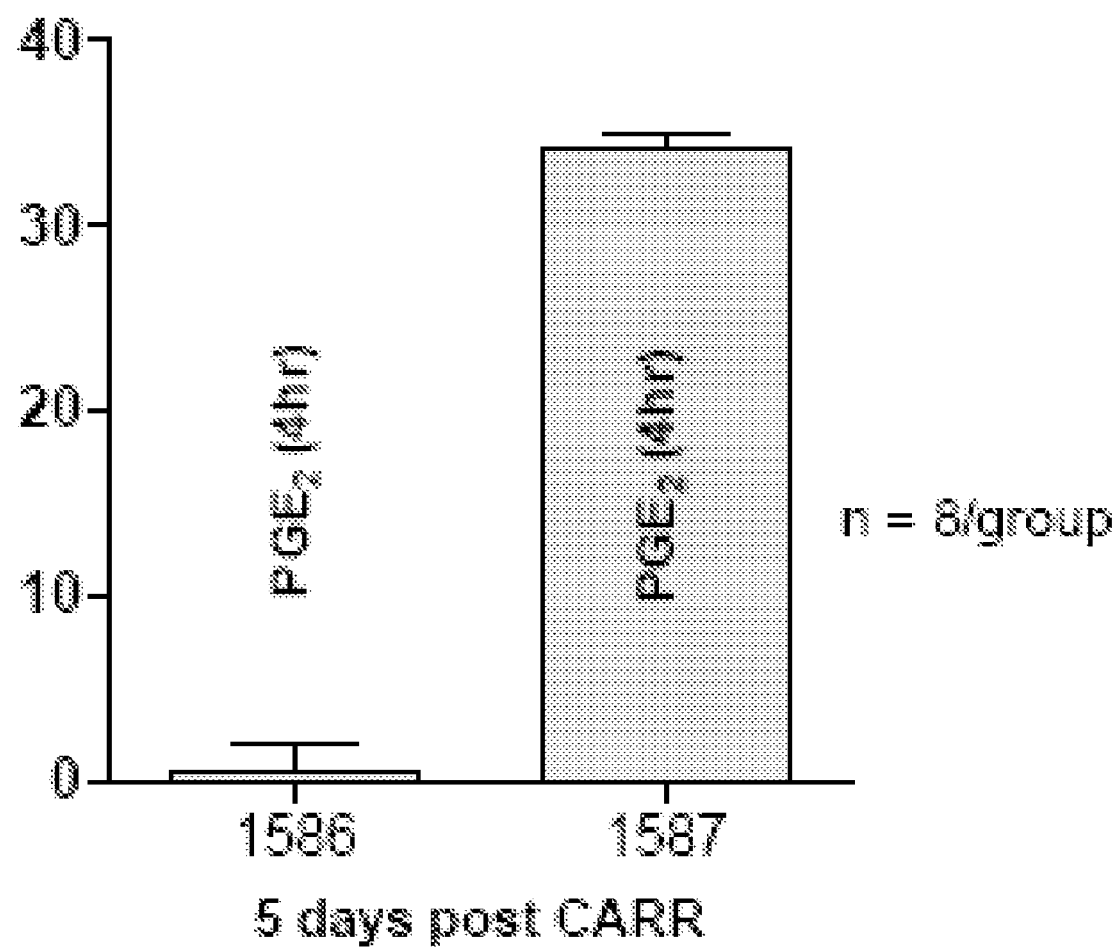
FIG. 9 shows a bar graph plotting paw withdrawal latency and compares impact of inhibitory peptide KP-1586 or control peptide KP-1587 in a chronic inflammatory pain model in rats where carrageenan is administered followed 5 days later by $PGE_2$ to promote chronic hyperalgesia.

Attenuation of Chronic Inflammatory Pain Using a Modified εPKC Inhibitory Peptide The intraplantar administration of carrageenan followed 5 days later with prostaglandin E2 (PGE2) to the rat paw causes both acute and chronic pain through an inflammatory mechanism. As shown in FIG. 9, local delivery of compounds described herein is able to attenuate the development of the pain response.

Representative compound was KP-1586 was able to reverse the painful effects of carrageenan when delivered by intradermal administration while the control peptide KP-1587 did not.

Example 8

Subcutaneous εPKC Inhibitor Reverses Inflammatory Pain

Figure 10:
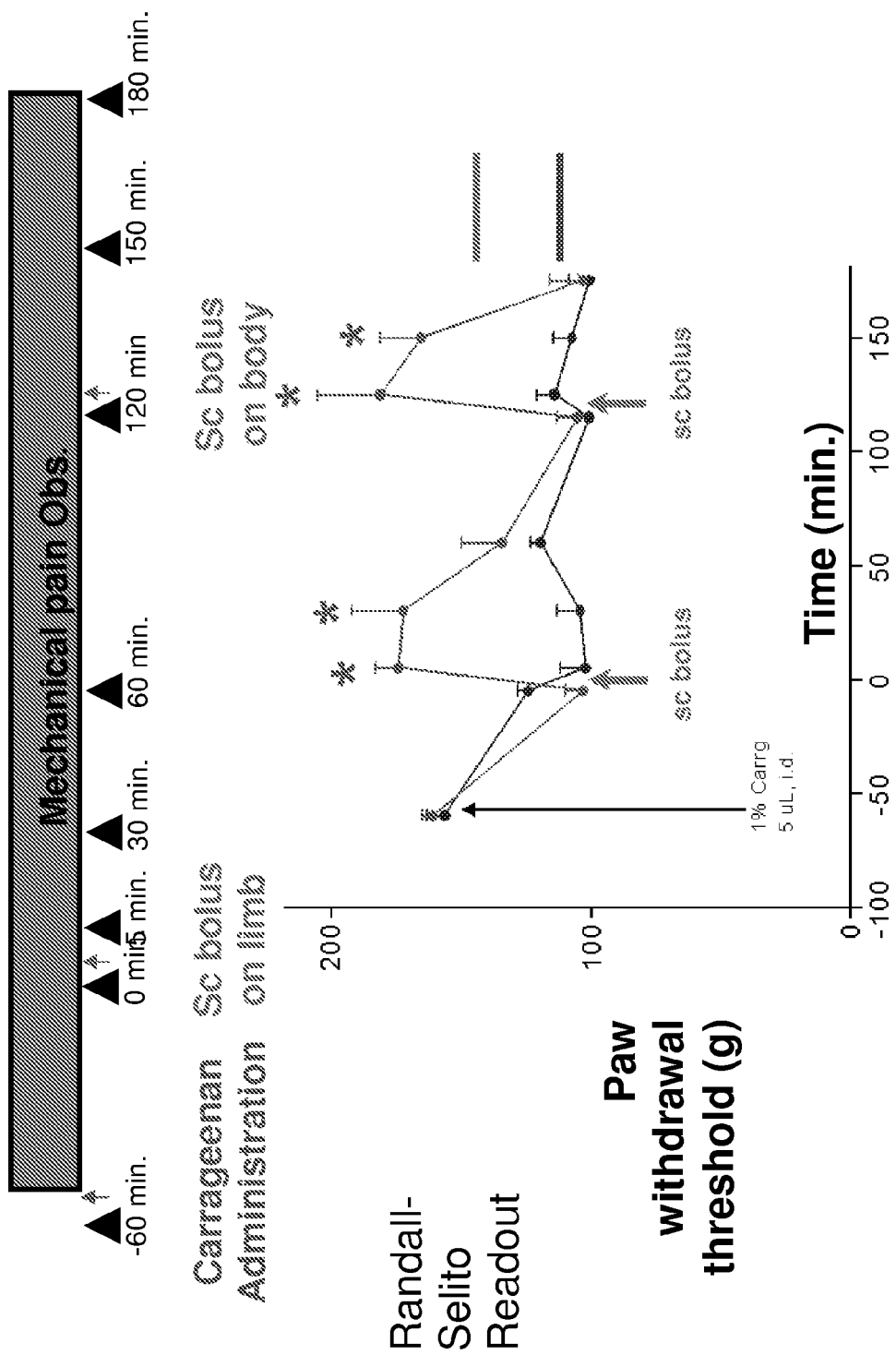
FIG. 10 shows a line plot indicating the effect of a εPKC inhibitory peptide on paw withdrawal threshold measurements.

The intraplantar administration of carrageenan followed 1 hour later with a subcutaneous bolus administration of KP-1634 was tested in a mechanical pain model to demonstrate the effect of εPKC inhibition on paw withdrawal. As shown in FIG. 10, paw withdrawal thresholds increased markedly after the administration of the inhibitor while the control peptide KP-1587 did not induce the same effect.

Example 9

Figure 11:
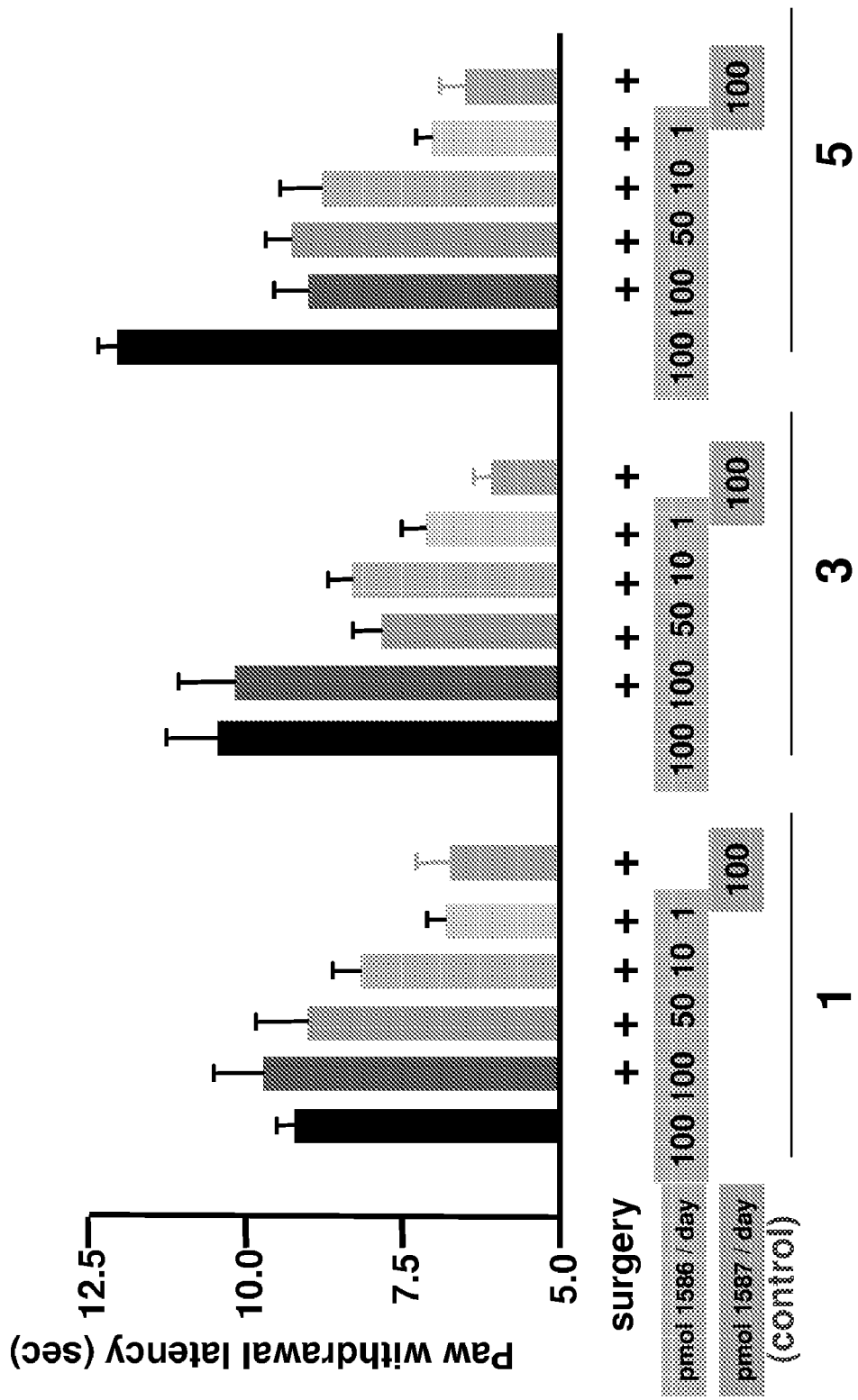
FIG. 11 shows bar graphs of the impact of subcutaneous infusion of a εPKC inhibitory peptide on thermal hyperalgesia in rats following L5 nerve transection (a neuropathic pain model).

Prevention of Neuropathic Pain with Subcutaneous Administration of a εPKC Inhibitory Peptide The εPKC peptide KP-1586 was used in the Chung model to test the ability of εPKC inhibitory peptides administered subcutaneously to prevent neuropathic pain. The test peptides were administered at 1, 10, 50, and 100 pmol/day. The results from this work are shown in FIG. 11.

The test peptide KP-1586, but not the control peptide 1587, suppressed thermal hyperalgesia in a modified Chung's model when delivered by subcutaneous osmotic pump and tested as 1, 3 and 5 days post-surgery.

Example 10

Figure 12:
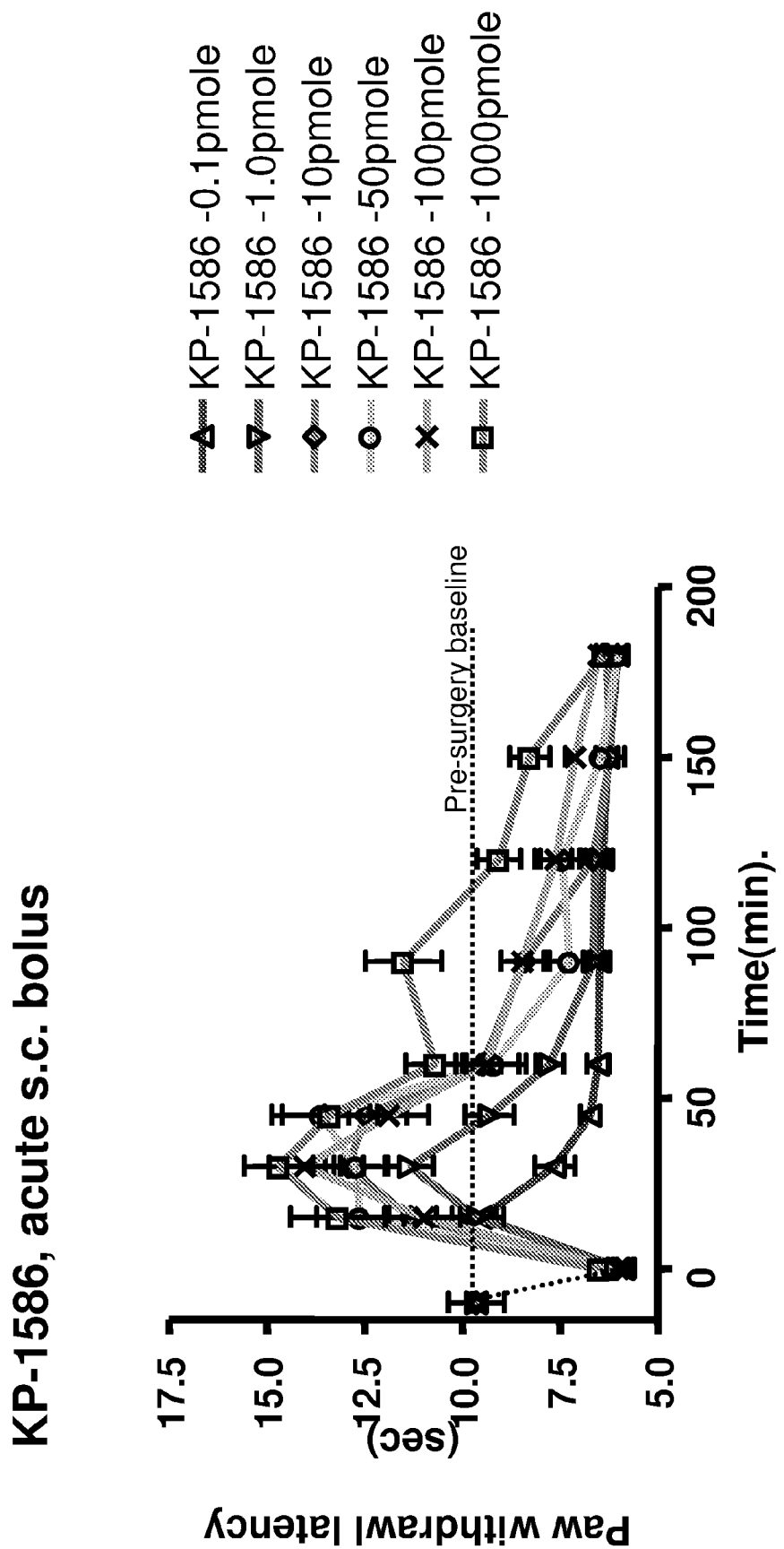
FIG. 12 shows a line plot indicating the impact of a subcutaneous bolus of a εPKC inhibitory peptide on thermal hyperalgesia in rats following L5 nerve transection measured using paw withdrawal latency.
Figure 13:
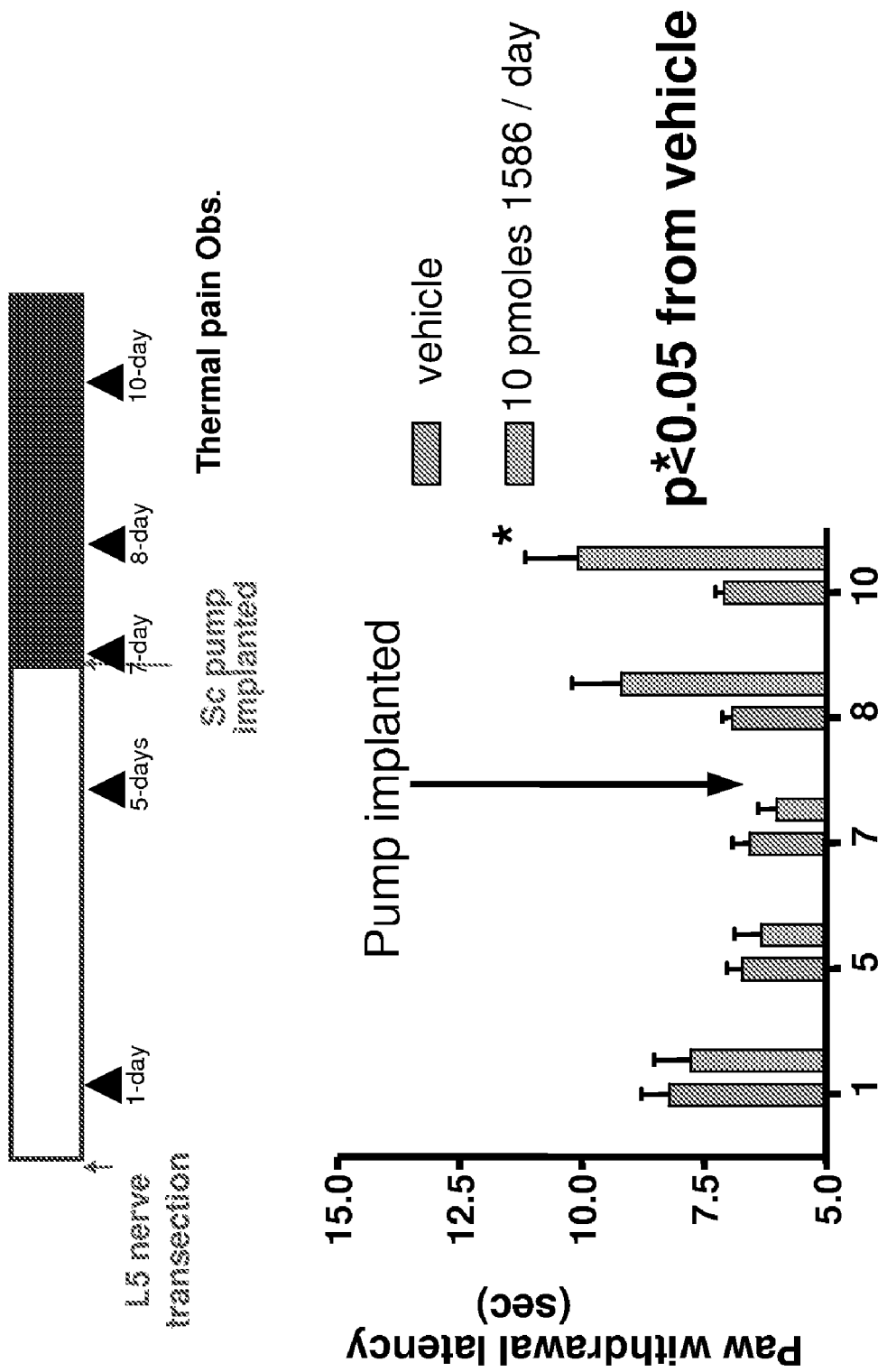
FIG. 13 shows a bar graph indicating the impact of subcutaneous infusion of a εPKC inhibitory peptide on thermal hyperalgesia in rats following L5 nerve transection.
Figure 14:
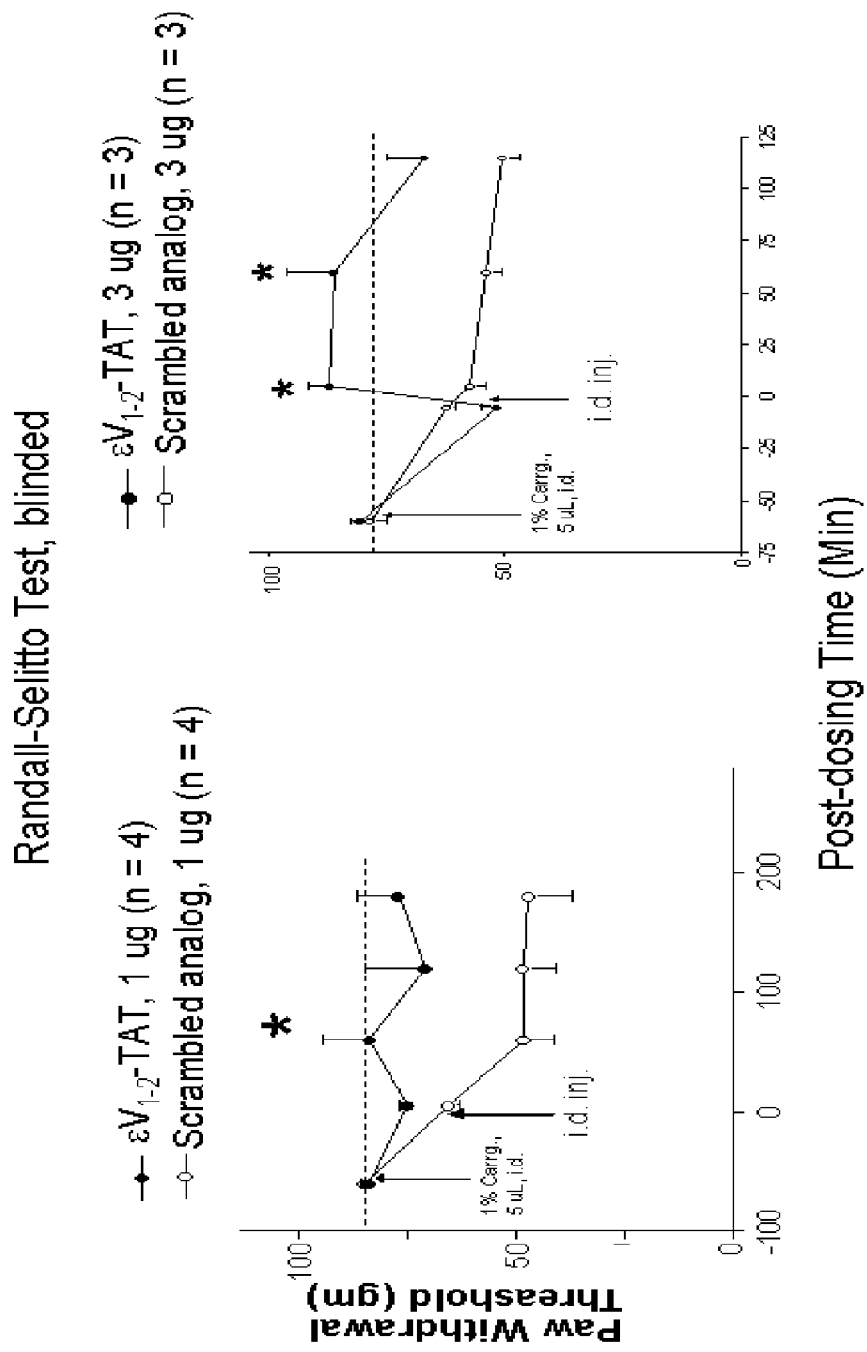
FIG. 14 Effects of local administered εPKC inhibitors on λ-carrageenan-induced hyperalgesia in response to mechanical stimulation. Increases in paw-withdrawal threshold (PWT) upon injection of $εV_{1-2}$ via intradermal (A) and subcutaneous (B) routes. An increase in PWT indicates less pain. An increase in PWT back to the levels before carrageenan referred to anti-hyperalgesic effect. An increase in PWT above the pre-carrageenan levels implicated a potential analgesic effect.
Figure 15:
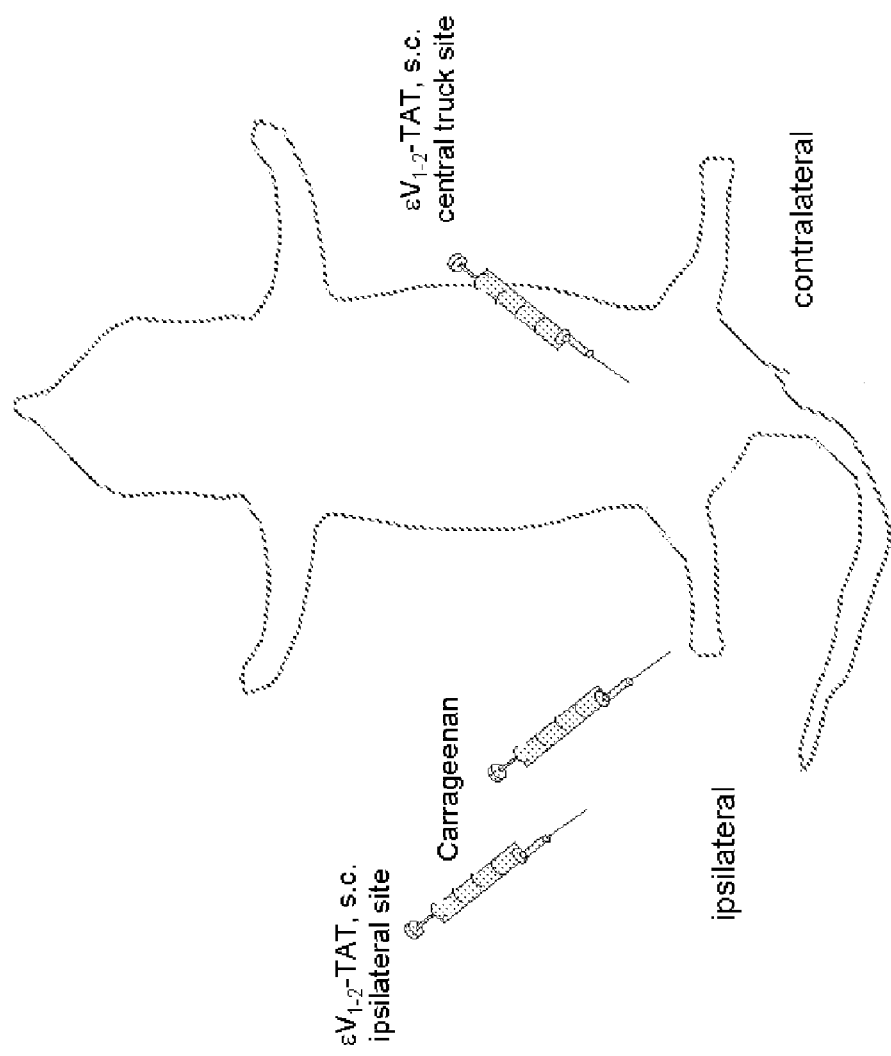
FIG. 15. Effects of unilateral de-afferentation on anti-hyperalgesic effects of εPKC inhibitors administered to the limb on the same side of surgery, distal from the nerve transaction. Intradermal (i.d.) administration of the compound on the ipsilateral paw was still able to inhibit the carageenan-induced pain in the de-afferenated animal.
Figure 16:
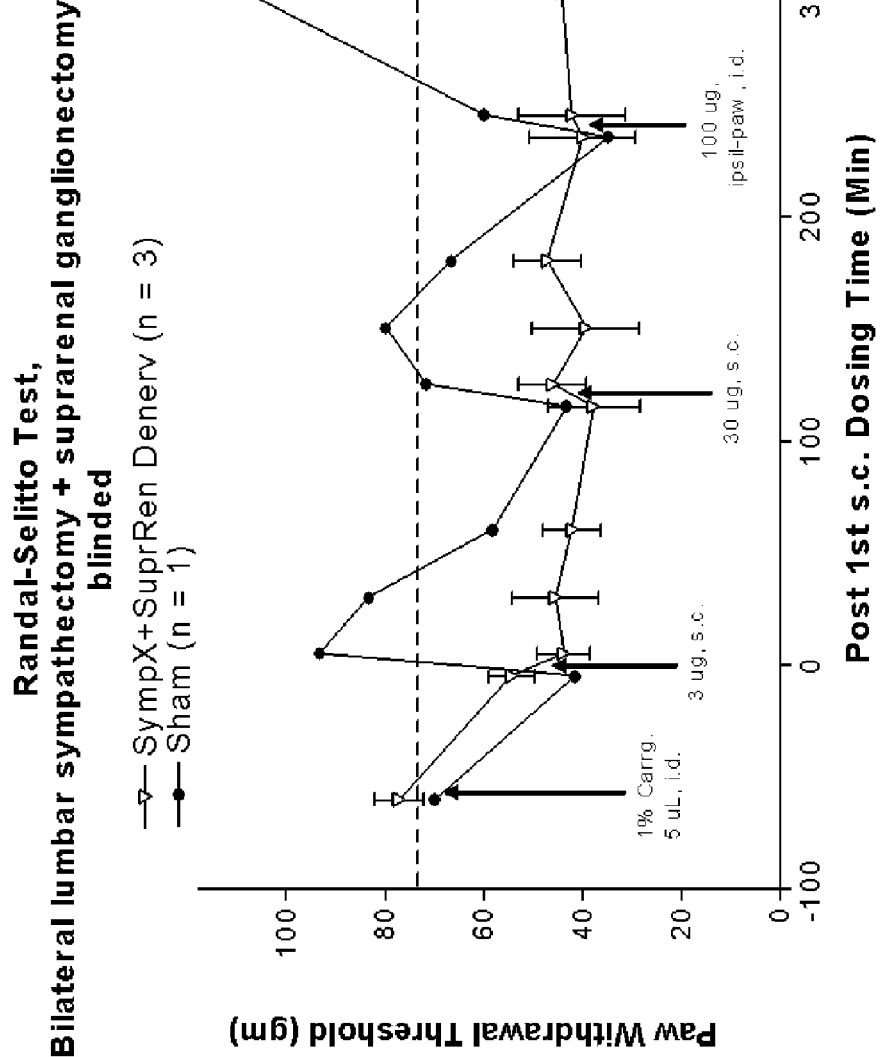
FIG. 16. Effects of bilateral lumbar sympathectomy plus bilateral suprarenal ganglionectomy on anti-hyperalgesic effects of εPKC inhibitors. Experiment was conducted 7-days after surgery to allow degeneration of the SPGN (Sympathetic post-ganglionic neurons) terminals. Surgical sympathectomy mimicked the effects of the unilateral de-afferentation surgery. Subcutaneous injection of an εPKC inhibitor ($εV_{1-2}$-TAT) no longer induced anti-hyperalgesic/analgesic effects in the sympathectomized rats but its effects on the sham surgery animal remained intact. The reversal of hyperalgesic is very rapid within five minutes of administering the εPKC inhibitor.

Reversal of Neuropathic Pain with Subcutaneous Administration of a εPKC Inhibitory Peptide The εPKC peptide KP-1586 was used in the Chung model to test the ability of εPKC inhibitory peptides administered subcutaneously to reverse neuropathic pain. The test peptides were administered at 0.1, 1, 10, 50, 1000 pmol/day. The results from this work are shown in FIG. 12. FIG. 13 shows the effect of an inhibitor administered at 10 pmole per day by subcutaneous infusion with the pump being implanted 7 days after the transection event.

Example 11

The Role of Sympathetic Terminals in Suppressing Carrageenan-Induced Mechanical Hyperalgesia by Inhibitors of PKC Epsilon in Rats λ-carrageenan (Carr)-induced inflammatory pain involves activity of the sympathetic nervous system. Since the sympathetic neurons, like the sensory neurons, are rich in the epsilon isozyme of protein kinase C (εPKC), and since εPKC inhibitors reduce Carr-induced mechanical hyperalgesia, it is hypothesized that the mechanism of action for εPKC inhibitors requires the sympathetic post-ganglionic nerve (SPGN) terminals.

The nociceptive flexior reflex was quantified on lightly restrained rats by using a Basile Analgesymeter (Randall-Selitto test). Inflammatory hyperalgesia was induced by injection of Carr (1%, 5 uL, i.d.), which was injected unilaterally to the dorsum of the hindpaw one-hour prior to compound administration. The εPKC inhibitor peptide (εV1-2) was injected via systemic routes.

Subcutaneous injection of εV1-2 dose-dependently suppressed Carr-induced mechanical hyperalgesia, independent of the site of administration (ipsilateral or contralateral hindlimb or the dorsal trunk).

In contrast, when εV1-2 was administered subcutaneously distal to a transection of the sciatic and saphenous nerves, there was no longer suppression of Carr-induced mechanical hyperalgesia of the contralateral paw. This result suggested that tonic neuronal signaling in these nerves may be the site of action for εV1-2. Furthermore, surgical removal of bilateral lumbar sympathetic chain (L2-L4) and bilateral suprarenal ganglia 7-day prior to the experiment completely abolished anti-hyperalgesic effects of εV1-2. The effect of the surgical sympathectomy was mimicked by acute treatment with adrenergic antagonists such as phentolamine (10 ug, s.c. injection to the contralateral limb, just before Carr injection).

Results from the current study suggest a mechanism of action for εPKC and demonstrate anti-hyperalgesic effects of systemically-delivered εV1-2. These results support the potential development of εPKC inhibitors as novel therapies for inflammatory pain.

Example 12

Modulation of Pain Responses Using Peptides for Selective Modulation of Protein Kinase C It is known that λ-carrageenan (Carr)-induced inflammatory pain involves activity of the sympathetic nervous system. Since the sympathetic neurons, like the sensory neurons, are rich in the ε isozyme of protein kinase C (εPKC), and since εPKC inhibitors reduce Carr-induced mechanical hyperalgesia, it is hypothesized that the mechanism of action for εPKC inhibitors requires the sympathetic post-ganglionic nerve (SPGN) terminals.

The nociceptive flexior reflex was quantified on lightly restrained rats by using a Basile Analgesymeter (Randall-Selitto test). Inflammatory hyperalgesia was induced by injection of Carr (1%, 5 uL, i.d.), which was injected unilaterally to the dorsum of the hindpaw one-hr prior to compound administration. The εPKC inhibitor peptide ($\epsilon V_{1-2}$) was injected via systemic routes.

Subcutaneous injection of $\epsilon V_{1-2}$ dose-dependently suppressed Carr-induced mechanical hyperalgesia, independent of the site of administration (ipsilateral or contralateral hindlimb or the dorsal trunk).

In contrast, when $\epsilon V_{1-2}$ was administered subcutaneously distal to a transection of the sciatic and saphenous nerves, there was no longer suppression of Carr-induced mechanical hyperalgesia of the contralateral paw. This result suggested that tonic neuronal signaling in these nerves may be the site of action for $\epsilon V_{1-2}$. Furthermore, surgical removal of bilateral lumbar sympathetic chain ($L_2$-$L_4$) and bilateral suprarenal ganglia 7-day prior to the experiment completely abolished anti-hyperalgesic effects of $\epsilon V_{1-2}$. The effect of the surgical sympathectomy was mimicked by acute treatment with adrenergic antagonists such as phentolamine (10 ug, s.c. injection to the contralateral limb, just before Carr injection). See FIGS. 14-17.

Example 12

Nonclinical Pharmacology of KAI-1678

The ability of KAI-1678 to reduce allodynia, the heightened response to normally innocuous stimuli, and hyperalgesia, the heightened response to painful stimuli, has been evaluated in rat models of inflammatory pain (carrageenan-induced pain) and neuropathic pain (L5 spinal nerve transection). In the carrageenan-induced inflammatory pain model, local intradermal administration of KAI-1678 has been shown to be effective at reducing mechanical hyperalgesia. However, intradermal administration of KAI-1678 to a remote site was equally effective; suggesting that local administration of KAI-1678 could provide system-wide pain relief. This conclusion is supported by the observation that KAI-1678 is effective with subcutaneous administration, either as a bolus or as a prolonged infusion, to any site on the animal, including those distant from the site of carrageenan injection. Although KAI-1678 appears to have system-wide activity, intravenous infusion of the compound, even at dose rates sufficient to achieve plasma steady-state levels 5- to 10-fold greater than those measured at the end of subcutaneous infusions that achieve maximal efficacy, does not inhibit carrageenan-induced mechanical hyperalgesia. Elucidation of the site-of-action for KAI-1678 is ongoing, but two observations help to define the target of the compound. Surgical disruption of the sciatic and saphenous nerves on the opposite hindlimb from the site of carrageenan injection abrogates the activity of compound administered distal, but not proximal, to the site of nerve disruption, suggesting a requirement for functional innovations of the injection site for the compound to achieve efficacy. Further studies indicate that an intact sympathetic nervous system and α adrenergic receptor signaling is required for KAI-1678 to be active when administered distant from the site of injury. One hypothesis arising from these studies is that KAI-1678 acts on local nerves at the site of injection, perhaps within the dermis or epidermis, and, by an unidentified mechanism, elicits a descending pain-suppressing signal that is dependent on α adrenergic receptor signaling.

Results similar to those obtained in the carrageenan-induced inflammatory pain model were obtained in the L5 spinal nerve transection mononeuropathic pain model used to investigate the efficacy of KAI-1678 in neuropathic pain. In the L5 spinal nerve transection mononeuropathic pain model subcutaneous administration of KAI-1678 caused a reduction in the level of injury-induced allodynia. However, although KAI-1678 was active in both neuropathic pain models, the maximum response and the dose required to achieve maximal response varied substantially in the two models. In these studies, the injury induced by L5 nerve transection appeared to be much more susceptible to treatment with KAI-1678 in that complete reversal of injury-induced allodynia was achieved with low total doses of compound administered either as a subcutaneous bolus or infusion.

Taken together, the nonclinical pharmacology studies support the activity of KAI-1678 in inflammatory and neuropathic pain. These studies also suggest that the maximum effect and the dose required to achieve maximum effect may vary depending on the type and source of injury causing the pain. Efforts are ongoing to identify the site of action and the mechanism of action in each of these models.

Activity of KAI-1678 in the Carrageenan Inflammatory Pain Model

The rat carrageenan model has been extensively used to evaluate the response to modulators of inflammatory pain. In the model used for the studies described below, a single 5 microL injection of a 1% solution of carrageenan into the plantar surface of the right hindpaw was used to elicit an inflammatory response resulting in local edema and mechanical hyperalgesia. The mechanical hyperalgesia was quantitated as previously described using measurements of the nociceptive flexion reflex (Randall-Selitto paw-withdrawal test) in response to mechanical painful stimulation at the site of carrageenan injection. Under the conditions used in these studies, the paw withdrawal threshold (PWT) in the Randall-Selitto test typically decreased from ~90 g prior to carrageenan injection to ~55 g measured 1 hour after carrageenan injection for the untreated animals. In the absence of further treatment, the PWT remained stable at ~55 g for several hours, making it possible to use this model to evaluate the time-course of the response to treatment over the course of at least six hours after the establishment of the disease state.

Intradermal Administration of KAI-1678

Figure 18:
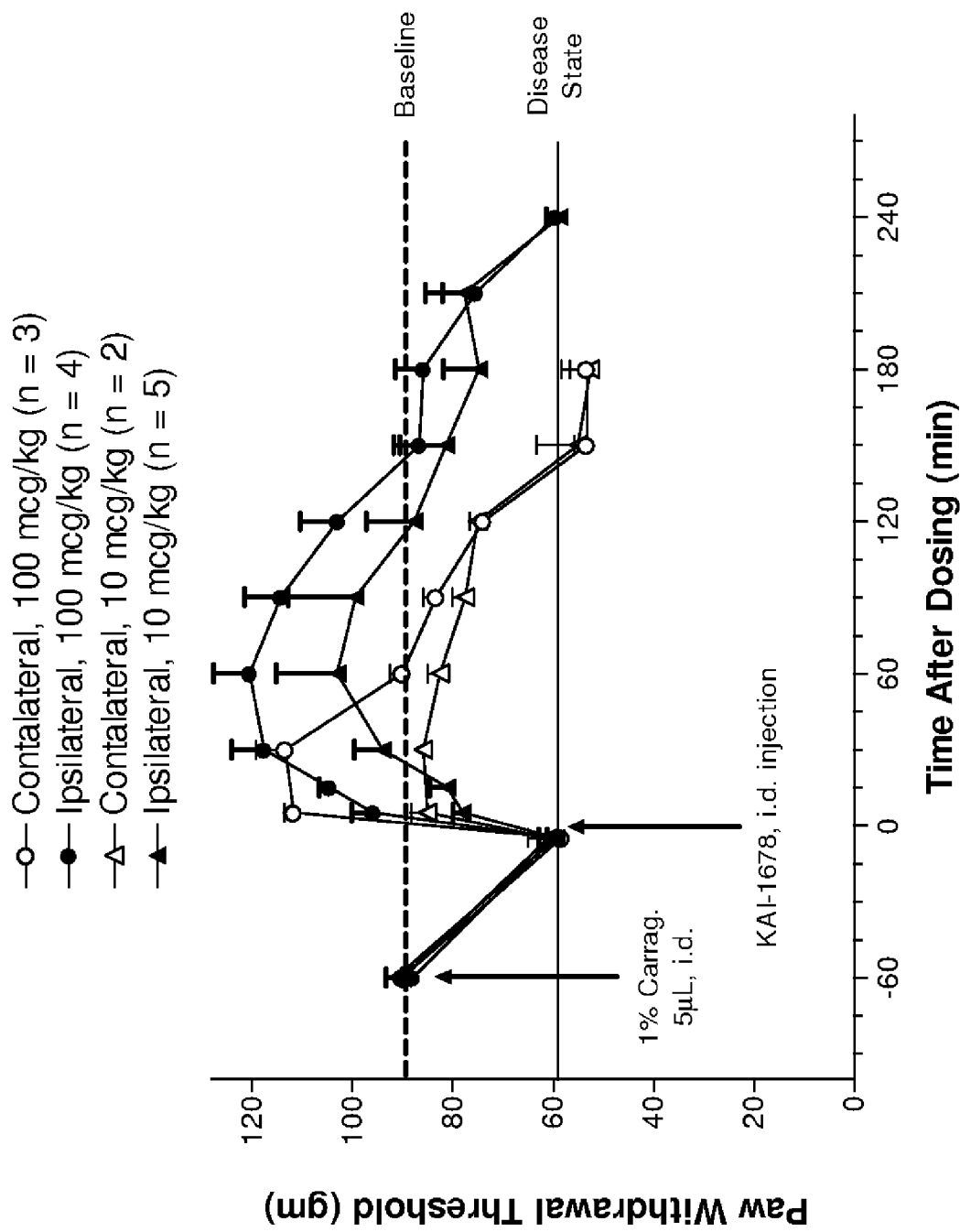
FIG. 18: Effects of Intradermal KAI-1678 on Mechanical Hyperalgesia in the Carrageenan Inflammatory Pain Model in Rats. Rats were treated with an intradermal bolus injection of KAI-1678 60 minutes after carrageenan injection into the plantar side of the right hindpaw. KAI-1678 was dosed at 10 mcg/kg (triangles) or 100 mcg/kg (circles) to either the ipsilateral hindlimb (i.e. the same limb that received carrageenan, filled symbols) or the contralateral hindlimb (i.e. the limb that did not receive carrageenan, open symbols). Data are presented as mean±SEM (standard error of the mean) for the (PWT) measurements for the animals in each group (N=2-5 animals/group) at a given time point. The dotted line at ~90 g represents the pre-carrageenan baseline PWT measurement; PWT indicative of the disease state is ~60 g. Measurements at or above the pre-carrageenan baseline level indicate complete reversal of carrageenan-induced mechanical hyperalgesia.

Previous publications have reported that local intradermal administration of analogs of KAI-1678 is efficacious in the carrageenan-induced inflammatory pain model. To determine whether intradermal administration of KAI-1678 was active in this model, rats injected with carrageenan into the right hindpaw were treated one hour later with an intradermal injection of 10 or 100 mcg/kg of KAI-1678 either on the same (ipsilateral) hindpaw injected with the carrageenan or the other (contralateral) hindpaw. As shown in FIG. 18, intradermal administration of 10 mcg/kg KAI-1678 to the ipsilateral site was able to completely reverse the mechanical hyperalgesia as indicated by the fact that the PWT returned to pre-carrageenan levels. Administration of 100 mcg/kg KAI-1678 to the ipsilateral site was more effective than the 10 mcg/kg dose, increasing the PWT beyond the pre-carrageenan levels and maintaining the PWT at or above pre-carrageenan levels for a longer period. Strikingly, the effect of KAI-1678 demonstrated a rapid onset of action with the mechanical hyperalgesia substantially reversed five minutes after administration of the 10 mcg/kg dose and completely reversed by the 5-min time point following administration of the 100 mcg/kg dose.

Intradermal administration of KAI-1678 to the contralateral hindpaw was also able to completely reverse the mechanical hyperalgesia, with the maximum extent of reversal at each dose similar to that seen for the same dose administered to the ipsilateral hindpaw (FIG. 18). Of note, as in the case in which KAI-1678 was administered close to the site of carrageenan injection, intradermal administration of KAI-1678 to the contralateral paw resulted in a rapid onset of action with near or complete reversal of mechanical hyperalgesia at the 5-min time point for the lower and higher doses, respectively. There was, however, a difference in the duration of the effect with the effect being more prolonged at both dose levels when KAI-1678 was administered to the ipsilateral hindpaw as compared to the contralateral hindpaw.

While the efficacy of local (ipsilateral) administration of selective peptidic εPKC inhibitors structurally related to KAI-1678 has been reported previously, the demonstration that intradermal administration of KAI-1678 to the contralateral hindpaw was similarly efficacious was not anticipated. This result suggests that local administration of KAI-1678 at a remote site may elicit system-wide pain suppression based on its ability to reduce mechanical hyperalgesia in an inflammatory pain model.

Subcutaneous Administration of KAI-1678

Figure 19:
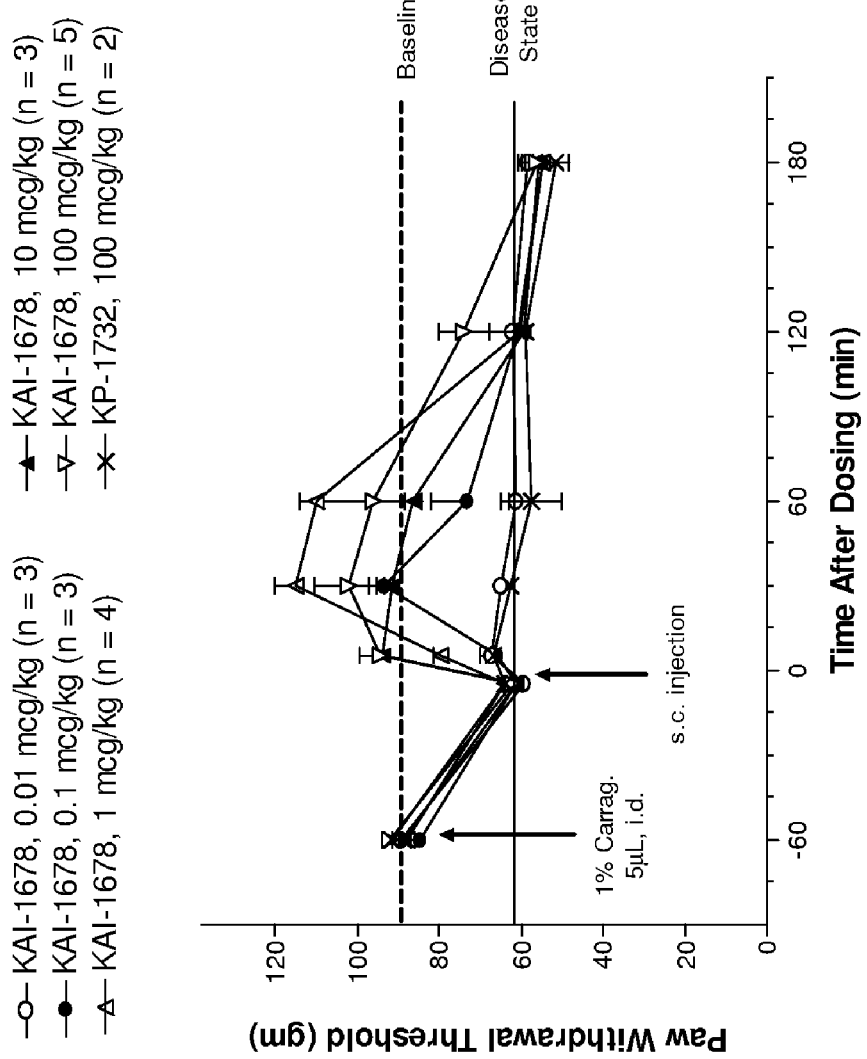
FIG. 19: Effects of Subcutaneous Bolus Administration of KAI-1678 on Mechanical Hyperalgesia in the Carrageenan Inflammatory Pain Model in Rats. A subcutaneous bolus injection of KAI-1678 or KP-1723, the inactive analog of KAI-1678, was administered to rats 60 minutes after carrageenan injection into the plantar side of the right hindpaw. KAI-1678 or KP-1723 was dosed at the indicated doses to the contralateral hindlimb (i.e., the limb that did not receive the carrageenan). Data are presented as mean±SEM (standard error of the mean) for the (PWT) measurements for the animals in each group (N=2-5 animals/group) at a given time point. The dotted line at ~90 g represents the pre-carrageenan baseline PWT measurement; PWT indicative of the disease state is ~62 g. Measurements at or above the pre-carrageenan baseline level indicate complete reversal of carrageenan-induced mechanical hyperalgesia.

KAI-1678 was administered subcutaneously to test whether administration of the compound by this route could suppress mechanical hyperalgesia in the carrageenan inflammatory pain model. As shown in FIG. 19, subcutaneous bolus administration of KAI-1678 on the thigh of the contralateral hindlimb caused a dose-dependent suppression in the pain response, with a dose as low as 0.1 mcg/kg completely reversing mechanical hyperalgesia for a short period of time. At doses up to 100 mcg/kg the duration of the response increased. However, at doses greater than 100 mcg/kg the duration of the response decreased as the dose increased, suggesting a parabolic dose-response for duration.

A group of animals was also dosed with 100 mcg/kg of KP-1723, the inactive control peptide (see above). As shown in FIG. 19, KP-1723 had no effect on mechanical hyperalgesia, indicating that the effects seen with KAI-1678 are not a consequence of non-specific effects of the carrier moiety.

Figure 20:
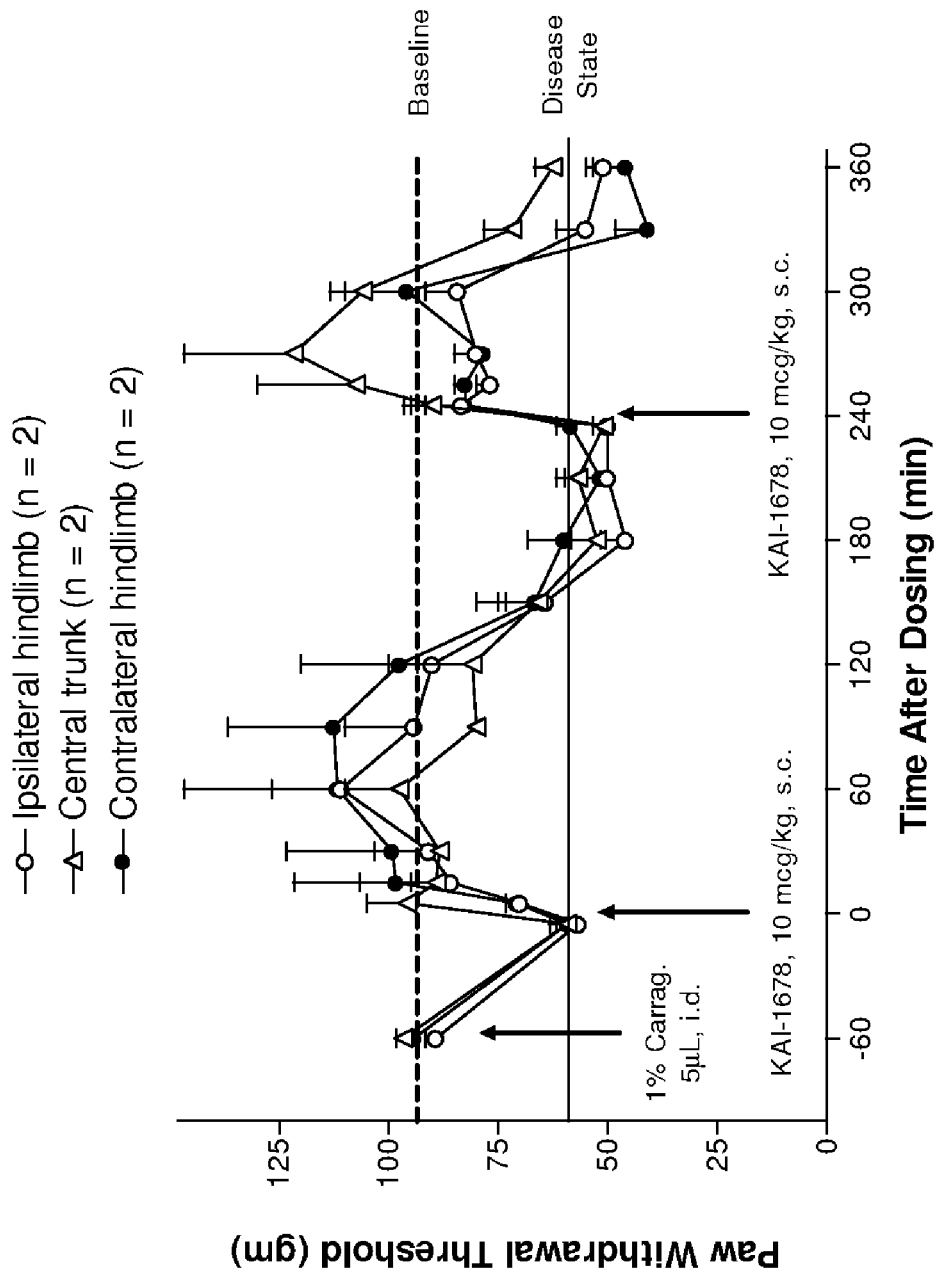
FIG. 20: Effect of Dosing Location on Activity of Subcutaneous Bolus Administration of KAI-1678 in the Rat Carrageenan Inflammatory Pain Model. Rats injected with carrageenan into the plantar surface of the right hindpaw were given two 10 mcg/kg subcutaneous bolus injections of KAI-1678 four hours apart beginning 60 minutes after carrageenan injection. The two doses of KAI-1678 were made to different sites on the rats as indicated. Data are presented as mean±SEM (standard error of the mean) for the (PWT) measurements for the animals in each group (N=2 animals/group) at a given time point. The dotted line at ~90 g represents the pre-carrageenan baseline PWT measurement; PWT indicative of the disease state is ~60 g. Measurements at or above the pre-carrageenan baseline level indicate complete reversal of carrageenan-induced mechanical hyperalgesia.

To determine whether the location at which KAI-1678 is administered as a subcutaneous bolus affects its activity in this model, carrageenan-injected rats were given a 10 mcg/kg subcutaneous bolus of KAI-1678 either on the ipsilateral hindlimb close to the site of carrageenan injection, on the contralateral hindlimb, or on the central trunk above the contralateral hindlimb one hour after carrageenan injection. Four hours later, each animal was given a second 10 mcg/kg subcutaneous administration of compound to a different location as a control for possible animal-to-animal variability. The results shown in FIG. 20 indicate that the efficacy of the first dose of compound was similar regardless of the site of compound administration, and that duration of the response with the second dose was reduced relative to the first administration. This latter observation suggests that repeated subcutaneous bolus administrations may result in tachyphylaxis. Consistent with this observation, repeat administration of an ☐PKC inhibitor analog of KAI-1678 has shown a reduction in both the magnitude and duration of the response that is inversely correlated with the length of time between administrations (data not shown). The basis for the apparent tachyphylaxis is under investigation.

Figure 17:
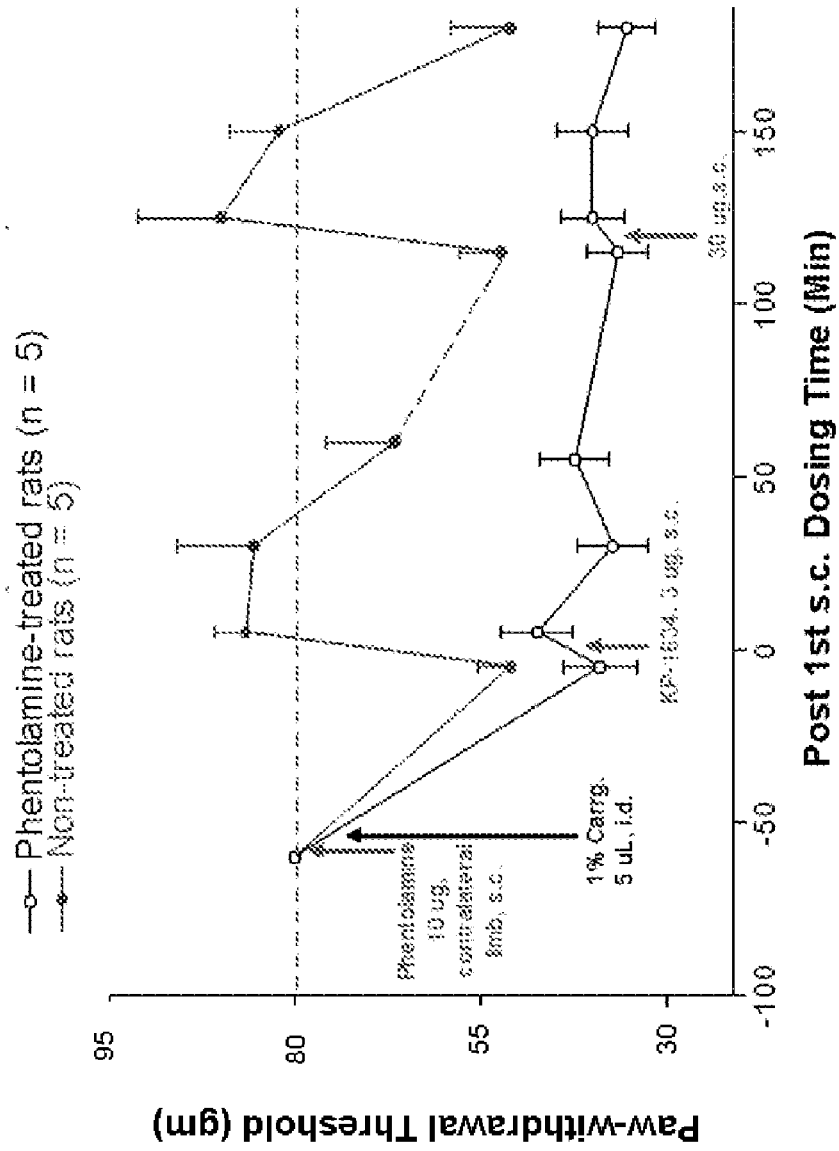
FIG. 17. Effects of injection of phentolamine on anti-hyperalgesic effects of εPKC inhibitors. Injection of phentolamine, which is a non-selective α-adrenoceptor antagonist, abolished the pain-reducing effects of εPKC inhibitor ($εV_{1-2}$-TAT) injected to the distal aspect of the limb injected previously with phentolamine. After phentolamine, the anti-hyperalgesic effects of $εV_{1-2}$-TAT was lost.
Figure 21:
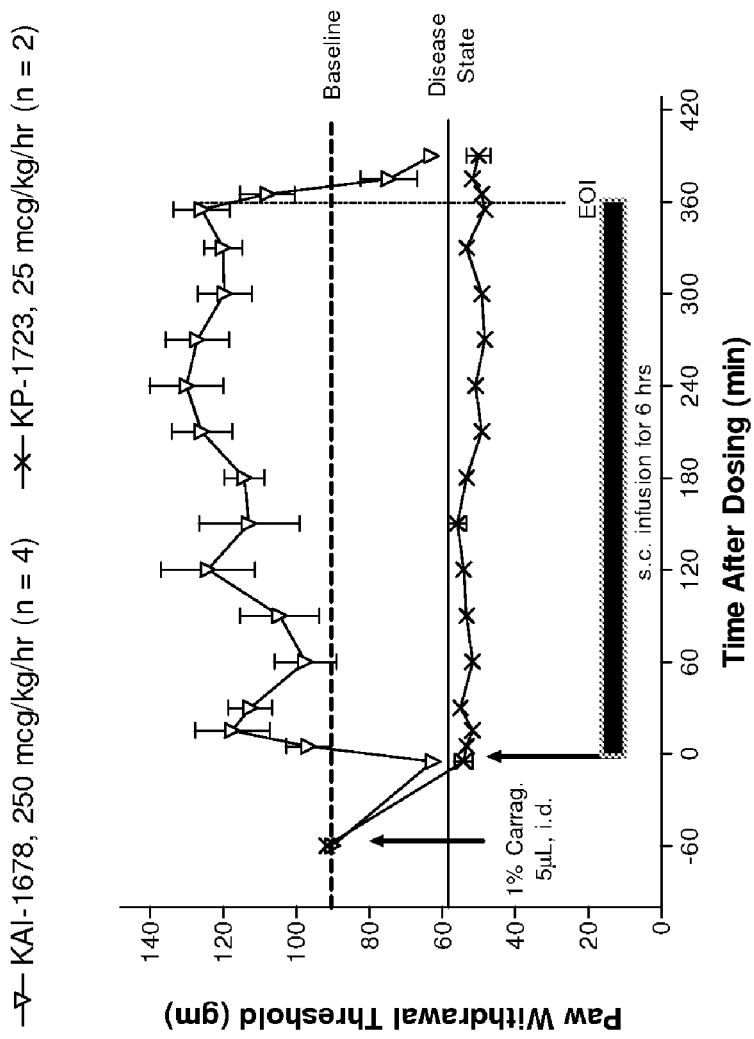
FIG. 21: Effects of Subcutaneous Infusion of KAI-1678 on Mechanical Hyperalgesia in the Carrageenan Inflammatory Pain Model in Rats. Rats were treated with a 6-hour subcutaneous infusion of KAI-1678 or KP-1723, the inactive analog of KAI-δ 678, 60 minutes after carrageenan injection into the plantar side of the right hindpaw. KAI-1678 or KP-1723 was administered at the indicated dose rates to the contralateral hindlimb (i.e. the limb that did not receive the carrageenan). Data are presented as mean±SEM (standard error of the mean) for the (PWT) measurements for the animals in each group (N=2-6 animals/group) at a given time point. The dotted line at ~90 g represents the pre-carrageenan baseline PWT measurement; PWT indicative of the disease state is ~55 g. Measurements at or above the pre-carrageenan baseline level indicate complete reversal of carrageenan-induced mechanical hyperalgesia.

A comparison of the results shown in FIG. 17 (intradermal dosing) with those of FIG. 18 (subcutaneous dosing) indicates that both routes of administration cause a rapid response, with complete reversal of mechanical carrageenan-induced hyperalgesia occurring as early as five minutes after dosing at the higher doses. However, the duration of the effect following subcutaneous bolus administration was shorter than that seen with intradermal administration adjacent to the carrageenan injection site. In an attempt to extend the duration of the anti-hyperalgesic effect, KAI-1678 was administered as a subcutaneous infusion to rats starting one hour after intradermal injection of carrageenan. As shown in FIG. 21, a subcutaneous infusion of KAI-1678 extended the duration of the response in a dose-dependent fashion. However, the response to the subcutaneous infusion occurred in two phases. The first phase, which lasted approximately one hour, consisted of a rapid and complete reversal of the mechanical hyperalgesia at all doses tested. The second phase, which developed typically between two and three hours after the start of the infusion, was dose dependent with only the higher doses ($\geq 25$ mcg/kg/hr) of KAI-1678 completely reversing mechanical hyperalgesia as indicated by a return of the paw withdrawal threshold to pre-carrageenan baseline levels. At 250 mcg/kg/hr the reversal of pain was rapid and sustained without any recurrence of hyperalgesia; although during the infusion a small decline in paw withdrawal threshold was observed at ~60 minutes after the start of infusion. Of note, a 25,000 mcg/kg/hr dose rate of KAI-1678 was tested in a subsequent subcutaneous infusion experiment. This dose rate, which is 100-fold higher than the 250 mcg/kg/hr dose rate tested in the experiment shown in FIG. 21, produced an effect comparable to that seen with the 250 mcg/kg/hr infusion (data not shown). Therefore, subcutaneous infusion of KAI-1678 does not appear to display the parabolic dose-response observed with bolus subcutaneous administration of the compound in this model (see FIG. 19).

At subcutaneous infusion rates $\geq 25$ mcg/kg/hour the efficacy achieved during the second phase was maintained for the duration of the infusion but was rapidly reversed following the end of infusion (FIG. 21). As discussed below, plasma levels of KAI-1678 declined at the end of a subcutaneous infusion but with a terminal half-life of ~30 minutes. Thus the decline in efficacy at the end of a subcutaneous infusion appears to be more rapid than the drop in plasma concentrations, implying that plasma concentrations are not the primary factor in determining efficacy.

Intravenous Administration of KAI-1678

The intradermal and subcutaneous studies described above indicate that KAI-1678 is efficacious when administered at a site remote from the site of injury, suggesting that the compound may have a system-wide effect. We therefore investigated whether systemic administration of KAI-1678 via the intravenous (IV) route was efficacious in the carrageenan inflammatory pain model. The IV infusion dose rates used in these studies were selected to achieve plasma levels of KAI-1678 that matched or exceeded those associated with fully efficacious subcutaneous infusions of KAI-1678 (e.g., $\geq 25$ mcg/kg/hr) based on the results of pharmacokinetic experiments (see below).

Figure 22:
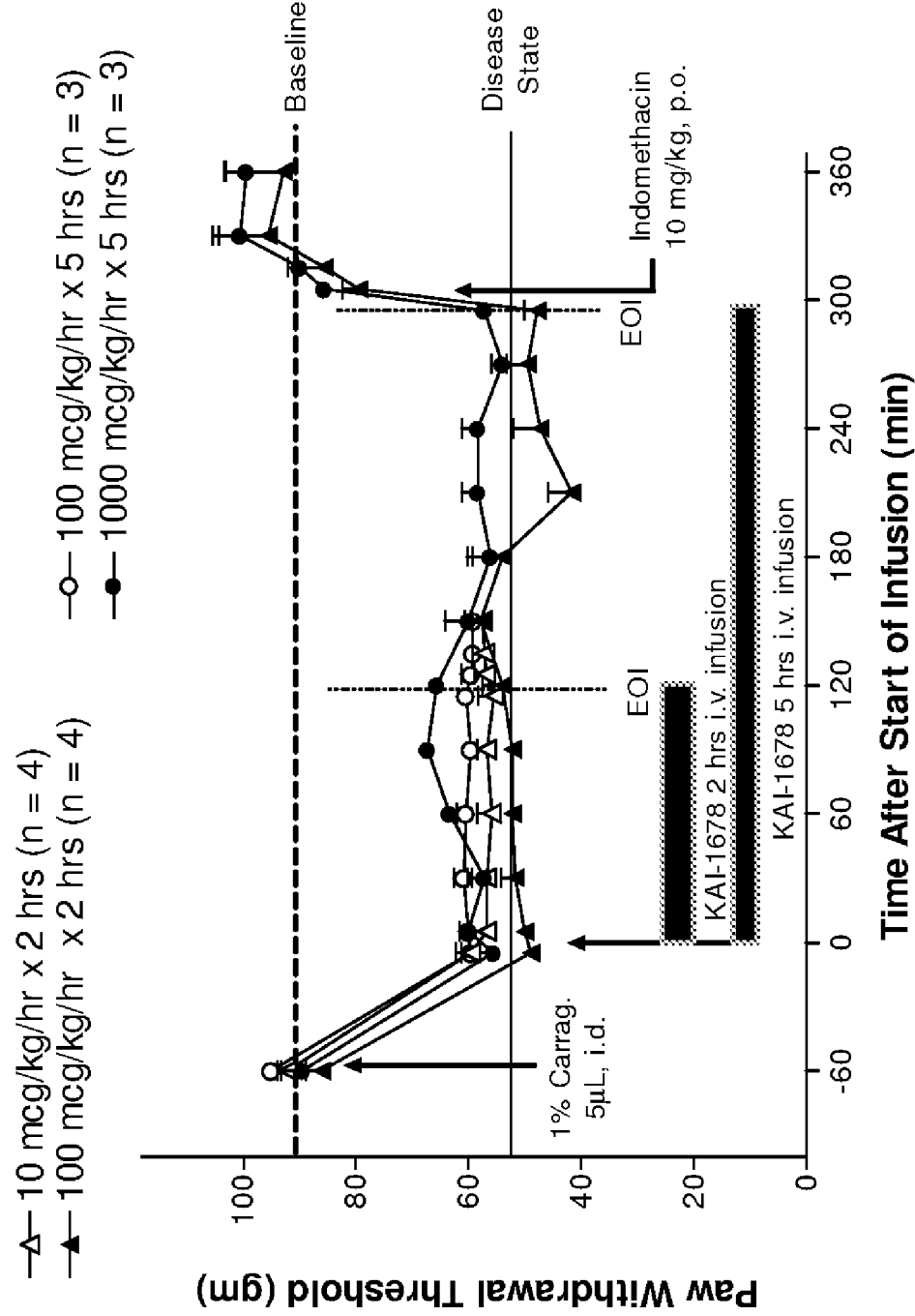
FIG. 22: Effects of Intravenous Infusion of KAI-1678 on Mechanical Hyperalgesia in the Carrageenan Inflammatory Pain Model in Rats. Rats were treated with an intravenous infusion of KAI-1678 starting 60 minutes after carrageenan injection into the plantar side of the right hindpaw. KAI-1678 was infused via the jugular vein at the indicated dose rates for either 2 hours (triangles) or 5 hours (circles). After the end of the 5-hour infusion, 10 mg/kg indomethacin was administered by oral gavage to test the responsiveness of the model. Data are presented as mean±SEM (standard error of the mean) for the (PWT) measurements for the animals in each group (N=3 or 4 animals/group) at a given time point. The dotted line at ~90 g represents the pre-carrageenan baseline PWT measurement; PWT indicative of the disease state is ~55 g. Measurements at or above the pre-carrageenan baseline level indicate complete reversal of carrageenan-induced mechanical hyperalgesia.

As shown in FIG. 22, IV infusions of KAI-1678 at rates as high as 1000 mcg/kg/hr for as long as 5 hours had no effect on carrageenan-induced mechanical hyperalgesia. Although plasma samples were not taken as part of these efficacy studies, pharmacokinetic studies suggest that plasma levels of KAI-1678 at the 100 mcg/kg/hr IV dose rate would be comparable to or greater than those achieved with the 25 mcg/kg/hr subcutaneous infusion (FIG. 20), and that plasma levels of KAI-1678 at the 1,000 mcg/kg/hr IV dose rate would be 5- to 10-fold higher than those achieved with the 250 mcg/kg/hr subcutaneous infusion. The inability of IV KAI-1678 to affect carrageenan-induced hyperalgesia does not appear to be due to any technical issues, since oral indomethacin, a known analgesic that has been shown to reduce carrageenan-induced hyperalgesia, completely reversed the mechanical hyperalgesia when administered after the end of the 5-hr IV infusion of KAI-1678. Moreover, the lack of IV activity does not appear to be unique to KAI-1678, as structurally related εPKC inhibitors that were efficacious in this model following intradermal or subcutaneous administration were not active when administered as an IV infusion (data not shown).

Site of Action Studies with KAI-1678 in the Rat Carrageenan Model

The demonstration that KAI-1678 appears to elicit a system-wide response, but only when administered intradermally or subcutaneously suggested that the primary site of action for the compound might be in the periphery.

This hypothesis, combined with the observation that the response to KAI-1678 administration was very rapid, even when the compound was administered to the contralateral limb, suggested that the afferent nerves in the skin at the site of compound administration might be essential for the rapid onset of action. Since signals propagated via the peripheral afferent nerves in the skin on the contralateral hindlimb would have to travel via the sciatic and saphenous nerves to affect mechanical hyperalgesia at the site of carrageenan injection on the ipsilateral hindpaw, the need for intact sciatic and saphenous nerves on the side of compound administration was investigated.

Figure 23:
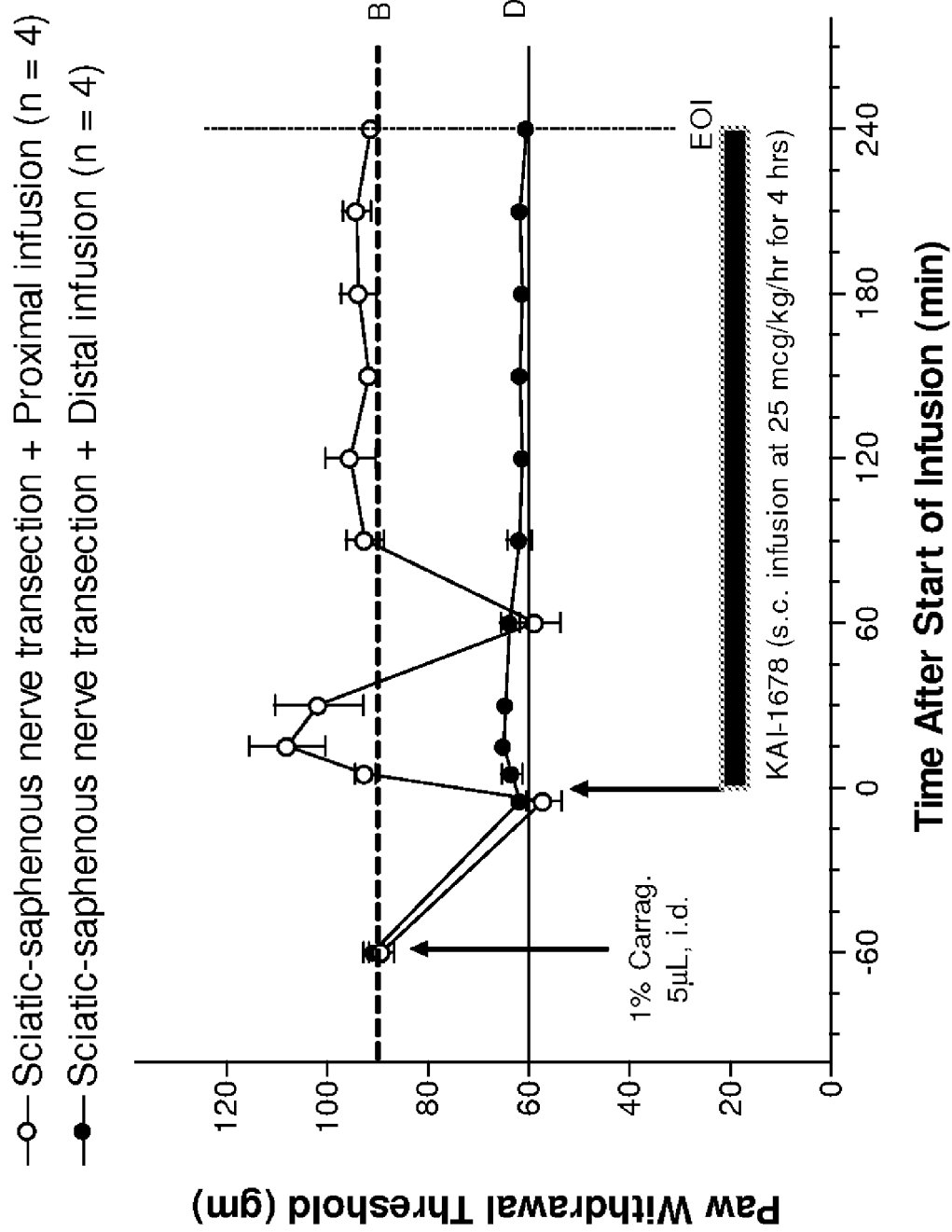
FIG. 23: Effect of Cutting the Sciatic and Saphenous Nerves on the Activity of KAI-1678 in the Carrageenan Inflammatory Pain Model in Rats. A 1-cm section of the sciatic and saphenous nerves was surgically removed from the left (contralateral) hindleg of rats. The next day, carrageenan was injected into the plantar side of the right hindpaw of the surgically-treated rats. Sixty minutes after carrageenan injection, a 4-hour subcutaneous infusion of KAI-1678 at 25 mcg/kg/hr was initiated on the contralateral limb at a site proximal (open circles) or distal (closed circles) to the site of the nerve transection. Data are presented as mean±SEM (standard error of the mean) for the (PWT) measurements for the animals in each group (N=4 animals/group) at a given time point. The dotted line at ~90 g represents the pre-carrageenan baseline PWT measurement; PWT indicative of the disease state is ~60 g. Measurements at or above the pre-carrageenan baseline level indicate complete reversal of carrageenan-induced mechanical hyperalgesia.

In the experiment shown in FIG. 23, a 1-cm section of the sciatic and saphenous nerves was removed from the left hind-leg of rats. The next day, after the rats had recovered from surgery, carrageenan was injected into the plantar surface of the right hindpaw of the rats to elicit an inflammatory response. Sixty minutes after injection of carrageenan into the right hindpaw, KAI-1678 was administered as a subcutaneous infusion to the left hindlimb at a site either proximal or distal to the site where the 1-cm section of the sciatic and saphenous nerves had been removed. As shown in FIG. 23, a 25 mcg/kg/hr subcutaneous infusion of KAI-1678 was effective at eliminating carrageenan-induced mechanical hyperalgesia when the site of compound administration was proximal, but not distal, to the site of nerve transection. Comparing with historical data (FIG. 21), the response to KAI-1678 administered proximal to site of the transection of the sciatic and saphenous nerves was similar to the response observed in surgically naïve rats (see FIG. 21), although the onset of the second phase of activity appears to be more rapid in the rats administered KAI-1678 as a subcutaneous infusion proximal to the site of nerve transection. Although it is possible that other secondary effects of the surgical procedure may have impacted the response to subcutaneous infusion distal to the site of nerve transection, the results of this experiment suggest that innervation at the site of administration is required for KAI-1678 efficacy. As the sciatic and saphenous nerves contain motor neurons, primary sensory afferent neurons, and sympathetic neurons, these data do not allow us to definitively assign the site of action to one of these subsets of neurons.

This finding suggests that 1678 may be acting on 'normal' neurons to transmit a signal centrally resulting in system-wide pain suppression. This modulation could be occurring in the dorsal horn; however, efficacy is observed when KAI-1678 is administered to sites outside of the dermatome affected by the pain stimulus, suggesting that system-wide pain suppression is occurring above the level of the spinal cord (see below).

Figure 24:
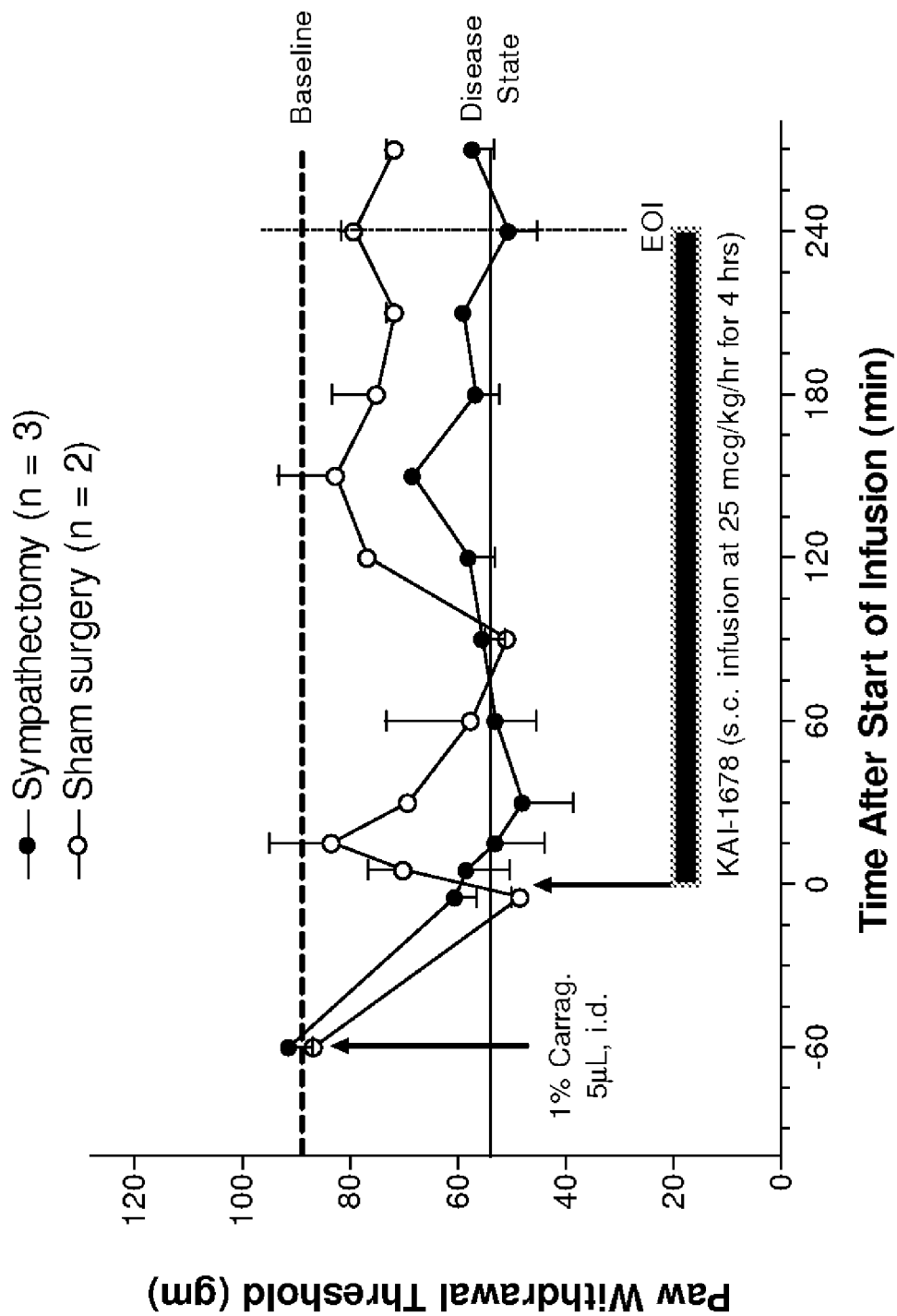
FIG. 24: Effect of Surgical Sympathectomy on the Activity of Subcutaneously Administered KAI-1678 on Mechanical Hyperalgesia in the Carrageenan Inflammatory Pain Model in Rats. One week following bilateral lumbar sympathectomy and suprarenal ganglionectomy, carrageenan was injected into the plantar side of the right hindpaw of surgically treated rats (Sympathectomized animals—closed circles) or rats in which the lumbar sympathetic chain and suprarenal ganglia were exposed but not removed (Sham surgery animals—open circles). Sixty minutes after carrageenan injection, a 4-hour subcutaneous infusion of KAI-1678 at 25 mcg/kg/hr was initiated into the hindlimb of each animal, contralateral to the site of carrageenan administration. Data are presented as mean±SEM (standard error of the mean) for the (PWT) measurements for the animals in each group (N=2-4 animals/group) at a given time point. The dotted line at ~90 g represents the pre-carrageenan baseline PWT measurement; PWT indicative of the disease state is ~55 g. Measurements at or above the pre-carrageenan baseline level indicate complete reversal of carrageenan-induced mechanical hyperalgesia.

Earlier studies have reported that catecholamines from the sympathoadrenal system are involved in carrageenan-induced inflammatory pain and that εPKC is expressed in the sympathetic system. We therefore investigated whether an intact sympathoadrenal system was required to maintain the efficacy of distally administered KAI-1678. As shown in FIG. 24, bilateral lumbar sympathectomy plus suprarenal ganglionectomy did not alter the pain responses to carrageenan. However, the ability of KAI-1678, administered as a 25 mcg/kg/hr subcutaneous infusion to the contralateral hindlimb, to reverse the carrageenan-induced mechanical hyperalgesia was abrogated in these animals. As shown in FIG. 24, both the early and the later phases of the bi-phasic response to subcutaneous KAI-1678 infusion are eliminated by the sympathectomy and suprarenal ganglionectomy. In previous experiments with ☐V1-2-containing analogs of KAI-1678, we have also demonstrated that surgical sympathectomy, as described above, eliminates the effect of εPKC inhibitors administered as a bolus injection at a remote subcutaneous site, as well as at an intradermal site adjacent to the injury.

The sympathectomy experiments described above require surgical intervention and recovery of animals for a week prior to intervention with the carrageenan. As shown in FIG. 24, sham surgery, without sympathectomy, may have partially reduced the efficacy of KAI-1678. Consequently we sought to complement this study by investigating the effect of pharmacological blockade of the sympathetic nervous system function, using the alpha-adrenergic antagonist phentolamine, thus eliminating the need for surgery. Administration of this agent at the time of carrageenan injection did not influence the establishment of pain, although the effect of remote site subcutaneous bolus administration of an ☐V1-2-containing analog of KAI-1678 was eliminated, as was the effect of an intradermal administration local to the site of injury (data not shown). Furthermore, the efficacy of an ☐V1-2-containing analog of KAI-1678 following subcutaneous bolus administration in a second, neuropathic, pain model was also eliminated by prior administration of phentolamine, although, again, the phentolamine did not prevent the establishment of pain in this model (data not shown).

Thus, surgical ablation of the sympathetic nervous system and pharmacologic blockade of alpha adrenergic receptors block the anti-hyperalgesic activity of εPKC inhibitors. It is not clear if these effects reflect a dependence on the sympathetic nervous system or on adrenergic receptor signaling in the CNS.

Summary of Carrageenan Inflammatory Pain Model Studies

The data above demonstrate that KAI-1678 can reverse inflammatory pain when administered intradermally at the site of injury and intradermally or subcutaneously at a remote site. Efficacy has not been observed with intravenous administration, even at KAI-1678 plasma levels equivalent to those obtained during an efficacious subcutaneous infusion. We have also demonstrated that the remote site subcutaneous efficacy of KAI-1678 is dependent on innervation at the site of administration, which suggests that the remote-site efficacy of KAI-1678 is mediated by an effect on subcutaneous neurons that are exposed to KAI-1678 at the site of administration. One hypothesis to explain these data is that, by acting on skin nociceptors, KAI-1678 elicits an ascending signal in the primary afferent neurons that initiates a spinal or supraspinal reflex, ultimately resulting in descending pain suppression of the carrageenan-induced hyperalgesia. Alternatively KAI-1678 might be acting by reducing tonic signaling in neurons at the injection site and this inhibition might lead to the descending pain suppression. Descending modulation might involve alpha adrenergic signaling, which would be consistent with the effect of phentolamine on KAI-1678 efficacy. Thus, in the spinal cord, nor epinephrine released from descending pathways suppresses pain by inhibitory action on alpha-2A-adrenoceptors on central terminals of primary afferent nociceptors (presynaptic inhibition), by direct alpha-2-adrenergic action on pain-relay neurons (postsynaptic inhibition), and by alpha-1-adrenoceptor-mediated activation of inhibitory interneurons. This hypothesis contrasts with other models of εPKC action, in which a role has been proposed for εPKC in primary afferent nerve terminals modulating membrane channels and membrane depolarization in response to inflammatory stimuli.

Activity of KAI-1678 in Neuropathic Pain Models

The activity of KAI-1678 has been evaluated in the L5 transection model or modified Chung model, is a mononeuropathic pain model in which the L5 spinal nerve is surgically transected, resulting in rapid development of sustained pain. The activity of KAI-1678 in this model is described below.

Activity of KAI-1678 in the L5 Spinal Nerve Transection Mononeuropathic Pain Model in Rats The rat L5 spinal nerve transection model has been used to evaluate the response to modulators of neuropathic pain. In the studies described below surgical transaction of the L5 spinal nerve was used to elicit mechanical allodynia, mechanical hyperalgesia and thermal hyperalgesia that characterize neuropathic pain. In this model, the neuropathic effects develop within a day and are reported to last for 1-2 months.

Mechanical allodynia and mechanical hyperalgesia are measured using calibrated von Frey filaments to elicit a flexion withdrawal response (paw withdrawal response) by pressing them against the plantar surface of the hindpaw on the same side as the nerve transection. The 2 g, 6 g and 10 g von Frey filaments are used to assess allodynia since these stimuli are normally innocuous to naïve animals. The 15 g, 26 g and 60 g filaments are used to assess algesia (response to noxious stimulus) since these stimuli elicit paw withdrawals in naïve animals and are considered to represent painful stimuli.

The existence of the disease state following nerve transection is confirmed based on tests performed with the 2 g and the 10 g filaments. When tested with a total of 3 sets of 10 tests (30 tests total), the number of paw withdrawals in response to the 2 g von Frey filament typically increases from 1-2 prior to nerve injury to 12-15 paw withdrawals following surgery. Similarly, the number of paw withdrawals in response to the 10 g filament typically increases from 2-3 prior to nerve injury to 20-23 paw withdrawals following surgery. In the absence of further treatment, the mechanical allodynia remains stable for at least 3 weeks, making it possible to use this model to evaluate the time course of the response to treatment either as a bolus administration or an extended infusion, with sequential measurements typically over the course of 1-2 weeks after establishment of the disease state.

Once the disease state is confirmed, evaluation of the extent of mechanical allodynia or hyperalgesia is determined by observing the number of paw withdrawals in response to 5 tests with each of the von Frey filaments. Results are typically expressed either as the total number of paw withdrawals for the allodynic filaments (2 g, 6 g and 10 g for a total of 15 tests) or the algesic filaments (15 g, 26 g and 60 g for a total of 15 tests), or as the lowest filament to which the animals in a group have an average positive response defined as ≧3 withdrawals out of 5 tests with a particular filament.

Along with measurements of the effects of compound treatment on mechanical allodynia and hyperalgesia, changes in the level of thermal algesia in response to L5 spinal nerve transection have also been determined in this model using, the Hargreaves test. In these studies, rats are placed on a glass surface above a radiant heat source focused on the lateral plantar surface of the affected hindpaw. When the heat source is turned on, the glass surface heats up over time. The time until the animal lifts its hindpaw (paw withdrawal latency, measured in seconds) is an indicator of thermal algesia. Under the conditions used in this study, paw withdrawal latency decreases from 10-12 seconds prior to nerve injury to 6-8 seconds after L5 nerve transection, indicating the development of thermal hyperalgesia. In the absence of further treatment, the thermal hyperalgesia remains stable for at least three weeks.

Subcutaneous Administration of KAI-1678

Rats given an L5 spinal nerve transection were treated with a bolus subcutaneous dose of KAI-1678 ranging from 0.00025-0.25 mcg/rat (~0.001-1 mcg/kg) on day 7 post-transection. The degree of mechanical allodynia and hyperalgesia was evaluated based on the number of paw withdrawals (out of 30) in response to 6 different von Frey filaments before and up to 3 hours after administration of the compound. For comparison, some rats were dosed with 0.250 mcg/rat (~1 mcg/kg) KP-1723, the inactive analog of KAI-1678.

Figure 25:
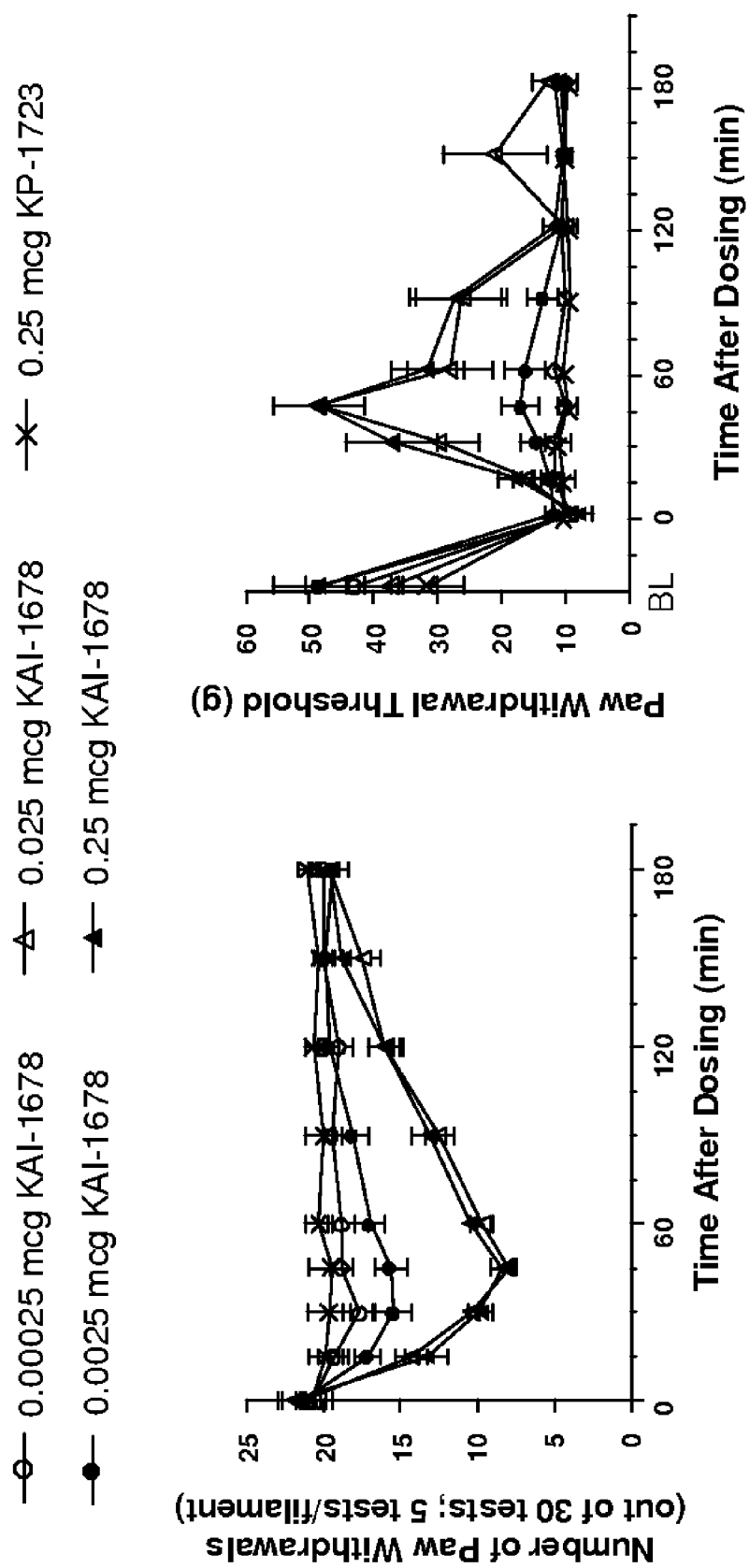
FIG. 25: Effects of Subcutaneous Bolus Administration of KAI-1678 on Mechanical Allodynia in the L5 Transection Neuropathic Pain Model in Rats. Seven days after transection of the L5 spinal nerve, rats were given a subcutaneous bolus of KAI-1678 at the indicated doses (time zero). At the indicated times after compound administration, animals were tested with von Frey filaments to determine (left) the number of paw withdrawals out of 30 tests (5 tests at each filament) or (right) the paw withdrawal threshold determined as the lowest von Frey filament that produced at least 3 withdrawals out of 5 tests. Data are presented as mean±SEM (standard error of the mean) for the animals in each group (N=6 animals/group) at a given time point.

As shown in FIG. 25, KAI-1678 treatment resulted in a dose-dependent decrease in mechanical allodynia and mechanical hyperalgesia at doses $\geq$0.01 mcg/kg. Based on composite measurements with the 15 g, 26 g and 60 g von Frey filaments (FIG. 25, left), KAI-1678 at 0.1 and 1 mcg/kg completely reverses mechanical hyperalgesia, as indicated by the return to pre-surgery responses. Complete reversal of the hyperalgesia at these two doses was observed between 30 and 60 minutes after compound administration, and an anti-hyperalgesic effect was observed for at least 2 hours. In contrast to the results obtained with KAI-1678, KP-1723 treatment at 1 mcg/kg had no effect on mechanical hyperalgesia. Comparable results to those described above were obtained when the 2 g, 6 g and 10 g von Frey filaments were used in order to measure KAI-1678 effects on L5-transection-induced mechanical allodynia (data not shown).

The efficacy of KAI-1678 in this model was also apparent when paw withdrawal threshold was measured by determining the minimum von Frey filament to elicit 3 paw withdrawals out of 5 stimulations (FIG. 25, right).

Figure 26:
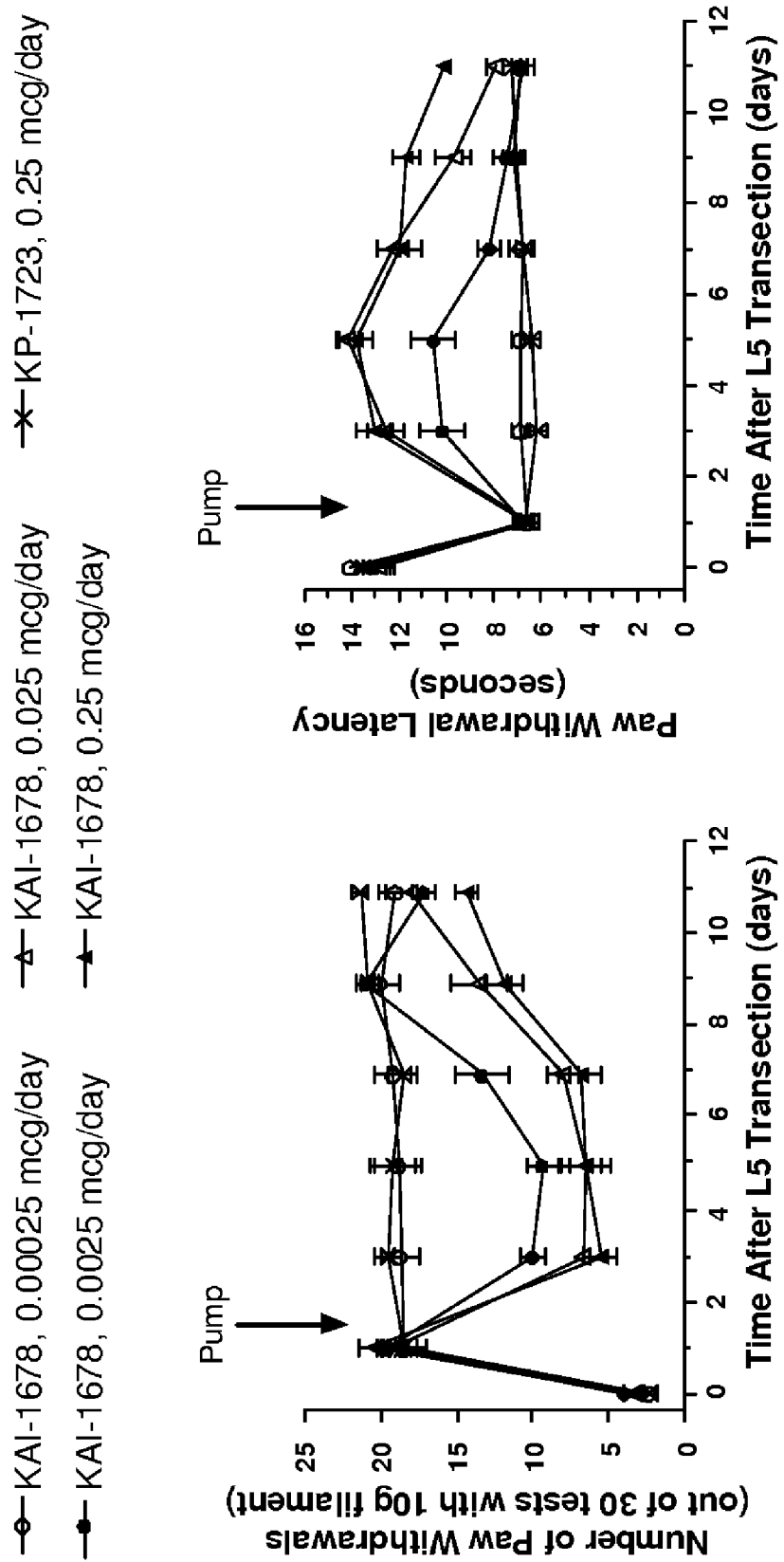
FIG. 26: Effects of Subcutaneous Infusion of KAI-1678 on Allodynia in the L5 Transection Neuropathic Pain Model in Rats. The day after transection of the L5 spinal nerve, osmotic minipumps containing KAI-1678 were implanted subcutaneously to deliver the indicated daily doses of compound. At the indicated times, animals were tested (left) with von Frey filaments to determine the number of paw withdrawals out of 30 tests (5 tests at each filament) or (right) the paw withdrawal latency in response to exposure to a radiant heat source. Data are presented as mean±SEM (standard error of the mean) for the animals in each group (N=6 animals/group) at a given time point.

To determine whether the efficacy of KAI-1678 in this model could be prolonged with continuous delivery, subcutaneous exposure, osmotic minipumps delivering 0.00025-0.25 mcg/day (~0.001-1 mcg/kg/day) of KAI-1678 or 0.25 mcg/day (~1 mcg/kg/day) KAI-1723 were implanted subcutaneously between the scapula on day 2 post-transection. Mechanical allodynia was examined on Days 3, 5, 7, 9, 11 post-transection (Days 1, 3, 5, 7, 9 post-pump implantation) using the 2 g and the 10 g filaments. As shown in FIG. 26 (left), results from the tests with the 10 g filament indicate that KAI-1678 dose rates $\geq$0.0025 mcg/day (~0.01 mcg/kg/day) are able to substantially reduce the level of mechanical allodynia, with the 0.025 and 0.25 mcg/day (~0.1 and 1 mcg/kg/hr) dose rates producing nearly complete reversal of mechanical allodynia that lasted until Day 7 post-pump implantation. At the highest dose rate, evidence of reduction in mechanical allodynia was observed as late as Day 11 post-transection. Similar results were obtained using the 2 g filament to evaluate mechanical allodynia (data not shown) and using the Hargreaves test to thermal hyperalgesia (FIG. 26, right). After about 5 days of complete reversal of hyperalgesia in the presence of pumps containing KAI-1678, we noted a loss of efficacy. This was not due to a tolerance to the drug, as a subcutaneous bolus administration of the drug at this time elicited complete reversal of pain (data not shown) and it may be that the loss of effect was due to a failure of the pumps to maintain delivery.

Summary of Neuropathic Pain Model Studies

The data above demonstrate that KAI-1678 is extremely effective in the L5 spinal nerve transection mononeuropathic pain model. The potency of KAI-1678 administered as a subcutaneous bolus is comparable in reversing mechanical and thermal allodynia in the L5 spinal transaction model. When administered by subcutaneous infusion, KAI-1678 is about 1000-fold more potent than in the carrageenan-induced inflammatory pain model. The reason for the high sensitivity of the L5-transection model to KAI-1678 treatment is not known, but it likely reflects the responsiveness of this model to selective ePKC inhibitors, since this model is exhibits a similar high sensitivity to structurally-related analogs of KAI-1678. The demonstration that KAI-1678 has activity in two neuropathic pain models suggests that this compound may have clinical utility for the management of neuropathic pain in humans.

Conclusion from Rat Pharmacology Studies

The activity of KAI-1678 has been evaluated in rat inflammatory and neuropathic pain models. Subcutaneous administration of the compound is efficacious in the models shown. The potency of KAI-1678 administered by subcutaneous bolus is similar across the models, as is the rapid onset and duration of effect tested, although the overall effect size does vary between models. The response to different infusion dose rates is also different between models. In particular, the L5 transection mononeuropathic pain model appears to be particularly sensitive to KAI-1678 with doses approximately one thousand fold lower being active in this model than in the carrageenan model.

While experiments with these models are continuing, additional work is being done in other pain models. In particular, preliminary results in the Brennan incision model and the single spared nerve model suggest that KAI-1678 is also active in these models at doses similar to those that are active in the carrageenan model.

Taken together, the available animal efficacy data suggest that KAI-1678 may be active in a variety of pain models and support the continued development of the compound.

Pharmacokinetics in Animals

The pharmacokinetics of KAI-1678 are being studied in rats administered the compound as an intravenous bolus and infusion or as a subcutaneous bolus and infusion. The toxicokinetics of KAI-1678 are being studied in dogs administered the compound as a subcutaneous infusion as part of the toxicity studies. In these studies, plasma levels of KAI-1678 have been determined using a sandwich-based ELISA assay developed at KAI Pharmaceuticals. The lower limit of quantitation of this assay is approximately 0.3 ng/mL. A similar assay has been developed to measure tissue levels of KAI-1678.

In rats KAI-1678 is rapidly cleared from systemic circulation following intravenous bolus administration. When administered as a 2-hr intravenous infusion at 50 mcg/kg/hr, steady state plasma concentrations of approximately 10-20 ng/mL appeared to be achieved by 60 minutes, and dropped off rapidly after the end of infusion. The terminal half-lives for the bolus and infusion administrations of KAI-1678 via the intravenous route are approximately 50 and 25 minutes, respectively.

Subcutaneous administration of KAI-1678 to rats as either a bolus (approximately 80 or 800 mcg/kg) or as an infusion (19 and 190 mcg/kg/hr) resulted in dose-proportional increases in exposures over the doses tested. Plasma concentrations of KAI-1678 reached maxima at approximately 10 minutes and 1 hour for the subcutaneous bolus and infusions, respectively, and then decreased with a half-life of approximately 35 and 45 minutes, respectively, once the peptide was no longer being administered. The bioavailability of KAI-1678 administered by the subcutaneous route is approximately 10% in rats.

Although the terminal half-life was not determined, KAI-1678 was also rapidly cleared from the systemic circulation in dogs administered KAI-1678 following an extended subcutaneous infusion over 5 days. In this study, KAI-1678 was detected in tissue samples from a variety of organs removed at the end of infusion (most notably the kidney, liver and lung), while levels of KAI-1678 in brain and spinal chord were consistently low.

Rat Pharmacokinetics

Intravenous Administration

Figure 27:
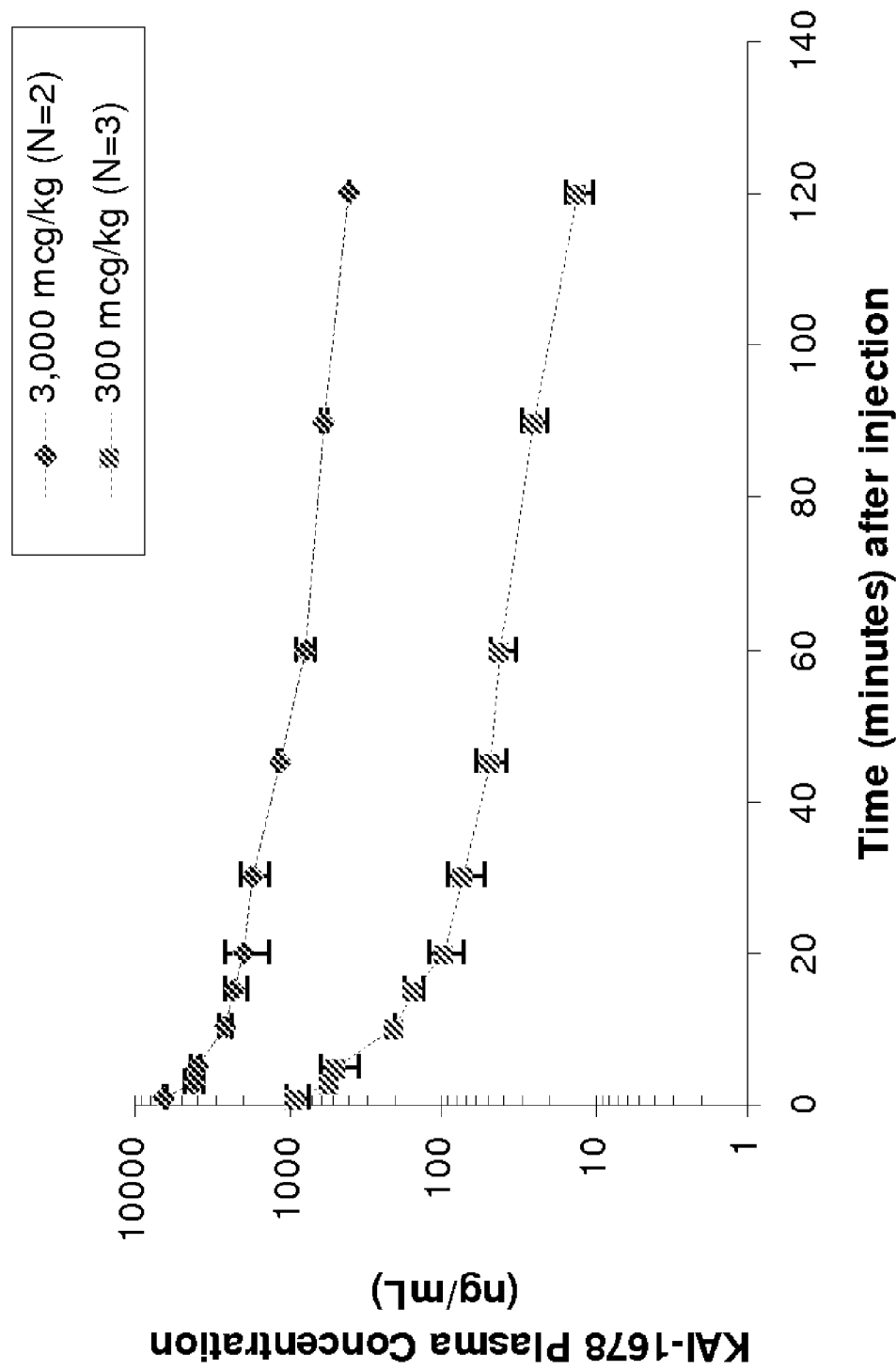
FIG. 27: KAI-1678 Plasma Concentrations in Rats After IV Bolus. Plasma concentrations of KAI-1678 after intravenous bolus administration at 300 and 3,000 mcg/kg. Averaged data from three rats (300 mcg/kg) and two rats (3,000 mcg/kg) are shown. A preliminary estimation of terminal half-life from these data is ~38 and ~66 minutes (300 mcg/kg and 3,000 mcg/kg, respectively).

To initially characterize the pharmacokinetics of KAI-1678 in rats, male rats were administered KAI-1678 at doses of 100 and 1,000 mcg/rat (~300 and ~3,000 mcg/kg) as an IV bolus injection via the tail vein. Blood samples were withdrawn periodically for up to two hours following the injection for plasma analysis of KAI-1678 levels. There were three and two animals in the 100 and 1,000 mcg dose groups, respectively, and there was consistency in KAI-1678 plasma concentrations between animals in each dose group. As shown in FIG. 27, $C_{max}$ plasma levels of KAI-1678 increased in a dose-proportional manner over the doses tested. Preliminary analysis of these data indicates a terminal half-life of approximately 38 and 66 minutes for the ~300 mcg/kg and the ~3,000 mcg/kg dose levels, respectively.

Subcutaneous Administration

The majority of the animal efficacy studies have been performed with KAI-1678 administered to rats as a subcutaneous bolus or infusion. Therefore, the pharmacokinetics of KAI-1678 administered by the subcutaneous route has been evaluated based on measurements of plasma concentrations of KAI-1678.

Figure 29:
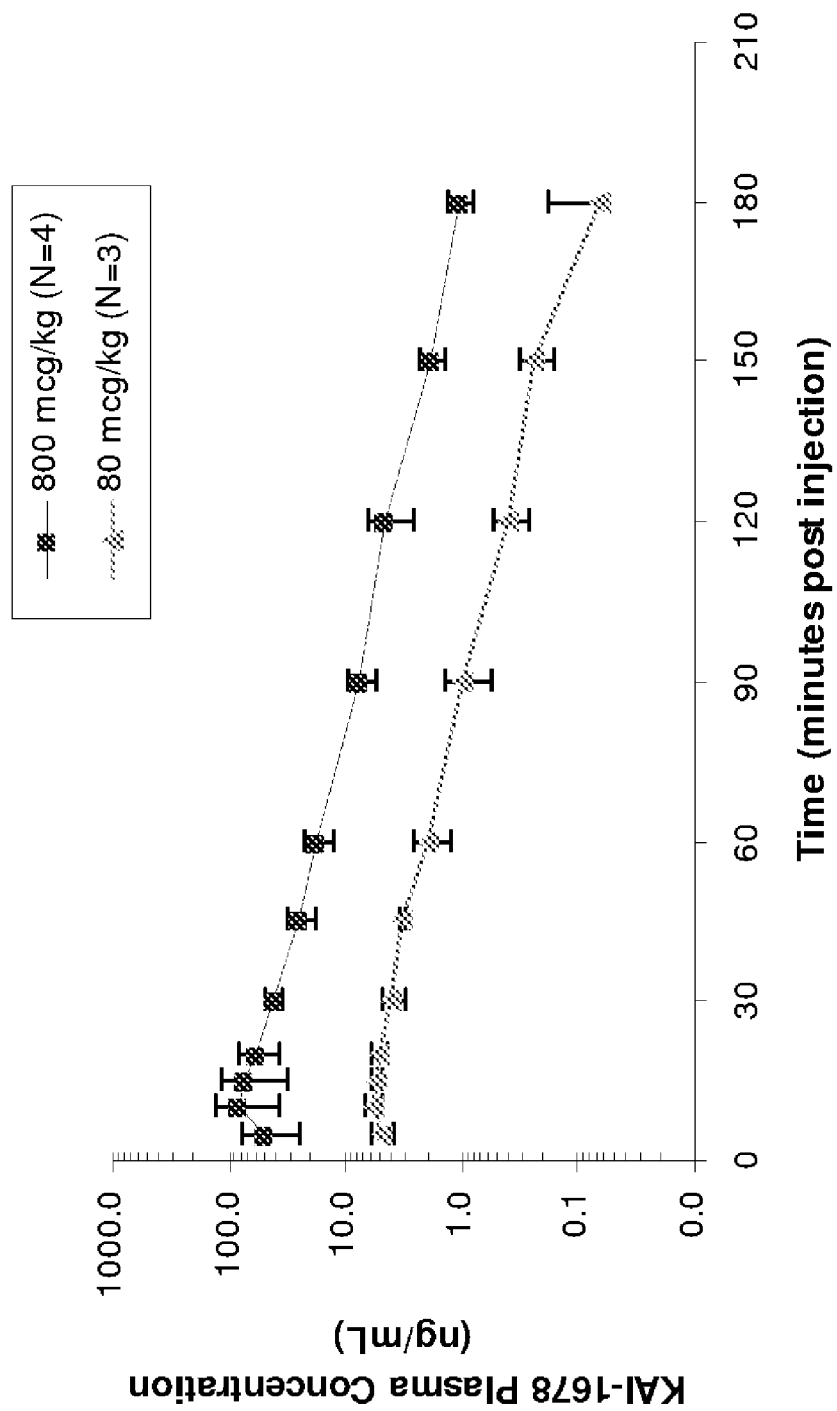
FIG. 29: KAI-1678 Plasma Concentrations in Rats after Subcutaneous Bolus Injection. Plasma concentration of KAI-1678 after subcutaneous bolus administration at approximately 80 and 800 mcg/kg. Averaged data from three rats (80 mcg/kg) and four rats (800 mcg/kg) are shown. A preliminary estimation of terminal half-life from these data is ~35 minutes.

In the experiment shown in FIG. 29, male rats were administered KAI-1678 as a subcutaneous bolus injection (200 microL into the left hindleg) at doses of 25 or 250 mcg/animal (approximately 80 and 800 mcg/kg, respectively). Blood samples were taken at various time points over two hours after administration of the compound to determine plasma concentrations of KAI-1678. There were three and four animals in the 25 and 250 mcg/animal dose groups, respectively, and the KAI-1678 plasma concentration measurements were consistent between animals in each dose group. $C_{max}$ occurred within 10 minutes after injection and increased in a dose-proportional manner over the two doses tested. A preliminary estimation of terminal half-life from these data is 35 minutes for both dose levels. A comparison of the areas under the plasma concentration versus time curves for KAI-1678 administered as an intravenous bolus and as a subcutaneous bolus indicates that the bioavailability of KAI-1678 administered via the subcutaneous route is approximately 10% in rats at this site of administration.

Figure 30:
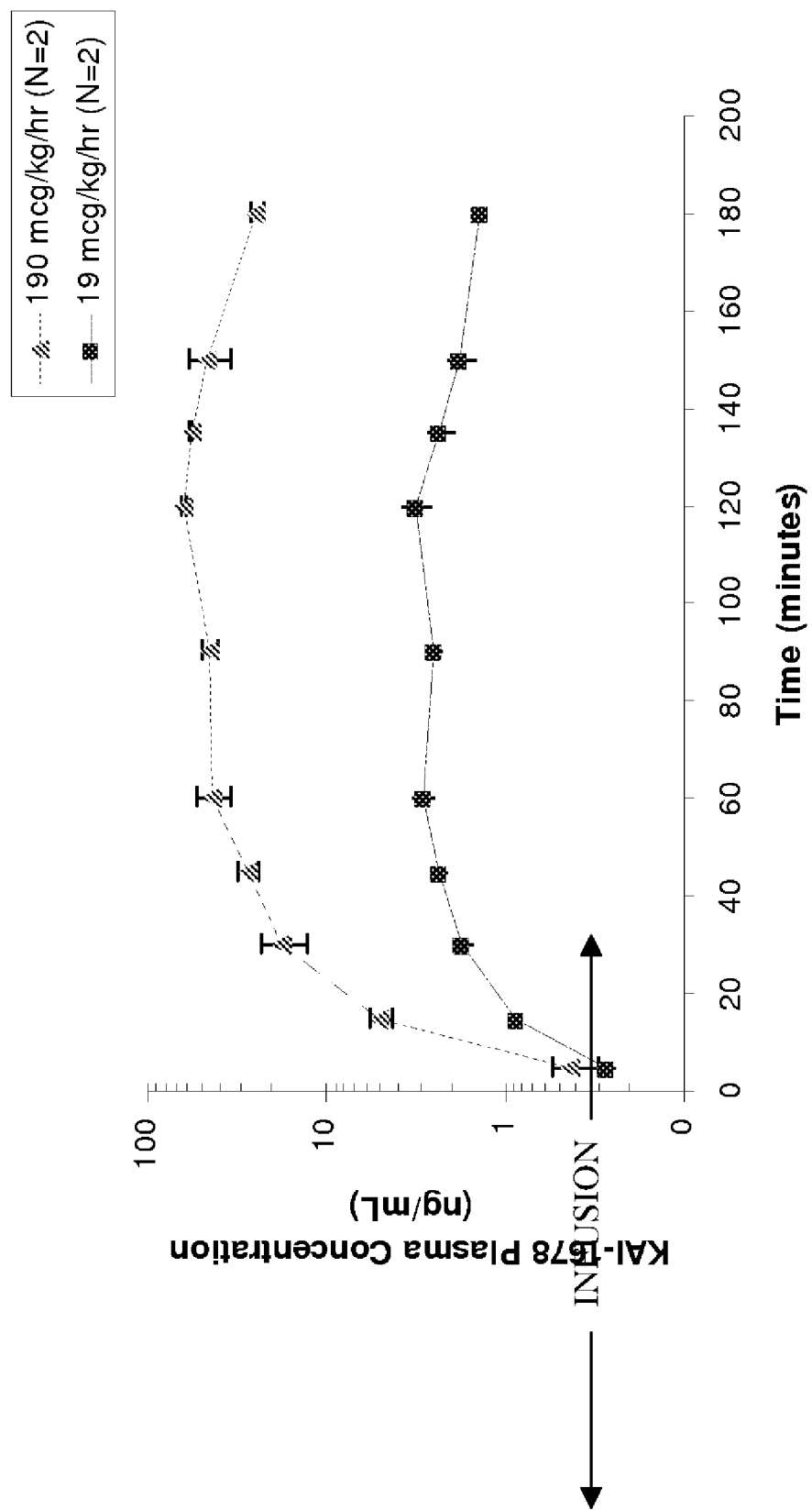
FIG. 30: KAI-1678 Plasma Concentrations in Rats Dosed by Subcutaneous Infusion. Plasma concentrations of KAI-1678 in rats dosed by subcutaneous infusion for two hours. Averaged data from two rats at each dose level are shown.

In the experiment shown in FIG. 30, male rats were administered KAI-1678 as a continuous subcutaneous infusion for 2 hours at doses of 19 and 190 mcg/kg/hr. Blood samples were taken at various time points throughout the infusion and for 1 hour after the end of infusion to determine plasma concentrations of KAI-1678. There were two animals per dose group and the plasma KAI-1678 concentration measurements were consistent between animals in each dose group. At the lower dose rate (19 mcg/kg/hr), plasma concentrations reached steady state (~3 ng/mL) by 60 minutes and remained relatively constant throughout the rest of the infusion. At the higher dose rate (190 mcg/kg/hr), plasma concentrations of KAI-1678 rose throughout the infusion and did not appear to reach a plateau, or steady state, within the two hours of infusion ($C_{max}$~60 ng/mL). At both dose rates, plasma concentrations of KAI-1678 dropped quickly after the end of infusion although compound was still detectable at both dose levels one hour after the end of infusion.

Figure 28:
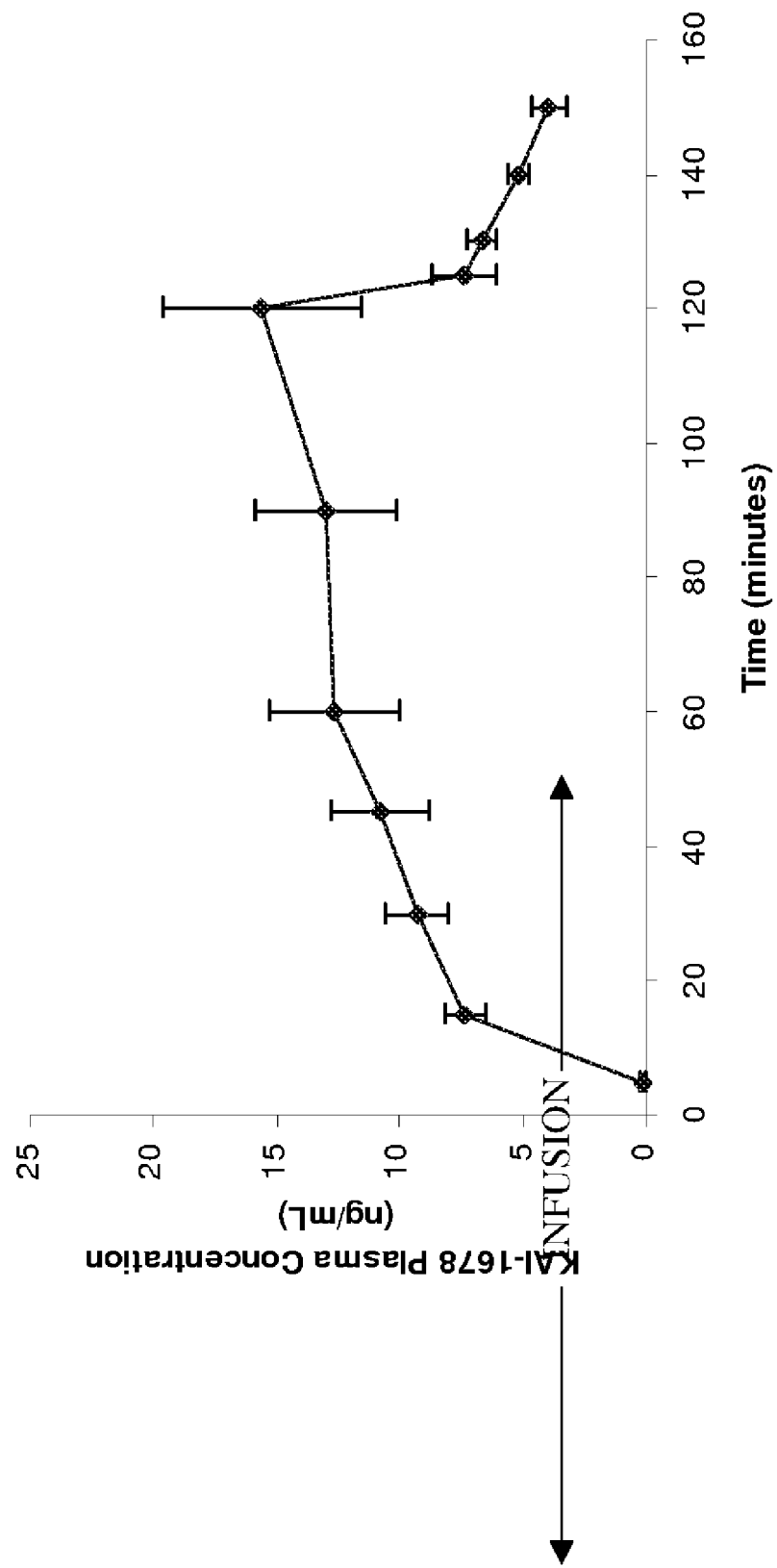
FIG. 28: KAI-1678 Plasma Concentrations in Rats Dosed by IV Infusion. Plasma concentrations of KAI-1678 administered as an intravenous infusion at 50 mcg/kg/hr. Averaged data from three rats are shown.

A comparison of the data in FIG. 28 and FIG. 30 indicates that a 50 mcg/kg/hr intravenous infusion of KAI-1678 will produce plasma concentrations of compound (10-20 ng/mL) that are higher than those achieved with a subcutaneous infusion at 19 mcg/kg/hr (~3 ng/mL) and nearly at the level achieved with a subcutaneous infusion at 190 mcg/kg/hr (~60 ng/mL). Interestingly, there does not seem to be a correlation with plasma concentration and efficacy, as efficacy is not observed with iv administration of KAI-1678 even at dose rates higher than those required to achieve maximal efficacy via subcutaneous infusion of the compound.

Dog Pharmacokinetics

Figure 31:
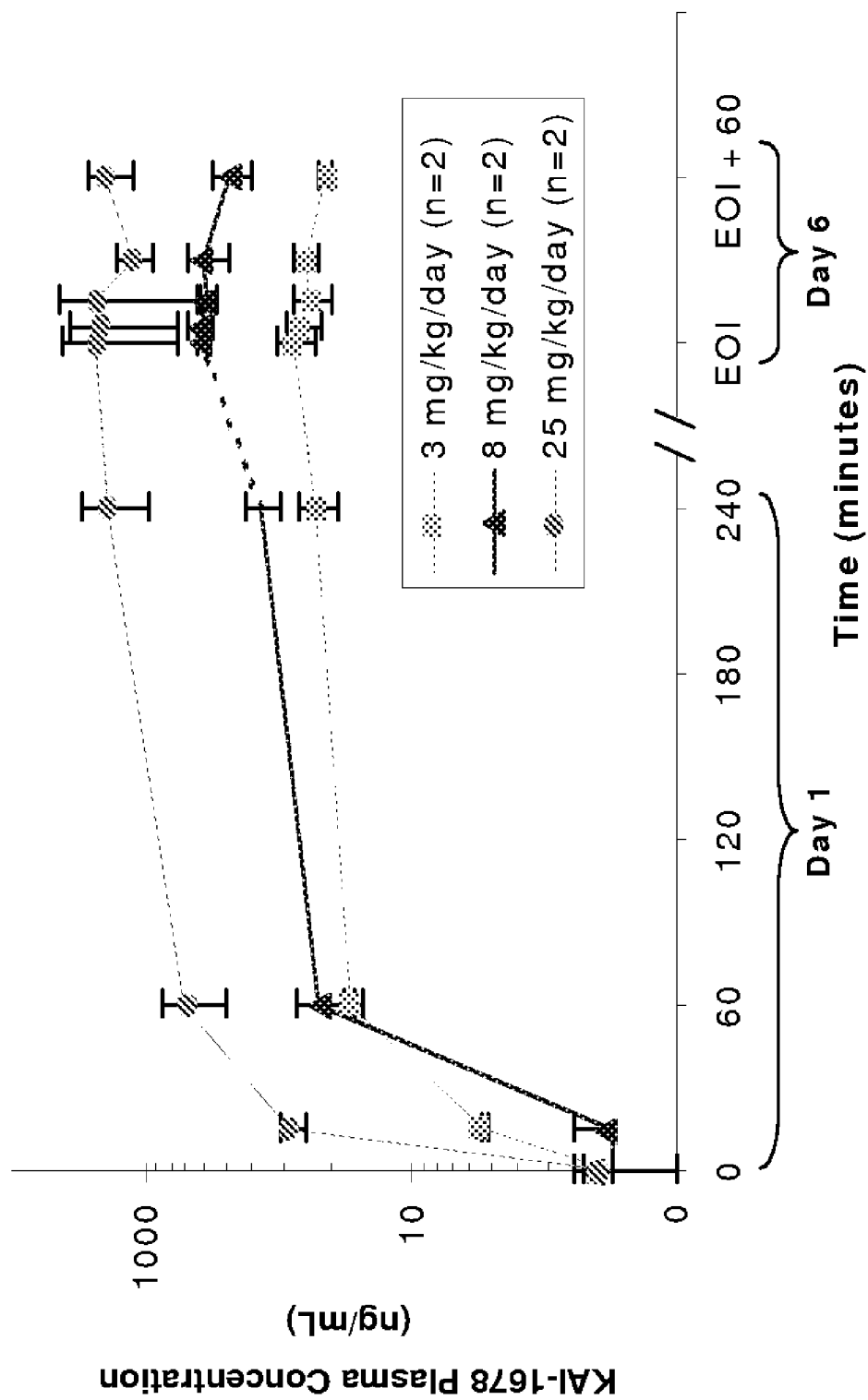

As part of a range-finding toxicology study, 6 beagle dogs (one per sex per group) were administered continuous subcutaneous infusions of KAI-1678 for 5 days at dose levels of 3, 8 and 25 mg/kg/day. Blood samples were collected at various times on Day 1 (start of infusion) and Day 6 (after the end of infusion). Plasma concentrations of KAI-1678 increased over the course of the first four hours of infusion, and in most cases increased another two- to three-fold by the end of infusion on the fifth day, suggesting that steady state was not reached within 4 hours of subcutaneous infusion at the dose levels tested (FIG. 31). However, at all dose levels, plasma levels declined quickly upon cessation of infusion although terminal half-life was not calculated because of the small number of data points available.

As part of this study, tissues were harvested from a subset of the animals at the end of dosing. Tissue extracts were prepared and analyzed for the presence of KAI-1678, which was detected in a subset of tissues from the two highest dose groups: liver, lung, kidney, brain (cerebrum), spinal cord, injection site (consisting of skin and underlying skeletal muscle), a peripheral nerve in the left fore-limb, and muscle in the leg (not proximal to infusion site). In general, tissue levels of KAI-1678 in the major organs (kidney, liver and lung) increased with increasing dose and reflected differences that were seen in plasma levels. As expected, KAI-1678 concentrations were highest in the infusion site skin (i.e., for 25,000 mcg/kg/day animals), although the underlying muscle had relatively low levels. KAI-1678 levels in nervous system (spinal cord and ulnar nerve) and peripheral tissues (muscle and skin) were less consistent between animals and dose groups. The levels in the brain and spinal cord were, for the most part, consistently low, in many cases just above the limit of quantitation, indicating relatively low exposure of these tissues to subcutaneously infused KAI-1678.

TABLE 12

Tissue Levels of KAI-1678 in Dogs Administered KAI-1678 as a Subcutaneous Infusion at 25 mg/kg/day for Five Days

|  | Animal 4001 (25 mg/kg/day male) Mean (ng KAI-1678/g tissue) | Std. Dev. | Animal 4501 (25 mg/kg/day female) Mean (ng KAI-1678/g tissue) | Std. Dev. |
|---|---|---|---|---|
| Brain | 6* | 1.2 | 7 | 1.3 |
| Spinal Cord | 11 | 1.3 | 140 | 13 |
| Peripheral Nerve | 429 | 56 | 155 | 14 |
| Lung | 254 | 22 | 1364 | 150 |
| Liver | 224 | 15 | 1505 | 176 |
| Kidney | 689 | 84 | 3054 | 522 |
| Skeletal Muscle | 133 | 20 | 33 | 4 |
| Dose Site Muscle | 111 | 14 | 1003 | 155 |
| Dose Site Skin | 1139 | 88 | 6165 | 998 |

*includes at least one data point that was below the specified limits of quantitation.

The invention claimed is:

1. A linear therapeutic peptide comprising the sequence EAVSLKPTGGYGRKKRRQRRR-NH2 (SEQ ID NO:62).

2. The linear therapeutic peptide according to claim 1, consisting of the sequence EAVSLKPTGGYGRKKRRQRRR-NH2 (SEQ ID NO:62).

3. A linear therapeutic peptide comprising the sequence Ac-EAVSLKPTGGYGRKKRRQRRR-NH2 (SEQ ID NO:57).

4. The linear therapeutic peptide according to claim 3 consisting of the sequence Ac-EAVSLKPTGGYGRKKRRQRRR-NH2 (SEQ ID NO:57).

5. A pharmaceutical composition comprising a linear therapeutic peptide comprising the sequence EAVSLKPTGGYGRKKRRQRRR-NH2 (SEQ ID NO:62).

6. The pharmaceutical composition of claim 5, comprising a linear therapeutic peptide consisting of the sequence EAVSLKPTGGYGRKKRRQRRR-NH2 (SEQ ID NO:62).

7. A pharmaceutical composition comprising a linear therapeutic peptide comprising the sequence Ac-EAVSLKPTGGYGRKKRRQRRR-NH2 (SEQ ID NO:57).

8. The pharmaceutical composition of claim 7, comprising a linear therapeutic peptide consisting of the sequence Ac-EAVSLKPTGGYGRKKRRQRRR-NH2 (SEQ ID NO:57).

9. A method of treating pain, comprising:
administering to a subject suffering from pain an effective amount of a modified epsilon protein kinase C (ePKC) inhibitory construct, wherein said inhibitor construct comprises the sequence of EAVSLKFTGGYGRKKRRQRRR-NH2 (SEQ ID NO:62) or Ac-EAVSLKPTGGYGRKKRRQRRR-NH2 (SEC) ID NO:57).

10. The method of claim 9, wherein the pain is selected from the group consisting of acute pain, chronic pain, neuropathic pain, and inflammatory pain.

11. The method of claim 9, wherein the modified ePKC inhibitory peptide is administered to the subject prior to, during, or subsequent to the subject receiving a pain stimulus.

12. The method of claim 11, wherein the modified ePKC inhibitory peptide is administered 5, 10, 15, 20, 25, 30, 35, 40, 45, 50, 55, one hour, several hours, one day, several days, one week, or weeks prior to the pain stimulus.

13. The method of claim 9, wherein the subject is suffering from chronic pain.

14. A method of achieving systemic anti-hyperalgesia, comprising:
administering to a subject via a subcutaneous route an effective amount of a modified epsilon protein kinase C (ePKC) inhibitory construct, wherein the modified ePKC peptide comprises the sequence of EAVSLKPTGGYGRKKRRQRRR-NH2 (SEQ ID NO:62) or Ac-EAVSLKPTGGYGRKKRRQRRR-NH2 (SEQ ID NO:57).

15. The method of claim 14, wherein the pain is selected from the group consisting of acute pain, chronic pain, neuropathic pain, and inflammatory pain.

16. The method of claim 14, wherein the modified ePKC inhibitory peptide is administered to the subject prior to, during, or subsequent to the subject receiving a pain stimulus.

17. The method of claim 16, wherein the inhibitory peptide is administered 5, 10, 15, 20, 25, 30, 35, 40, 45, 50, 55, one hour, several hours, one day, several days, one week, or weeks prior to the pain stimulus.

18. The method of claim 14, wherein the subject is suffering from chronic pain.

* * * * *